US007183046B2

(12) United States Patent
Glotzer et al.

(10) Patent No.: US 7,183,046 B2
(45) Date of Patent: Feb. 27, 2007

(54) METHODS FOR IDENTIFYING INHIBITORS OF CYTOKINESIS USING CYK-4 PROTEINS

(75) Inventors: Michael Glotzer, Vienna (AT); Verena Jantsch-Plunger, Vienna (AT); Alper Romano, Vienna (AT); Masanori Mishima, Vienna (AT); Susanne Kaitna, Vienna (AT)

(73) Assignee: Boehringer Ingelheim International GmbH (DE)

( * ) Notice: Subject to any disclaimer, the term of this patent is extended or adjusted under 35 U.S.C. 154(b) by 0 days.

(21) Appl. No.: 09/881,736

(22) Filed: Jun. 18, 2001

(65) Prior Publication Data

US 2002/0076785 A1   Jun. 20, 2002

Related U.S. Application Data

(60) Provisional application No. 60/297,434, filed on Jun. 13, 2001, provisional application No. 60/241,231, filed on Oct. 18, 2000.

(30) Foreign Application Priority Data

Jun. 19, 2000  (EP)  ................................. 00112880
Apr. 30, 2001  (EP)  ................................. 01110554

(51) Int. Cl.
*C12Q 1/00* (2006.01)
*G01N 33/53* (2006.01)

(52) U.S. Cl. .......................................... 435/4; 435/7.1
(58) Field of Classification Search .................... 435/4, 435/7.1, 6; 436/501
See application file for complete search history.

(56) References Cited

OTHER PUBLICATIONS

Kawashima et al, MgcRacGAP is involved in the control of growth and differentiation of hematopoietic cells. Blood 96:2116-2124, 2000.*
Adams, R.R. et al., "*pavarotti* encodes a kinesin-like protein required to organize the central spindle and contractile ring for cytokinesis," *Genes Dev.* 12:1483-1494, Cold Spring Harbor Laboratory Press (1998).
Aktories, K. and Hall, A., "Botulinum ADP-ribosyltransferase C₃: a new tool to study low molecular weight GTP-binding proteins," *Trends Pharmacol. Sci.* 10:415-418, Elsevier Science Publishers Ltd. (1989).
Bosher, J.M. and Labouesse, M., "RNA interference: genetic wand and genetic watchdog," *Nat. Cell Biol.* 2:E31-E36, Macmillan Publishers, Ltd. (Feb. 2000).
Boulianne, G.L. et al., "Production of functional chimaeric mouse/human antibody," *Nature* 312:643-646, Macmillan Publishing Group, Ltd. (1984).
Busson, S. et al., "Dynein and dynactin are localized to astral microtubules and at cortical sites in mitotic epithelial cells," *Curr. Biol.* 8:541-544, Current Biology Ltd. (1998).
Cao, L. -g. and Wang, Y.-l., "Signals from the Spindle Midzone Are Required for the Stimulation of Cytokinesis in Cultured Epithelial Cells," *Mol. Biol. Cell* 7:225-232, The American Society for Cell Biology (1996).
Carmena, M. et al., "*Drosophila* Polo Kinase Is Required for Cytokinesis," *J. Cell Biol.* 143:659-671, The Rockefeller University Press (1998).
Carminati, J.L. and Stearns, T., "Microtubules Orient the Mitotic Spindle in Yeast through Dynein-dependent Interactions with the Cell Cortex," *J. Cell Biol.* 138:629-641, The Rockefeller University Press (1997).
Case, R.B. et al., "Role of the kinesin neck linker and catalytic core in microtubule-based motility," *Curr. Biol.* 10:157-160, Elsevier Science Ltd. (Jan. 2000).
Castrillon, D.H. and Wasserman, S.A., "*diaphanous* is required for cytokinesis in *Drosophila* and shares domains of similarity with the products of the *limb deformity* gene," *Development* 120:3367-3377, The Company of Biologists Limited (1994).
Chang, F. et al., "cdc12p, a Protein Required for Cytokinesis in Fission Yeast, Is a Component of the Cell Division Ring and Interacts with Profilin," *J. Cell Biol.* 137:169-182, The Rockefeller University Press (1997).
Chui, K.K. et al., "Roles of Two Homotetrameric Kinesins in Sea Urchin Embryonic Cell Division," *J. Biol. Chem.* 275:38005-38011, The American Society for Biochemistry and Molecular Biology, Inc. (Dec. 2000).
Drechsel, D.N. et al., "A requirement for Rho and Cdc42 during cytokinesis in *Xenopus* embryos," *Curr. Biol.* 7:12-23, Current Biology Ltd. (1996).
Dutartre, H. et al., "Cytokinesis arrest and redistribution of actin-cytoskeleton regulatory components in cells expressing the Rho GTPase CDC42Hs," *J. Cell Sci.* 109:367-377, The Company of Biologists Limited (1996).
Echard, A. et al., "Interaction of a Golgi-Associated Kinesin-Like Protein with Rab6," *Science* 279:580-585, The American Association for the Advancement of Science (1998).
Eckley, D.M. et al., "Chromosomal Proteins and Cytokinesis: Patterns of Cleavage Furrow Formation and Inner Centromere Protein Positioning in Mitotic Heterokaryons and Mid-anaphase Cells," *J. Cell Biol.* 136:1169-1183, The Rockefeller University Press (1997).
Evangelista, M. et al., "Bni1p, a Yeast Formin Linking Cdc42p and the Actin Cytoskeleton During Polarized Morphogenesis," *Science* 276:118-122, The American Association for Advancement of Science (1997).
Field, C. et al., "Cytokinesis in eukaryotes: a mechanistic comparison," *Curr. Opin. Cell Biol.* 11:68-80, Elsevier Science Ltd. (Feb. 1999).
Fire, A. et al., "Potent and specific genetic interference by double-stranded RNA in *Caenorhabditis elegans*," *Nature* 391:806-811, Macmillan Publishers, Ltd. (1998).
Fire, A., "RNA-triggered gene silencing," *Trends Genet.* 15:358-363, Elsevier Science Ltd. (Sep. 1999).

(Continued)

*Primary Examiner*—Ruixiang Li
(74) *Attorney, Agent, or Firm*—Sterne, Kessler, Goldstein & Fox P.L.L.C.

(57) ABSTRACT

Mammalian CYK-4 polypeptides, which are key molecules required for cytokinesis, and DNA molecules encoding them. Screening methods based on biochemical reactions relevant for the function of CYK-4 can be employed to identify compounds interfering with cell division. Such compounds are useful in tumor therapy.

22 Claims, 32 Drawing Sheets

OTHER PUBLICATIONS

Fontijn, R.D. et al., "The Human Kinesin-Like Protein RB6K Is under Tight Cell Cycle Control and Is Essential for Cytokinesis," *Mol. Cell. Biol.* 21:2944-2955, American Society for Microbiology (Apr. 2001).

Fujiwara, T. et al., "Bni1p Regulates Microtubule-Dependent Nuclear Migration through the Actin Cytoskeleton in *Saccharomyces Cerevisiae*," *Mol. Cell. Biol.* 19:8016-8027, American Society for Microbiology (Dec. 1999).

Gentz, R. et al., "Bioassay for trans-activation using purified human immunodeficiency virus *tat*-encoded protein: Trans-activation requires mRNA synthesis," *Proc. Natl. Acad. Sci. USA* 86:821-824, The National Academy of Sciences (1989).

Giansanti, M.G. et al., "Cooperative interactions between the central spindle and the contractile ring during *Drosophila* cytokinesis," *Genes Dev.* 12:396-410, Cold Spring Harbor Laboratory Press (1998).

Glotzer, M., "Cytokinesis," *Curr. Biol.* 7:R274-R276, Current Biology Ltd. (1997).

Glotzer, M., "The mechanism and control of cytokinesis," *Curr. Opin. Cell Biol.* 9:815-823, Current Opinion Ltd. (1997).

Gönczy, P. et al., "Dissection of Cell Division Processes in the One Cell Stage *Caenorhabditis elegans* Embryo by Mutational Analysis," *J. Cell Biol.* 144:927-946, The Rockefeller University Press (Mar. 1999).

Gönczy, P. et al., "Cytoplasmic Dynein is Required for Distinct Aspects of MTOC Positioning, Including Centrosome Separation, in the One Cell Stage *Caenorhabditis elegans* Embryo," *J. Cell Biol.* 147:135-150, The Rockefeller University Press (Oct. 1999).

Graziano, R. F. et al. "Construction and Characterization of a Humanized Anti-γ-Ig Receptor Type I (FcγRI) Monoclonal Antibody," *J. Immunol.* 155:4996-5002, The American Association of Immunologists (1995).

Hazlett, T.L. et al., "Solution Dynamics of p21$^{ras}$ Proteins Bound with Fluorescent Nucleotides: A Time-Resolved Fluorescence Study," *Biochemistry* 32:13575-13583, American Chemical Society (1993).

Hill, E. et al., "The Rab6-binding kinesin, Rab6-KIFL, is required for cytokinesis," *EMBO J.* 19:5711-5719 European Molecular Biology Organization (Nov. 2000).

Hirose, K. et al., "MgcRacGAP Is Involved in Cytokinesis through Associating with Mitotic Spindle and Midbody," *J. Biol. Chem.* 276:5821-5828, The American Society for Biochemistry and Molecular Biology, Inc. (Feb. 2001).

Hurley, J.H. and Meyer, T., "Subcellular targeting by membrane lipids," *Curr. Opin. Cell Biol.* 13:1496-152, Elsevier Science Ltd. (Apr. 2001).

Hyman, A.A., "Centrosome Movement in the Early Divisions of *Caenorhabditis elegans*: A Cortical Site Determining Centrosome Position," *J. Cell Biol.* 109:1185-1193, The Rockefeller University Press (1989).

Hyman, A.A. and White, J.G., "Determination of Cell Division Axes in the Early Embryogenesis of *Caenorhabditis elegans*," *J. Cell Biol.* 105:2123-2135, The Rockefeller University Press (1987).

Imamura, H. et al., "Bni1p and Bnr1p: downstream targets of the Rho family small G-proteins which interact with profilin and regulate actin cytoskeleton in *Saccharomyces cerevisiae*," *EMBO J.* 16:2745-2755, Oxford University Press (1997).

Jantsch-Plunger, V. and Glotzer, M., "Depletion of syntaxins in the early *Caenorhabditis elegans* embryo reveals a role for membrane fusion events in cytokinesis," *Curr. Biol.* 9:738-745, Current Biology Ltd. (Jun. 1999).

Jantsch-Plunger, V. et al., "CYK-4: A Rho Family GTPase Activating Protein (GAP) Required for Central Spindle Formation and Cytokinesis," *J. Cell Biol.* 149:1391-1404, The Rockefeller University Press (Jun. 2000).

Kaitna, S. et al., "Incenp and an Aurora-like kinase form a complex essential for chromosome segregation and efficient completion of cytokinesis," *Curr. Biol.* 10:1172-1181, Elsevier Science Ltd. (Sep. 2000).

Kishi, K. et al., "Regulation of Cytoplasmic Division of *Xenopus* Embryo by *rho* p21 and Its Inhibitory GDP/GTP Exchange Protein (*rho* GDI)," *J. Cell Biol.* 120:1187-1195, The Rockefeller University Press (1993).

Kosako, H. et al., "Specific accumulation of Rho-associated kinase at the cleavage furrow during cytokinesis: cleavage furrow-specific phosphorylation of intermediate filaments," *Oncogene* 18:2783-2788, Stockton Press (Apr. 1999).

Kull, F.J. et al., "Crystal structure of the kinesin motor domain reveals a structural similarity to myosin," *Nature* 380:550-555, Macmillan Publishers Ltd. (1996).

Kuriyama, R. et al. "Heterogeneity and microtubule interaction of the CHO1 antigen, a mitosis-specific kinesin-like protein. Analysis of subdomains expressed in insect sf9 cells," *J. Cell Sci.* 107:3485-3499, The Company of Biologists Limited (1994).

Lamarche, N. and Hall, A., "GAPs for rho-related GTPases," *Trends Genet.* 10:436-440, Elsevier Science Ltd. (1994).

Larkin, K. and Danilchik, M.V., "Microtubules Are Required for Completion of Cytokinesis in Sea Urchin Eggs," *Dev. Biol.* 214:215-226, Academic Press (Oct. 1999).

Lee, K.S. et al., "Plk Is an M-Phase-Specific Protein Kinase and Interacts with a Kinesin-Like Protein, CHO1/MKLP-1," *Mol. Cell. Biol.* 15:7143-7151, American Society for Microbiology (1995).

Lewis, J.A. and Fleming, J.T., "Basic Culture Methods," *Methods Cell Biol.* 48:3-29, Academic Press, Inc. (1995).

Mabuchi, I. et al., "A rho-like protein is involved in the organisation of the contractile ring in dividing sand dollar eggs," *Zygote* 1:325-331, Cambridge University Press (1993).

Mackay, A.M. et al., "A Dominant Mutant of Inner Centromere Protein (INCENP), a Chromosomal Protein, Disrupts Prometaphase Congression and Cytokinesis," *J. Cell Biol.* 140:991-1002, The Rockefeller University Press (1998).

Martineau-Thuillier, S. et al., "Colocalization of TD-60 and INCENP throughout G2 and mitosis: evidence for their possible interaction in signalling cytokinesis," *Chromosoma* 107:461-470, Springer-Verlag (1998).

Mastronarde, D.N. et al., "Interpolar Spindle Microtubules in PTK Cells," *J. Cell Biol.* 123:1475-1489, The Rockefeller University Press (1993).

Mello, C.C. et al., "Efficient gene transfer in *C.elegans*: extrachromosomal maintenance and integration of transforming sequences," *EMBO J.* 10:3959-3970, Oxford University Press (1991).

Miller, R.K. et al., "The Cortical Localization of the Microtubule Orientation Protein, Kar9p, Is Dependent upon Actin and Proteins Required for Polarization," *J. Cell Biol.* 144:963-975, The Rockefeller University Press (Mar. 1999).

Moorman, J. P. et al., "Inactivation of the Small GTP Binding Protein Rho Induces Multinucleate Cell Formation and Apoptosis in Murine T Lymphoma EL4," *J. Immunol.* 156:4146-4153, The American Association of Immunologists (1996).

Neuberger, M.S. et al., "Recombinant antibodies possessing novel effector functions," *Nature* 312:604-608, Macmillan Publishers Ltd. (1984).

Nislow, C. et al., "A plus-end-directed motor enzyme that moves antiparallel microtubules *in vitro* localizes to the interzone of mitotic spindles," *Nature* 359:543-547, Macmillan Publishers Ltd. (1992).

O'Connell, K.F. et al., "A Genetic Screen for Temperature-Sensitive Cell-Division Mutants of *Caenorhabditis elegans*," *Genetics* 149:1303-1321 (1998).

O'Connell, C.B. et al., "The Small GTP-binding Protein Rho Regulates Cortical Activities in Cultured Cells during Division," *J. Cell Biol.* 144:305-313, The Rockefeller University Press (Jan. 1999).

Okada, Y. and Hirokawa, N., "Mechanism of the single-headed processivity: Diffusional anchoring between the K-loop of kinesin and the C terminus of tubulin," *Proc. Natl. Acad. Sci. USA* 97:640-645, The National Academy of Sciences (Jan. 2000).

Powers, J. et al., "A nematode kinesin required for cleavage furrow advancement," *Curr. Biol.* 8:1133-1136, Current Biology Ltd. (1998).

Prokopenko, S.N. et al., "A putative exchange factor for Rho1 GTPase is required for initiation of cytokinesis in *Drosophila*," *Genes Dev. 13*:2301-2314, Cold Spring Harbor Laboratory Press (Sep. 1999).

Raich, W.B. et al., "Cytokinesis and Midzone Microtubule Organization in *Caenorhabditis elegans* Require the Kinesin-like Protein ZEN-4," *Mol. Biol. Cell 9*:2037-2049, The American Society for Cell Biology (1998).

Rappaport, R., "Repeated Furrow Formation From a Single Mitotic Apparatus in Cylindrical Sand Dollar Eggs," *J. Exp. Zool. 234*:167-171, Alan R. Liss, Inc. (1985).

Reddien, P. and Horvitz, H.R., "CED-2/CrkII and CED-10/Rac control phagocytosis and cell migration in *Caenorhabditis elegans*," *Nat. Cell Biol. 2*:131-136, Macmillan Publishers Inc. (Mar. 2000).

Rice, S. et al., "A structural change in the kinesin motor protein that drives motility," *Nature 402*:778-784, Macmillan Publishers Inc. (Dec. 1999).

Riechmann, L. et al., "Reshaping human antibodies for therapy," *Nature 332*:323-327, Macmillan Publishers Inc. (1988).

Rieder, C.L. et al., "Mitosis in vertebrate somatic cells with two spindles: Implications for the metaphase/anaphase transition checkpoint and cleavage," *Proc. Natl. Acad. Sci. USA 94*:5107-5112, The National Academy of Sciences (1997).

Sablin, E.P. et al., "Crystals structure of the motor domain of the kinesin-related motor ncd," *Nature 380*:555-559, Macmillan Publishers Inc. (1996).

Savoian, M.S. et al., "Cleavage Furrows Formed between Centrosomes Lacking an Intervening Spindle and Chromosomes Contain Microtubule Bundles, INCENP, and CHO1 but Not CENP-E," *Mol. Biol. Cell 10*:297-311, The American Society for Cell Biology (Feb. 1999).

Saxton, W.M. and McIntosh, J.R., "Interzone Microtubule Behavior in Late Anaphase and Telophase Spindles," *J. Cell Biol. 105*:875-886, The Rockefeller University Press (1987).

Schumacher, J.M. et al., "AIR-2: An Aurora/Ipl1-related Protein Kinase Associated with Chromosomes and Midbody Microtubules Is Required for Polar Body Extrusion and Cytokinesis in *Caenorhabditis elegans* Embryos," *J. Cell Biol. 143*:1635-1646, The Rockefeller University Press (1998).

Settleman, J. and Foster, R., "Purification and GTPase-Activating Protein Activity of Baculovirus Expressed p190," *Methods Enzymol. 256*:105-113, Academic Press, Inc. (1995).

Severson, A.F. et al., "The Aurora-related kinase AIR-2 recruits ZEN-4/CeMKLP1 to the mitotic spindle at metaphase and is required for cytokinesis," *Curr. Biol. 10*:1162-1171, Current Biology Ltd. (Sep. 2000).

Sharp, D.J. et al., "Expression of a Kinesin-Related Motor Protein Induces Sf9 Cells to Form Dendrite-Like Processes with Nonuniform Microtubule Polarity Orientation," *J. Neurosci. 16*:4370-4375, Society for Neuroscience (1996).

Sharp, P.A., "RNAi and double-strand RNA," *Genes Dev. 13*:139-141, Cold Spring Harbor Laboratory Press (Jan. 1999).

Skop, A.R. and White, J.G., "The dynactin complex is required for cleavage plane specification in early *Caenorhabditis elegans* embryos," *Curr. Biol. 8*:1110-1116, Current Biology Ltd. (1998).

Sugihara, K. et al., "Rac1 is required for the formation of three germ layers during gastrulation," *Oncogene 17*:3427-3433, Stockton Press (1998).

Sulston, J.E. and Horvitz, H.R., "Post-embryonic Cell Lineages of the Nematode, *Caenorhabditis elegans*," *Dev. Biol. 56*:110-156, Academic Press, Inc. (1977).

Swan, K.A. et al., "*cyk-1*: a *C. elegans* FH gene required for a late step in embryonic cytokinesis," *J. Cell Sci. 111*:2017-2027, The Company of Biologists Ltd. (1998).

Tatsumoto, T. et al., "Human ECT2 Is an Exchange Factor for Rho GTPases, Phosphorylated in G2/M phases, and Involved in Cytokinesis," *J. Cell Biol. 147*:921-927, The Rockefeller University Press (Nov. 1999).

Timmons, L., and Fire, A., "Specific Interference by ingested dsRNA," *Nature 395*:854, Macmillan Publishers Inc. (1998).

Touré, A. et al., "MgcRacGAP, A New Human GTPase-activating Protein for Rac and Cdc42 Similar to *Drosophila rotundRacGAP* Gene Product, Is Expressed in Male Germ Cells," *J. Biol. Chem. 273*:6019-6023, The American Society for Biochemistry and Molecular Biology, Inc. (1998).

Vale, R.D. and Fletterick, R.J., "The Design Plan of Kinesin Motors," *Annu. Rev. Cell Dev. Biol. 13*:745-777, Annual Reviews, Inc. (1997).

Vale, R.D. and Milligan, R.A., "The Way Things Move: Looking Under the Hood of Molecular Motor Proteins," *Science 288*:88-95, The American Association for the Advancement of Science (Apr. 2000).

Van Aelst, L. and D'Souza-Schorey, C., "Rho GTPases and signaling networks," *Genes Dev. 11*:2295-2322, Cold Spring Harbor Laboratory Press (1997).

Van de Putte, T. et al., "Mice with a homozygous gene trap vector insertion in *mgcRacGAP* die during pre-implantation development," *Mech. Dev. 102*:33-44, Elsevier Science Ireland Ltd. (Apr. 2001).

Waddle, J.A. et al., "Transient localized accumulation of acting in *Caenorhabditis elegans* blastomeres with oriented asymmetric divisions," *Development 120*:2317-2328, The Company of Biologists Limited (1994).

Watanabe, N. et al., "p140mDia, a mammalian homolog of *Drosophila* diaphanous, is a target protein for Rho small GTPase and is a ligand for profilin," *EMBO J. 16*:3044-3056, Oxford University Press (1997).

Wheatley, S.P. and Wang, Y.-1., "Midzone Microtubule Bundles Are Continuously Required for Cytokinesis in Cultured Epithelial Cells," *J. Cell Biol. 135*:981-989, The Rockefeller University Press (1996).

Wilson, I.A. et al., "The Structure of an Antigenic Determinant in a Protein," *Cell 37*:767-778, The Massachusetts Institute of Technology (1984).

Winnacker, E.-L., "Directed Mutagenesis," in *From Genes to Clones: Introduction to Gene Technology*, Winnacker, E.-L., ed., VCH Verlagsgesellschaft mbH, Weinheim, Germany, pp. 451-481 (1987).

Woollard, A. and Hodgkin, J., "*Stu-71air-2* is a *C. elegans aurora* homologue essential for chromosome segregation during embryonic and post-embryonic development," *Mech. Dev. 82*:95-108, Elsevier Science Ireland Ltd. (Apr. 1999).

Swiss Institute of Bioinformatics and the European Bioinformatics Institute, SWISS-PROT report, Accession No. P01121 (entered Jul. 1986).

Swiss Institute of Bioinformatics and the European Bioinformatics Institute, SWISS-PROT report, Accession No. P06749 (entered Jan. 1988).

Swiss Institute of Bioinformatics and the European Bioinformatics Institute, SWISS-PROT report, Accession No. P08134 (entered Aug. 1988).

Swiss Institute of Bioinformatics and the European Bioinformatics Institute, SWISS-PROT report, Accession No. P15153 (entered Apr. 1990).

Swiss Institute of Bioinformatics and the European Bioinformatics Institute, SWISS-PROT report, Accession No. P15154 (entered Apr. 1990).

Swiss Institute of Bioinformatics and the European Bioinformatics Institute, SWISS-PROT report, Accession No. P21181 (entered May 1991).

Swiss Institute of Bioinformatics and the European Bioinformatics Institute, SWISS-PROT report, Accession No. O14658 (entered Jul. 1998).

NCBI Entrez, GenBank Report, Accesion No. X67155, Nislow, C. et al., (Jan. 2000).

NCBI Entrez, GenBank Report, Accession No. 061955, The *C. elegans* Sequencing Consortium (Sep. 2001).

NCBI Entrez, Genbank Report, Accession No. U61955, Version U61955.1 (GI:3258581), Wilson, R., et al. (Submitted Jun. 26, 1998).

NCBI Entrez, Genbank Report, Accession No. X67155, Versio X67155.2 (GI: 6723674), Nislow, C., et al. (Submitted Jan. 19, 2000).

NCBI Entrez, Genbank Report, Revision History for Accession No. U61955, Wilson, R., et al. (Dec. 10, 2004).

NCBI Entrez, Genbank Report, Revision History for Accession No. X67155, Nislow, C., et al. (Dec. 10, 2004).

* cited by examiner

Fig. 3 A,B,C
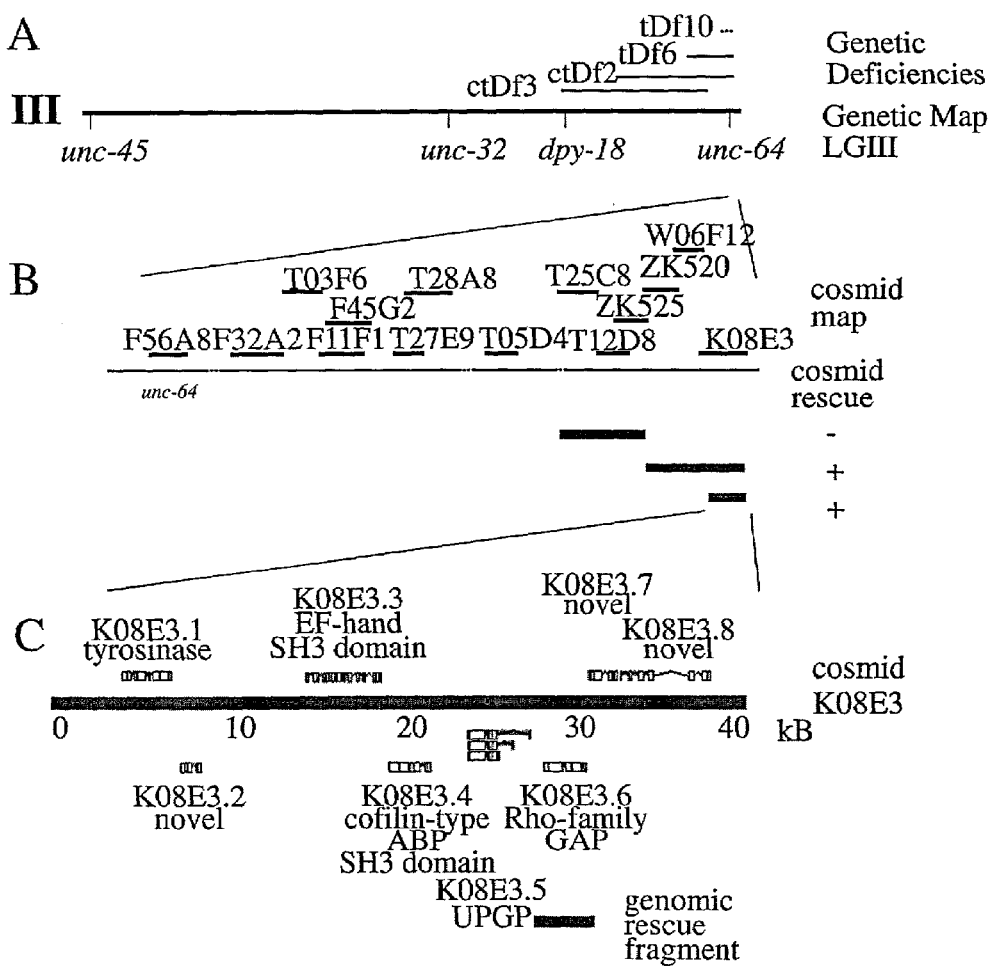

Zen-4/CeMklp1 homodimer

Cyk-4

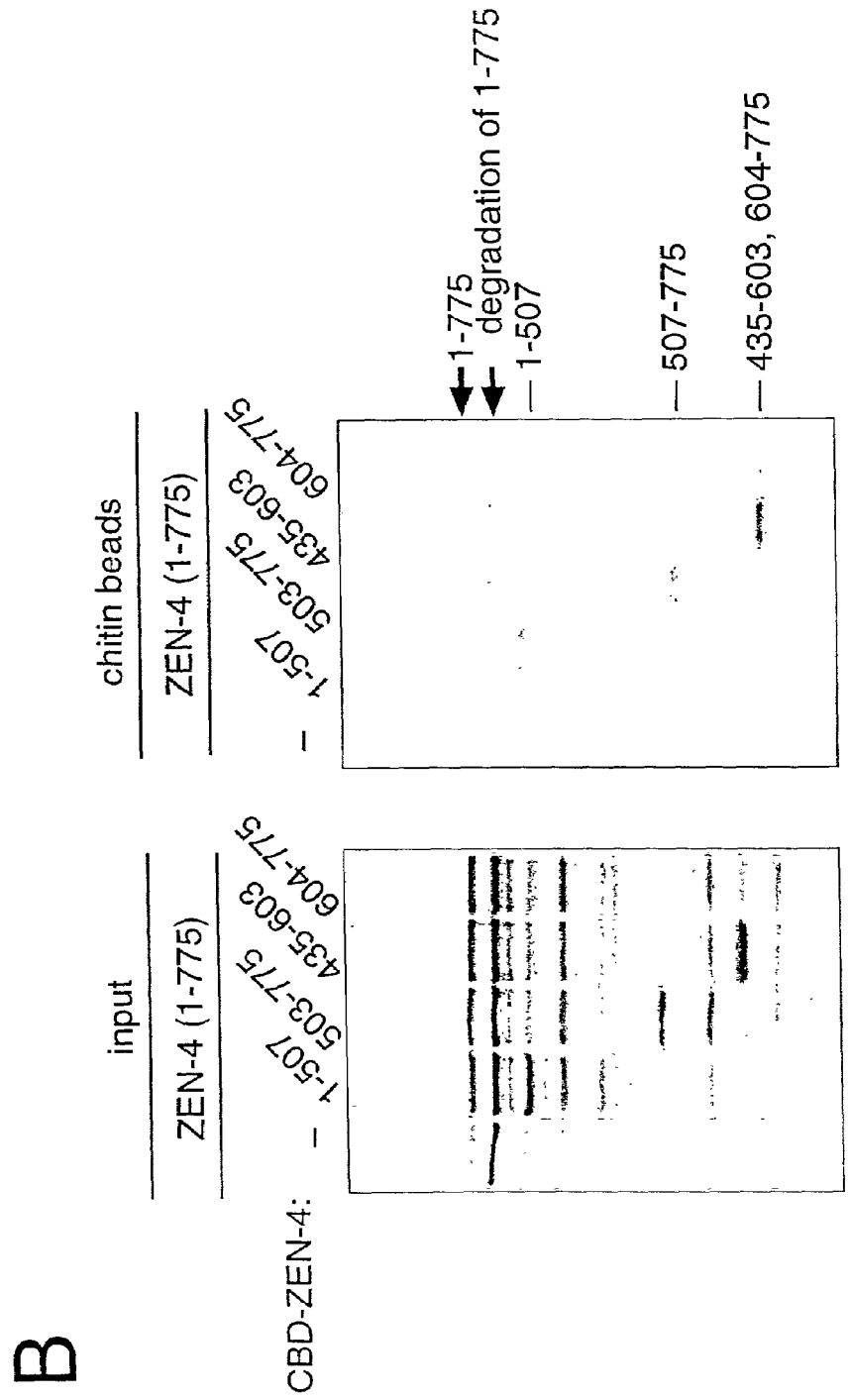

SEQUENCE LISTING

```
<160> NUMBER OF SEQ ID NOS: 6

<210> SEQ ID NO 1
<211> LENGTH: 3050
<212> TYPE: DNA
<213> ORGANISM: Homo sapiens
<220> FEATURE:
<221> NAME/KEY: 5'UTR
<222> LOCATION: (1)..(70)
<221> NAME/KEY: CDS
<222> LOCATION: (71)..(1969)
<221> NAME/KEY: 3'UTR
<222> LOCATION: (1970)..(3050)

<400> SEQUENCE: 1 taaaggggg tgccagacca ggtgcgtctg ccgctggatt gtgataggaa gcagagtgtt      60
cgtgtgaaag atg gat act atg atg ctg aat gtg cgg aat ctg ttt gag     109
          Met Asp Thr Met Met Leu Asn Val Arg Asn Leu Phe Glu
            1               5                  10
```

-continued

```
cag ctt gtg cgc cgg gtg gag att ctc agt gaa gga aat gaa gtc caa    157
Gln Leu Val Arg Arg Val Glu Ile Leu Ser Glu Gly Asn Glu Val Gln
     15                  20                  25 ttt atc cag ttg gcg aag gac ttt gag gat ttc cgt aaa aag tgg cag    205
Phe Ile Gln Leu Ala Lys Asp Phe Glu Asp Phe Arg Lys Lys Trp Gln
 30                  35                  40                  45 agg act gac cat gag ctg ggg aaa tac aag gat ctt ttg atg aaa gca    253
Arg Thr Asp His Glu Leu Gly Lys Tyr Lys Asp Leu Leu Met Lys Ala
                 50                  55                  60 gag act gag cga agt gct ctg gat gtt aag ctg aag cat gca cgt aat    301
Glu Thr Glu Arg Ser Ala Leu Asp Val Lys Leu Lys His Ala Arg Asn
             65                  70                  75 cag gtg gat gta gag atc aaa cgg aga cag aga gct gag gct gac tgc    349
Gln Val Asp Val Glu Ile Lys Arg Arg Gln Arg Ala Glu Ala Asp Cys
         80                  85                  90 gaa aag ctg gaa cga cag att cag ctg att cga gag atg ctc atg tgt    397
Glu Lys Leu Glu Arg Gln Ile Gln Leu Ile Arg Glu Met Leu Met Cys
     95                 100                 105 gac aca tct ggc agc att caa cta agc gag gag caa aaa tca gct ctg    445
Asp Thr Ser Gly Ser Ile Gln Leu Ser Glu Glu Gln Lys Ser Ala Leu
110                 115                 120                 125 gct ttt ctc aac aga ggc caa cca tcc agc agc aat gct ggg aac aaa    493
Ala Phe Leu Asn Arg Gly Gln Pro Ser Ser Ser Asn Ala Gly Asn Lys
                130                 135                 140 aga cta tca acc att gat gaa tct ggt tcc att tta tca gat atc agc    541
Arg Leu Ser Thr Ile Asp Glu Ser Gly Ser Ile Leu Ser Asp Ile Ser
            145                 150                 155 ttt gac aag act gat gaa tca ctg gat tgg gac tct tct ttg gtg aag    589
Phe Asp Lys Thr Asp Glu Ser Leu Asp Trp Asp Ser Ser Leu Val Lys
        160                 165                 170 act ttc aaa ctg aag aag aga gaa aag agg cgc tct act agc cga cag    637
Thr Phe Lys Leu Lys Lys Arg Glu Lys Arg Arg Ser Thr Ser Arg Gln
    175                 180                 185 ttt gtt gat ggt ccc cct gga cct gta aag aaa act cgt tcc att ggc    685
Phe Val Asp Gly Pro Pro Gly Pro Val Lys Lys Thr Arg Ser Ile Gly
190                 195                 200                 205 tct gca gta gac cag ggg aat gaa tcc ata gtt gca aaa act aca gtg    733
Ser Ala Val Asp Gln Gly Asn Glu Ser Ile Val Ala Lys Thr Thr Val
                210                 215                 220 act gtt ccc aat gat ggc ggg ccc atc gaa gct gtg tcc act att gag    781
Thr Val Pro Asn Asp Gly Gly Pro Ile Glu Ala Val Ser Thr Ile Glu
            225                 230                 235 act gtg cca tat tgg acc agg agc cga agg aaa aca ggt act tta caa    829
Thr Val Pro Tyr Trp Thr Arg Ser Arg Arg Lys Thr Gly Thr Leu Gln
        240                 245                 250 cct tgg aac agt gac tcc acc ctg aac agc agg cag ctg gag cca aga    877
Pro Trp Asn Ser Asp Ser Thr Leu Asn Ser Arg Gln Leu Glu Pro Arg
255                 260                 265 act gag aca gac agt gtg ggc acg cca cag agt aat gga ggg atg cgc    925
Thr Glu Thr Asp Ser Val Gly Thr Pro Gln Ser Asn Gly Gly Met Arg
270                 275                 280                 285 ctg cat gac ttt gtt tct aag acg gtt att aaa cct gaa tcc tgt gtt    973
Leu His Asp Phe Val Ser Lys Thr Val Ile Lys Pro Glu Ser Cys Val
                290                 295                 300 cca tgt gga aag cgg ata aaa ttt ggc aaa tta tct ctg aag tgt cga   1021
Pro Cys Gly Lys Arg Ile Lys Phe Gly Lys Leu Ser Leu Lys Cys Arg
            305                 310                 315 gac tgt cgt gtg gtc tct cat cca gaa tgt cgg gac cgc tgt ccc ctt   1069
Asp Cys Arg Val Val Ser His Pro Glu Cys Arg Asp Arg Cys Pro Leu
        320                 325                 330
```

-continued

| | |
|---|---|
| ccc tgc att cct acc ctg ata gga aca cct gtc aag att gga gag gga<br>Pro Cys Ile Pro Thr Leu Ile Gly Thr Pro Val Lys Ile Gly Glu Gly<br>335                           340                         345 | 1117 |
| atg ctg gca gac ttt gtg tcc cag act tct cca atg atc ccc tcc att<br>Met Leu Ala Asp Phe Val Ser Gln Thr Ser Pro Met Ile Pro Ser Ile<br>350                       355                      360                  365 | 1165 |
| gtt gtg cat tgt gta aat gag att gag caa aga ggt ctg act gag aca<br>Val Val His Cys Val Asn Glu Ile Glu Gln Arg Gly Leu Thr Glu Thr<br>                  370                      375                      380 | 1213 |
| ggc ctg tat agg atc tct ggc tgt gac cgc aca gta aaa gag ctg aaa<br>Gly Leu Tyr Arg Ile Ser Gly Cys Asp Arg Thr Val Lys Glu Leu Lys<br>385                       390                      395 | 1261 |
| gag aaa ttc ctc aga gtg aaa act gta ccc ctc ctc agc aaa gtg gat<br>Glu Lys Phe Leu Arg Val Lys Thr Val Pro Leu Leu Ser Lys Val Asp<br>        400                      405                  410 | 1309 |
| gat atc cat gct atc tgt agc ctt cta aaa gac ttt ctt cga aac ctc<br>Asp Ile His Ala Ile Cys Ser Leu Leu Lys Asp Phe Leu Arg Asn Leu<br>415                       420                      425 | 1357 |
| aaa gaa cct ctt ctg acc ttt cgc ctt aac aga gcc ttt atg gaa gca<br>Lys Glu Pro Leu Leu Thr Phe Arg Leu Asn Arg Ala Phe Met Glu Ala<br>430                       435                      440                  445 | 1405 |
| gca gaa atc aca gat gaa gac aac agc ata gct gcc atg tac caa gct<br>Ala Glu Ile Thr Asp Glu Asp Asn Ser Ile Ala Ala Met Tyr Gln Ala<br>                  450                      455                      460 | 1453 |
| gtt ggt gaa ctg ccc cag gcc aac agg gac aca tta gct ttc ctc atg<br>Val Gly Glu Leu Pro Gln Ala Asn Arg Asp Thr Leu Ala Phe Leu Met<br>465                       470                      475 | 1501 |
| att cac ttg cag aga gtg gct cag agt cca cat act aaa atg gat gtt<br>Ile His Leu Gln Arg Val Ala Gln Ser Pro His Thr Lys Met Asp Val<br>        480                      485                  490 | 1549 |
| gcc aat ctg gct aaa gtc ttt ggc cct aca ata gtg gcc cat gct gtg<br>Ala Asn Leu Ala Lys Val Phe Gly Pro Thr Ile Val Ala His Ala Val<br>495                       500                      505 | 1597 |
| ccc aat cca gac cca gtg aca atg tca cag gac atc aag cgt caa ccc<br>Pro Asn Pro Asp Pro Val Thr Met Ser Gln Asp Ile Lys Arg Gln Pro<br>510                       515                      520                  525 | 1645 |
| aag gtg gtt gag cgc ctg ctt tcc ttg cct ctg gag tat tgg agt cag<br>Lys Val Val Glu Arg Leu Leu Ser Leu Pro Leu Glu Tyr Trp Ser Gln<br>                  530                      535                      540 | 1693 |
| ttc atg atg gtg gag caa gag aac att gac ccc cta cat gtc att gaa<br>Phe Met Met Val Glu Gln Glu Asn Ile Asp Pro Leu His Val Ile Glu<br>545                       550                      555 | 1741 |
| aac tca aat gcc ttt tca aca cca cag aca cca gat att aaa gtg agt<br>Asn Ser Asn Ala Phe Ser Thr Pro Gln Thr Pro Asp Ile Lys Val Ser<br>        560                      565                  570 | 1789 |
| tta ctg gga cct gtg acc act cct gaa cat cag ctt ctc aag act cct<br>Leu Leu Gly Pro Val Thr Thr Pro Glu His Gln Leu Leu Lys Thr Pro<br>575                       580                      585 | 1837 |
| tca tct agt tcc ctg tca cag aga gtc cgt tcc acc ctc acc aag aac<br>Ser Ser Ser Ser Leu Ser Gln Arg Val Arg Ser Thr Leu Thr Lys Asn<br>590                       595                      600                  605 | 1885 |
| act cct aga ttt ggg agc aaa agc aag tct gcc act aac cta gga cga<br>Thr Pro Arg Phe Gly Ser Lys Ser Lys Ser Ala Thr Asn Leu Gly Arg<br>                  610                      615                      620 | 1933 |
| caa ggc aac ttt ttt gct tct cca atg ctc aag tga agtcacatct<br>Gln Gly Asn Phe Phe Ala Ser Pro Met Leu Lys<br>625                       630 | 1979 |
| gcctgttact tcccagcatt gactgactat aagaaaggac acatctgtac tctgctctgc | 2039 |

-continued

```
agcctcctgt actcattact acttttagca ttctccaggc ttttactcaa gtttaattgt    2099
gcatgagggt tttattaaaa ctatatatat ctccccttcc ttctcctcaa gtcacataat    2159
atcagcactt tgtgctggtc attgttggga gcttttagat gagacatctt tccaggggta    2219
gaagggttag tatggaattg gttgtgattc tttttgggga aggggttat tgttcctttg     2279
gcttaaagcc aaatgctgct catagaatga tctttctcta gtttcattta gaactgattt    2339
ccgtgagaca atgacagaaa ccctacctat ctgataagat tagcttgtct cagggtggga    2399
agtgggaggg cagggcaaag aaaggattag accagaggat ttaggatgcc tccttctaag    2459
aaccagaagt tctcattccc cattatgaac tgagctataa tatggagctt tcataaaaat    2519
gggatgcatt gaggacagaa ctagtgatgg gagtatgcgt agctttgatt tggatgatta    2579
ggtctttaat agtgttgagt ggcacaacct tgtaaatgtg aaagtacaac tcgtatttat    2639
ctctgatgtg ccgctggctg aactttgggt tcatttgggg tcaaagccag ttttctttt     2699
aaaattgaat tcattctgat gcttggcccc catacccca accttgtcca gtggagccca     2759
acttctaaag gtcaatatat catcctttgg catcccaact accaataaag agtaggctat    2819
aagggaagat tgtcaatatt tgtggtaag  aaaagctaca gtcatttttt ctttgcactt    2879
tggatgctga aattttccc  atggaacata gccacatcta gatagatgtg agcttttct     2939
tctgttaaaa ttattcttaa tgtctgtaaa aacgattttc ttctgtagaa tgtttgactt    2999
cgtattgacc cttatctgta aaacaccat  ttgggataat atttggcttt a             3050
```

<210> SEQ ID NO 2
<211> LENGTH: 632
<212> TYPE: PRT
<213> ORGANISM: Homo sapiens

<400> SEQUENCE: 2

```
Met Asp Thr Met Met Leu Asn Val Arg Asn Leu Phe Glu Gln Leu Val
  1               5                  10                  15

Arg Arg Val Glu Ile Leu Ser Glu Gly Asn Glu Val Gln Phe Ile Gln
             20                  25                  30

Leu Ala Lys Asp Phe Glu Asp Phe Arg Lys Lys Trp Gln Arg Thr Asp
         35                  40                  45

His Glu Leu Gly Lys Tyr Lys Asp Leu Leu Met Lys Ala Glu Thr Glu
     50                  55                  60

Arg Ser Ala Leu Asp Val Lys Leu Lys His Ala Arg Asn Gln Val Asp
 65                  70                  75                  80

Val Glu Ile Lys Arg Arg Gln Arg Ala Glu Ala Asp Cys Glu Lys Leu
                 85                  90                  95

Glu Arg Gln Ile Gln Leu Ile Arg Glu Met Leu Met Cys Asp Thr Ser
            100                 105                 110

Gly Ser Ile Gln Leu Ser Glu Glu Gln Lys Ser Ala Leu Ala Phe Leu
        115                 120                 125

Asn Arg Gly Gln Pro Ser Ser Ser Asn Ala Gly Asn Lys Arg Leu Ser
    130                 135                 140

Thr Ile Asp Glu Ser Gly Ser Ile Leu Ser Asp Ile Ser Phe Asp Lys
145                 150                 155                 160

Thr Asp Glu Ser Leu Asp Trp Asp Ser Ser Leu Val Lys Thr Phe Lys
                165                 170                 175

Leu Lys Lys Arg Glu Lys Arg Arg Ser Thr Ser Arg Gln Phe Val Asp
            180                 185                 190

Gly Pro Pro Gly Pro Val Lys Lys Thr Arg Ser Ile Gly Ser Ala Val
```

-continued

```
                195                 200                 205
Asp Gln Gly Asn Glu Ser Ile Val Ala Lys Thr Thr Val Thr Val Pro
    210                 215                 220

Asn Asp Gly Gly Pro Ile Glu Ala Val Ser Thr Ile Glu Thr Val Pro
225                 230                 235                 240

Tyr Trp Thr Arg Ser Arg Lys Thr Gly Thr Leu Gln Pro Trp Asn
                245                 250                 255

Ser Asp Ser Thr Leu Asn Ser Arg Gln Leu Glu Pro Arg Thr Glu Thr
                260                 265                 270

Asp Ser Val Gly Thr Pro Gln Ser Asn Gly Gly Met Arg Leu His Asp
            275                 280                 285

Phe Val Ser Lys Thr Val Ile Lys Pro Glu Ser Cys Val Pro Cys Gly
        290                 295                 300

Lys Arg Ile Lys Phe Gly Lys Leu Ser Leu Lys Cys Arg Asp Cys Arg
305                 310                 315                 320

Val Val Ser His Pro Glu Cys Arg Asp Arg Cys Pro Leu Pro Cys Ile
                325                 330                 335

Pro Thr Leu Ile Gly Thr Pro Val Lys Ile Gly Glu Gly Met Leu Ala
            340                 345                 350

Asp Phe Val Ser Gln Thr Ser Pro Met Ile Pro Ser Ile Val Val His
        355                 360                 365

Cys Val Asn Glu Ile Glu Gln Arg Gly Leu Thr Glu Thr Gly Leu Tyr
    370                 375                 380

Arg Ile Ser Gly Cys Asp Arg Thr Val Lys Glu Leu Lys Glu Lys Phe
385                 390                 395                 400

Leu Arg Val Lys Thr Val Pro Leu Leu Ser Lys Val Asp Asp Ile His
                405                 410                 415

Ala Ile Cys Ser Leu Leu Lys Asp Phe Leu Arg Asn Leu Lys Glu Pro
            420                 425                 430

Leu Leu Thr Phe Arg Leu Asn Arg Ala Phe Met Glu Ala Ala Glu Ile
        435                 440                 445

Thr Asp Glu Asp Asn Ser Ile Ala Ala Met Tyr Gln Ala Val Gly Glu
    450                 455                 460

Leu Pro Gln Ala Asn Arg Asp Thr Leu Ala Phe Leu Met Ile His Leu
465                 470                 475                 480

Gln Arg Val Ala Gln Ser Pro His Thr Lys Met Asp Val Ala Asn Leu
                485                 490                 495

Ala Lys Val Phe Gly Pro Thr Ile Val Ala His Ala Val Pro Asn Pro
            500                 505                 510

Asp Pro Val Thr Met Ser Gln Asp Ile Lys Arg Gln Pro Lys Val Val
        515                 520                 525

Glu Arg Leu Leu Ser Leu Pro Leu Glu Tyr Trp Ser Gln Phe Met Met
    530                 535                 540

Val Glu Gln Glu Asn Ile Asp Pro Leu His Val Ile Glu Asn Ser Asn
545                 550                 555                 560

Ala Phe Ser Thr Pro Gln Thr Pro Asp Ile Lys Val Ser Leu Leu Gly
                565                 570                 575

Pro Val Thr Thr Pro Glu His Gln Leu Leu Lys Thr Pro Ser Ser Ser
            580                 585                 590

Ser Leu Ser Gln Arg Val Arg Ser Thr Leu Thr Lys Asn Thr Pro Arg
        595                 600                 605

Phe Gly Ser Lys Ser Lys Ser Ala Thr Asn Leu Gly Arg Gln Gly Asn
    610                 615                 620
```

```
Phe Phe Ala Ser Pro Met Leu Lys
625                 630

<210> SEQ ID NO 3
<211> LENGTH: 2919
<212> TYPE: DNA
<213> ORGANISM: Mus musculus
<220> FEATURE:
<221> NAME/KEY: 5'UTR
<222> LOCATION: (1)..(134)
<221> NAME/KEY: CDS
<222> LOCATION: (135)..(2021)
<221> NAME/KEY: 3'UTR
<222> LOCATION: (2022)..(2919)

<400> SEQUENCE: 3
ggaaagcggt tttacactgc cgttagtgag gcgcgtcgct ggtagacagc agccctcctg      60
gggcgcggcg gccggagagt gagcgccgcg ggccggacgg ggttgcgtgt gcgcggggcc     120
gggagcctcg aaag atg gat act aca atg gtg aat ttg tgg act ctg ttt      170
              Met Asp Thr Thr Met Val Asn Leu Trp Thr Leu Phe
               1               5                  10 gag cag ctt gtg cgc cgg atg gag att atc aat gaa gga aat gaa agc      218
Glu Gln Leu Val Arg Arg Met Glu Ile Ile Asn Glu Gly Asn Glu Ser
        15                  20                  25 att gaa ttc atc cag gtt gtg aag gac ttc gag gac ttc cga aag aag      266
Ile Glu Phe Ile Gln Val Val Lys Asp Phe Glu Asp Phe Arg Lys Lys
    30                  35                  40 tat caa aga acc aac cag gag ctg gag aaa ttc aaa gac cta ttg ttg      314
Tyr Gln Arg Thr Asn Gln Glu Leu Glu Lys Phe Lys Asp Leu Leu Leu
 45                  50                  55                  60 aaa gca gag act ggg cgg agc gcc ctg gac gtg aag ctg aag cat gcc      362
Lys Ala Glu Thr Gly Arg Ser Ala Leu Asp Val Lys Leu Lys His Ala
                 65                  70                  75 cgt aat caa gtg gac gtg gag atc aag cgg agg cag cgc gct gag gca      410
Arg Asn Gln Val Asp Val Glu Ile Lys Arg Arg Gln Arg Ala Glu Ala
             80                  85                  90 gag tgt gca aag ctg gaa caa cag att cag ctg att cga gac ata ctc      458
Glu Cys Ala Lys Leu Glu Gln Gln Ile Gln Leu Ile Arg Asp Ile Leu
         95                 100                 105 atg tgt gac aca tct ggc agt att cag ctg agt gag gaa caa aaa tca      506
Met Cys Asp Thr Ser Gly Ser Ile Gln Leu Ser Glu Glu Gln Lys Ser
    110                 115                 120 gct ctc gct ttc ctc aac cga ggc caa gca tcc agt ggc cac gcc ggc      554
Ala Leu Ala Phe Leu Asn Arg Gly Gln Ala Ser Ser Gly His Ala Gly
125                 130                 135                 140 aac aat aga ctg tca acg att gat gaa tct ggt tcc att tta tca gat      602
Asn Asn Arg Leu Ser Thr Ile Asp Glu Ser Gly Ser Ile Leu Ser Asp
                145                 150                 155 atc agc ttt gac aag act gat gaa tca ctg gac tgg gat tct tct ttg      650
Ile Ser Phe Asp Lys Thr Asp Glu Ser Leu Asp Trp Asp Ser Ser Leu
            160                 165                 170 gtg aag aat ttc aaa atg aag aaa cga gag aag agg cgc tcc aac agt      698
Val Lys Asn Phe Lys Met Lys Lys Arg Glu Lys Arg Arg Ser Asn Ser
        175                 180                 185 aga cag ttc atc gac ggc cct cct ggg cct gtg aag aaa act tgt tcc      746
Arg Gln Phe Ile Asp Gly Pro Pro Gly Pro Val Lys Lys Thr Cys Ser
    190                 195                 200 att ggc tct aca gta gac cag gca aat gaa tca ata gtt gca aaa act      794
Ile Gly Ser Thr Val Asp Gln Ala Asn Glu Ser Ile Val Ala Lys Thr
205                 210                 215                 220
```

```
                                                           -continued aca gtg act gtt ccc agt gat ggg gga ccc att gaa gct gtg tct act       842
Thr Val Thr Val Pro Ser Asp Gly Gly Pro Ile Glu Ala Val Ser Thr
                225                 230                 235 att gag aca ttg ccg tcc tgg acc agg agt cgc ggg aag tca gga cct       890
Ile Glu Thr Leu Pro Ser Trp Thr Arg Ser Arg Gly Lys Ser Gly Pro
    240                 245                 250 tta caa cct gtg aac agt gac tcc gct ctg aac agc agg cca ctg gag       938
Leu Gln Pro Val Asn Ser Asp Ser Ala Leu Asn Ser Arg Pro Leu Glu
255                 260                 265 cca aga act gac aca gac aat ttg ggc aca cct cag aat act gga ggc       986
Pro Arg Thr Asp Thr Asp Asn Leu Gly Thr Pro Gln Asn Thr Gly Gly
        270                 275                 280 atg cgc ttg cac gac ttc gtc tca aag acg gtt att aag cct gaa tct      1034
Met Arg Leu His Asp Phe Val Ser Lys Thr Val Ile Lys Pro Glu Ser
285                 290                 295                 300 tgt gtt ccg tgt gga aag cgg atc aag ttt ggc aag ctg tct ctg aag      1082
Cys Val Pro Cys Gly Lys Arg Ile Lys Phe Gly Lys Leu Ser Leu Lys
                305                 310                 315 tgt cga gac tgt cgt ttg gtc tcc cat cca gaa tgt cgg gac cga tgt      1130
Cys Arg Asp Cys Arg Leu Val Ser His Pro Glu Cys Arg Asp Arg Cys
                320                 325                 330 ccc ctt ccc tgc atc ccc ccg ctg gtg ggg aca ccg gtt aag att gga      1178
Pro Leu Pro Cys Ile Pro Pro Leu Val Gly Thr Pro Val Lys Ile Gly
            335                 340                 345 gag ggc atg ctg gcc gac ttc gtg tcg cag gct tct ccc atg atc cct      1226
Glu Gly Met Leu Ala Asp Phe Val Ser Gln Ala Ser Pro Met Ile Pro
350                 355                 360 gcc att gtc gtc agc tgt gtc aat gag atc gag cag cga ggc ctg act      1274
Ala Ile Val Val Ser Cys Val Asn Glu Ile Glu Gln Arg Gly Leu Thr
365                 370                 375                 380 gag gca ggc ttg tac agg atc tca ggc tgt gac cgc aca gtg aaa gaa      1322
Glu Ala Gly Leu Tyr Arg Ile Ser Gly Cys Asp Arg Thr Val Lys Glu
                385                 390                 395 ctg aaa gaa aaa ttc ctt aag gtg aaa act gtg ccc ctc ctc agc aaa      1370
Leu Lys Glu Lys Phe Leu Lys Val Lys Thr Val Pro Leu Leu Ser Lys
                400                 405                 410 gtg gac gat atc cac gtc atc tgc agc ctc ctg aag gac ttc ctg cgc      1418
Val Asp Asp Ile His Val Ile Cys Ser Leu Leu Lys Asp Phe Leu Arg
            415                 420                 425 aac ctc aaa gag ccc ctc ctg acc ttc tgg ctg agc aaa gcc ttc atg      1466
Asn Leu Lys Glu Pro Leu Leu Thr Phe Trp Leu Ser Lys Ala Phe Met
        430                 435                 440 gag gca gca gag ata aca gat gaa gac aac agc aca gcc gcc atg tac      1514
Glu Ala Ala Glu Ile Thr Asp Glu Asp Asn Ser Thr Ala Ala Met Tyr
445                 450                 455                 460 cag gct gtc agt gag ctg ccc cag gcc aac agg gac acg cta gcc ttc      1562
Gln Ala Val Ser Glu Leu Pro Gln Ala Asn Arg Asp Thr Leu Ala Phe
                465                 470                 475 ctt atg atc cac cta cag aga gtg tct cag agt cca gac act aag atg      1610
Leu Met Ile His Leu Gln Arg Val Ser Gln Ser Pro Asp Thr Lys Met
                480                 485                 490 gat att gcc aat cta gct aaa gtc ttt ggc cct aca ata gtt gcc cat      1658
Asp Ile Ala Asn Leu Ala Lys Val Phe Gly Pro Thr Ile Val Ala His
            495                 500                 505 act gtg ccc aat cca gat cca gtg aca atg ttc cag gac atc aaa cgt      1706
Thr Val Pro Asn Pro Asp Pro Val Thr Met Phe Gln Asp Ile Lys Arg
        510                 515                 520 cag ctc aag gtg gtg gag cgc cta ctc tct ctc ccc ttg gag tac tgg      1754
Gln Leu Lys Val Val Glu Arg Leu Leu Ser Leu Pro Leu Glu Tyr Trp
525                 530                 535                 540
```

-continued

```
aat cag ttc atg atg gtg gac caa gag aac ata gac agc cag cga ggc      1802
Asn Gln Phe Met Met Val Asp Gln Glu Asn Ile Asp Ser Gln Arg Gly
            545                 550                 555 aat gga aac tca aca cca cgc aca cca gac gtt aaa gtg agc tta ctg      1850
Asn Gly Asn Ser Thr Pro Arg Thr Pro Asp Val Lys Val Ser Leu Leu
        560                 565                 570 ggg cct gtg acc act cct gaa ttc cag ctt gtc aag act cct tta tca      1898
Gly Pro Val Thr Thr Pro Glu Phe Gln Leu Val Lys Thr Pro Leu Ser
    575                 580                 585 agt tcc ctg tca cag agg ttg tac aac ctc tcc aag agc aca ccc aga      1946
Ser Ser Leu Ser Gln Arg Leu Tyr Asn Leu Ser Lys Ser Thr Pro Arg
590                 595                 600 ttt ggg aac aag agc aag tct gcc acc aac tta ggt caa cag ggc aaa      1994
Phe Gly Asn Lys Ser Lys Ser Ala Thr Asn Leu Gly Gln Gln Gly Lys
605                 610                 615                 620 ttt ttc cct gct ccg tac ctc aag taa agctgtgtct gcctgtgttt            2041
Phe Phe Pro Ala Pro Tyr Leu Lys
                625 actgcacgag acacccctgt ctgctcttca gcctcctgtg taatgactac ttttagcatt    2101 ttccagactt taaataaagt tgaacgcgta tgagagtttg agtgttgcat agctccctcc    2161 cacctggaca cttagcacct ttactagttg tcgggagctt taaaatagga gatctttacc    2221 agggccgaag gggaaatggg tataagttgg ggctcttagg gggaggggag aggagatccc    2281 tttggcttaa agccaaatac tgctcatgaa atgactttgc tgtggtgtca cttagacaat    2341 gacagaaact gtacctctta ggtaacgtct tagttatctc aggacaggat aaagagctgc    2401 gcagcggccc cttctcagaa cacaggcctc ttcctccttc ggggactgac aagaagcttg    2461 gagccctcag cgggatgggc cgggccactg atctgaggat gcttcacttc tgtctgggtt    2521 aagctgagaa agtgccacag gctctgatct cacacagcgt gctgtttcta gccagcctct    2581 gcctggattt tgcagtcaaa gtcaggttga tctgaagccg aattcgttct gatgcctgac    2641 cccttgttt gtccagtgga gcccatttaa aaagtcagct agcagttcag aagacaattt     2701 tcatatagca agaaagttag ctgcttctgt ctttggtgaa gtttttctgt gaaacagatc    2761 tatatatgtg aacattggct ttttggtta gcattttcca gtgttcaaaa tggcttcctt     2821 ccctgggatg ttttctgacc catactaacc cttacctgta acatgtatct ggaatattat    2881 gtggaaaaaa taaatagctt tttcaaagtg aactttcc                           2919
```

```
<210> SEQ ID NO 4
<211> LENGTH: 628
<212> TYPE: PRT
<213> ORGANISM: Mus musculus

<400> SEQUENCE: 4

Met Asp Thr Thr Met Val Asn Leu Trp Thr Leu Phe Glu Gln Leu Val
1               5                   10                  15

Arg Arg Met Glu Ile Ile Asn Glu Gly Asn Glu Ser Ile Glu Phe Ile
            20                  25                  30

Gln Val Val Lys Asp Phe Glu Asp Phe Arg Lys Lys Tyr Gln Arg Thr
        35                  40                  45

Asn Gln Glu Leu Glu Lys Phe Lys Asp Leu Leu Leu Lys Ala Glu Thr
    50                  55                  60

Gly Arg Ser Ala Leu Asp Val Lys Leu Lys His Ala Arg Asn Gln Val
65                  70                  75                  80

Asp Val Glu Ile Lys Arg Arg Gln Arg Ala Glu Ala Glu Cys Ala Lys
```

```
                      85                  90                  95
Leu Glu Gln Gln Ile Gln Leu Ile Arg Asp Ile Leu Met Cys Asp Thr
            100                 105                 110
Ser Gly Ser Ile Gln Leu Ser Glu Glu Gln Lys Ser Ala Leu Ala Phe
            115                 120                 125
Leu Asn Arg Gly Gln Ala Ser Ser Gly His Ala Gly Asn Asn Arg Leu
130                 135                 140
Ser Thr Ile Asp Glu Ser Gly Ser Ile Leu Ser Asp Ile Ser Phe Asp
145                 150                 155                 160
Lys Thr Asp Glu Ser Leu Asp Trp Asp Ser Ser Leu Val Lys Asn Phe
                165                 170                 175
Lys Met Lys Lys Arg Glu Lys Arg Arg Ser Asn Ser Arg Gln Phe Ile
            180                 185                 190
Asp Gly Pro Pro Gly Pro Val Lys Lys Thr Cys Ser Ile Gly Ser Thr
            195                 200                 205
Val Asp Gln Ala Asn Glu Ser Ile Val Ala Lys Thr Thr Val Thr Val
210                 215                 220
Pro Ser Asp Gly Gly Pro Ile Glu Ala Val Ser Thr Ile Glu Thr Leu
225                 230                 235                 240
Pro Ser Trp Thr Arg Ser Arg Gly Lys Ser Gly Pro Leu Gln Pro Val
                245                 250                 255
Asn Ser Asp Ser Ala Leu Asn Ser Arg Pro Leu Glu Pro Arg Thr Asp
                260                 265                 270
Thr Asp Asn Leu Gly Thr Pro Gln Asn Thr Gly Gly Met Arg Leu His
            275                 280                 285
Asp Phe Val Ser Lys Thr Val Ile Lys Pro Glu Ser Cys Val Pro Cys
290                 295                 300
Gly Lys Arg Ile Lys Phe Gly Lys Leu Ser Leu Lys Cys Arg Asp Cys
305                 310                 315                 320
Arg Leu Val Ser His Pro Glu Cys Arg Asp Arg Cys Pro Leu Pro Cys
                325                 330                 335
Ile Pro Pro Leu Val Gly Thr Pro Val Lys Ile Gly Glu Gly Met Leu
            340                 345                 350
Ala Asp Phe Val Ser Gln Ala Ser Pro Met Ile Pro Ala Ile Val Val
            355                 360                 365
Ser Cys Val Asn Glu Ile Glu Gln Arg Gly Leu Thr Glu Ala Gly Leu
            370                 375                 380
Tyr Arg Ile Ser Gly Cys Asp Arg Thr Val Lys Glu Leu Lys Glu Lys
385                 390                 395                 400
Phe Leu Lys Val Lys Thr Val Pro Leu Leu Ser Lys Val Asp Asp Ile
                405                 410                 415
His Val Ile Cys Ser Leu Leu Lys Asp Phe Leu Arg Asn Leu Lys Glu
            420                 425                 430
Pro Leu Leu Thr Phe Trp Leu Ser Lys Ala Phe Met Glu Ala Ala Glu
            435                 440                 445
Ile Thr Asp Glu Asp Asn Ser Thr Ala Ala Met Tyr Gln Ala Val Ser
450                 455                 460
Glu Leu Pro Gln Ala Asn Arg Asp Thr Leu Ala Phe Leu Met Ile His
465                 470                 475                 480
Leu Gln Arg Val Ser Gln Ser Pro Asp Thr Lys Met Asp Ile Ala Asn
                485                 490                 495
Leu Ala Lys Val Phe Gly Pro Thr Ile Val Ala His Thr Val Pro Asn
            500                 505                 510
```

-continued

```
Pro Asp Pro Val Thr Met Phe Gln Asp Ile Lys Arg Gln Leu Lys Val
        515                 520                 525

Val Glu Arg Leu Leu Ser Leu Pro Leu Glu Tyr Trp Asn Gln Phe Met
        530                 535                 540

Met Val Asp Gln Glu Asn Ile Asp Ser Gln Arg Gly Asn Gly Asn Ser
545                 550                 555                 560

Thr Pro Arg Thr Pro Asp Val Lys Val Ser Leu Leu Gly Pro Val Thr
                565                 570                 575

Thr Pro Glu Phe Gln Leu Val Lys Thr Pro Leu Ser Ser Ser Leu Ser
            580                 585                 590

Gln Arg Leu Tyr Asn Leu Ser Lys Ser Thr Pro Arg Phe Gly Asn Lys
        595                 600                 605

Ser Lys Ser Ala Thr Asn Leu Gly Gln Gln Gly Lys Phe Phe Pro Ala
    610                 615                 620

Pro Tyr Leu Lys
625

<210> SEQ ID NO 5
<211> LENGTH: 2046
<212> TYPE: DNA
<213> ORGANISM: Caenorhabditis elegans
<220> FEATURE:
<221> NAME/KEY: CDS
<222> LOCATION: (1)..(2046)

<400> SEQUENCE: 5 atg aag tcc agt aca tca aaa gag aag gtg tgc ggc gaa aac tcg cgt    48
Met Lys Ser Ser Thr Ser Lys Glu Lys Val Cys Gly Glu Asn Ser Arg
  1               5                  10                  15 cac att ttc aac atg att cta aac tca cag cga ccg caa ttc gat att    96
His Ile Phe Asn Met Ile Leu Asn Ser Gln Arg Pro Gln Phe Asp Ile
             20                  25                  30 aag gat ata gga atg ttt cat ttg att gat gag att gag cgt ctc cgc   144
Lys Asp Ile Gly Met Phe His Leu Ile Asp Glu Ile Glu Arg Leu Arg
         35                  40                  45 aag ctg tgg aaa gat tcc gag gaa tcc aaa aag cgg ctg aat gca gat   192
Lys Leu Trp Lys Asp Ser Glu Glu Ser Lys Lys Arg Leu Asn Ala Asp
     50                  55                  60 atg aga gag gcc gaa gaa gca ctt gca aaa gct cgc aag aag ctg gca   240
Met Arg Glu Ala Glu Glu Ala Leu Ala Lys Ala Arg Lys Lys Leu Ala
 65                  70                  75                  80 atg ttc gat atc gat gtc aaa gac act cag aaa cat tta cgc gcg ttg   288
Met Phe Asp Ile Asp Val Lys Asp Thr Gln Lys His Leu Arg Ala Leu
                 85                  90                  95 atg gaa gaa aat aag gcg ttg aag ctc gat cta aac gtc tac gag act   336
Met Glu Glu Asn Lys Ala Leu Lys Leu Asp Leu Asn Val Tyr Glu Thr
            100                 105                 110 cgt gaa aag cag ctg aaa gat gcg atg aag aac ggt ata ttc aat agt   384
Arg Glu Lys Gln Leu Lys Asp Ala Met Lys Asn Gly Ile Phe Asn Ser
        115                 120                 125 ctc acc aag gaa gac cgc gat cag ttc aag ttt ctt cac gag cca ctg   432
Leu Thr Lys Glu Asp Arg Asp Gln Phe Lys Phe Leu His Glu Pro Leu
    130                 135                 140 gtc cgg aca tac tcg aaa cgg gtg cag cag agg cat cca cat ttg atg   480
Val Arg Thr Tyr Ser Lys Arg Val Gln Gln Arg His Pro His Leu Met
145                 150                 155                 160 gag gac aca cag gac gat gag gac gat agt gag gtg gat tac gat gaa   528
Glu Asp Thr Gln Asp Asp Glu Asp Asp Ser Glu Val Asp Tyr Asp Glu
                165                 170                 175
```

```
act gga gac agt ttc gag gaa gtt att cat ttg cgc aat gga aga gag      576
Thr Gly Asp Ser Phe Glu Glu Val Ile His Leu Arg Asn Gly Arg Glu
            180                 185                 190 gtc aga aga agc tca gct gct gga aac gca gtt ggt ggc aag cgg aga      624
Val Arg Arg Ser Ser Ala Ala Gly Asn Ala Val Gly Gly Lys Arg Arg
        195                 200                 205 agc gcg tca gca cat gcg att act gct gct gcc aat tcg aag agg agc      672
Ser Ala Ser Ala His Ala Ile Thr Ala Ala Ala Asn Ser Lys Arg Ser
    210                 215                 220 aga agc cgt gtt atg aca gct act ata gat gaa gag ccg aat gag ggt      720
Arg Ser Arg Val Met Thr Ala Thr Ile Asp Glu Glu Pro Asn Glu Gly
225                 230                 235                 240 ggt aca cct cca aaa aga tgc cgt gat gat ggt tct aca cct cat caa      768
Gly Thr Pro Pro Lys Arg Cys Arg Asp Asp Gly Ser Thr Pro His Gln
                245                 250                 255 gaa atg aca act acc acc act acc acc acc act act att cat aac          816
Glu Met Thr Thr Thr Thr Thr Thr Thr Thr Thr Thr Ile His Asn
            260                 265                 270 tct cga gct cag aac cag gac ccg cca cgt gtc tca ctt cac cgc cag      864
Ser Arg Ala Gln Asn Gln Asp Pro Pro Arg Val Ser Leu His Arg Gln
        275                 280                 285 ctc acc cgc agg agc ttg agc tgt gga agt att cca tca tgc gat caa      912
Leu Thr Arg Arg Ser Leu Ser Cys Gly Ser Ile Pro Ser Cys Asp Gln
    290                 295                 300 aca cca gga caa acc aca aat aac atc ggc ctc ggc atg tcg tcc gcc      960
Thr Pro Gly Gln Thr Thr Asn Asn Ile Gly Leu Gly Met Ser Ser Ala
305                 310                 315                 320 att ctc acc aaa agc aca ctt gat atc cga acc ctg aaa cgt ggc acg     1008
Ile Leu Thr Lys Ser Thr Leu Asp Ile Arg Thr Leu Lys Arg Gly Thr
                325                 330                 335 ccg gcg tgg act aat gga aca act cgt gac atc gca atg aga cca cac     1056
Pro Ala Trp Thr Asn Gly Thr Thr Arg Asp Ile Ala Met Arg Pro His
        340                 345                 350 acg ttt ata gag gca gga atc aaa gcg atg cga aaa tgc gac aaa tgt     1104
Thr Phe Ile Glu Ala Gly Ile Lys Ala Met Arg Lys Cys Asp Lys Cys
    355                 360                 365 gct aca gcc ctg aag ctc gcc aca tca atg aaa tgc aga gac tgt cac     1152
Ala Thr Ala Leu Lys Leu Ala Thr Ser Met Lys Cys Arg Asp Cys His
370                 375                 380 cag gtt gtc cat cgt agt tgc tgc aac aaa ctt cat ctc ccg tgc ata     1200
Gln Val Val His Arg Ser Cys Cys Asn Lys Leu His Leu Pro Cys Ile
                385                 390                 395                 400 cca cgc ccc aag acg atg atg acg ccg aaa tcc gca tta cgt gga gcc     1248
Pro Arg Pro Lys Thr Met Met Thr Pro Lys Ser Ala Leu Arg Gly Ala
        405                 410                 415 aag ccg ggc gca gga gag ttc cga ctt caa gat ttg tgc aca tct gcg     1296
Lys Pro Gly Ala Gly Glu Phe Arg Leu Gln Asp Leu Cys Thr Ser Ala
    420                 425                 430 aag cca atg atc ccg gca gca gtt att cat tgt gtg gtt gcc ctg gag     1344
Lys Pro Met Ile Pro Ala Ala Val Ile His Cys Val Val Ala Leu Glu
435                 440                 445 gct cgt gga ctc acg cag gaa ggt att tac cgc gtt cct ggg cag gtt     1392
Ala Arg Gly Leu Thr Gln Glu Gly Ile Tyr Arg Val Pro Gly Gln Val
                450                 455                 460 aga act gtc aat gtg ctt ttg gac gag ttg aga tca aaa acg gta ccc     1440
Arg Thr Val Asn Val Leu Leu Asp Glu Leu Arg Ser Lys Thr Val Pro
465                 470                 475                 480 aac gtg ggc ctt cac gac gtt gag gtc atc aca gac acc ttg aaa cgg     1488
Asn Val Gly Leu His Asp Val Glu Val Ile Thr Asp Thr Leu Lys Arg
```

-continued

```
                        485                 490                 495
ttc cta aga gat ctt aaa gac ccg ttg atc cca aga acg tct cgt caa         1536
Phe Leu Arg Asp Leu Lys Asp Pro Leu Ile Pro Arg Thr Ser Arg Gln
            500                 505                 510 gag ctc atc gtt gct gca aac ctc tac tct acg gat cca gat aat gga         1584
Glu Leu Ile Val Ala Ala Asn Leu Tyr Ser Thr Asp Pro Asp Asn Gly
        515                 520                 525 cgt ctc gcc ctg aat cga gtg atc tgt gag ctc ccc caa gcg aat cga         1632
Arg Leu Ala Leu Asn Arg Val Ile Cys Glu Leu Pro Gln Ala Asn Arg
    530                 535                 540 gac acc ctc gcc tac ctt ttc att cac tgg cgc aaa gtt atc gca caa         1680
Asp Thr Leu Ala Tyr Leu Phe Ile His Trp Arg Lys Val Ile Ala Gln
545                 550                 555                 560 tcg agt cgc aac aag atg aac tgc gaa gcg atg gcg cgg atg gtg gct         1728
Ser Ser Arg Asn Lys Met Asn Cys Glu Ala Met Ala Arg Met Val Ala
                565                 570                 575 ccg gcg gtg atg ggt cat cca gtg aag caa tcg cag tcc caa gcg ata         1776
Pro Ala Val Met Gly His Pro Val Lys Gln Ser Gln Ser Gln Ala Ile
            580                 585                 590 gct ggc aga gat gcc acg gat tgc cat cga gcg atg act gct cta ttt         1824
Ala Gly Arg Asp Ala Thr Asp Cys His Arg Ala Met Thr Ala Leu Phe
        595                 600                 605 gaa ttt gat gat gta tat tgg caa cga ttc cta ggg aca tct gca gtt         1872
Glu Phe Asp Asp Val Tyr Trp Gln Arg Phe Leu Gly Thr Ser Ala Val
    610                 615                 620 tcc atg gct tct aat caa att gaa acg gct cga cat cag gac aat ttt         1920
Ser Met Ala Ser Asn Gln Ile Glu Thr Ala Arg His Gln Asp Asn Phe
625                 630                 635                 640 gct ctc tgt gat cgt agc atc ctt gga cca gtt aca aca tca cca gcc         1968
Ala Leu Cys Asp Arg Ser Ile Leu Gly Pro Val Thr Thr Ser Pro Ala
                645                 650                 655 act ccc ctg ctt gct cgg tcg gcc aac gcg act cga gca cgt ggt gct         2016
Thr Pro Leu Leu Ala Arg Ser Ala Asn Ala Thr Arg Ala Arg Gly Ala
            660                 665                 670 cat ctg ctg ggg tcg atg ttc cac gat tag                                 2046
His Leu Leu Gly Ser Met Phe His Asp
        675                 680

<210> SEQ ID NO 6
<211> LENGTH: 681
<212> TYPE: PRT
<213> ORGANISM: Caenorhabditis elegans

<400> SEQUENCE: 6

Met Lys Ser Ser Thr Ser Lys Glu Lys Val Cys Gly Glu Asn Ser Arg
  1               5                  10                  15

His Ile Phe Asn Met Ile Leu Asn Ser Gln Arg Pro Gln Phe Asp Ile
             20                  25                  30

Lys Asp Ile Gly Met Phe His Leu Ile Asp Glu Ile Glu Arg Leu Arg
         35                  40                  45

Lys Leu Trp Lys Asp Ser Glu Glu Ser Lys Lys Arg Leu Asn Ala Asp
     50                  55                  60

Met Arg Glu Ala Glu Glu Ala Leu Ala Lys Ala Arg Lys Lys Leu Ala
 65                  70                  75                  80

Met Phe Asp Ile Asp Val Lys Asp Thr Gln Lys His Leu Arg Ala Leu
                 85                  90                  95

Met Glu Glu Asn Lys Ala Leu Lys Leu Asp Leu Asn Val Tyr Glu Thr
            100                 105                 110
```

```
Arg Glu Lys Gln Leu Lys Asp Ala Met Lys Asn Gly Ile Phe Asn Ser
        115                 120                 125
Leu Thr Lys Glu Asp Arg Asp Gln Phe Lys Phe Leu His Glu Pro Leu
    130                 135                 140
Val Arg Thr Tyr Ser Lys Arg Val Gln Gln Arg His Pro His Leu Met
145                 150                 155                 160
Glu Asp Thr Gln Asp Asp Glu Asp Ser Glu Val Asp Tyr Asp Glu
                165                 170                 175
Thr Gly Asp Ser Phe Glu Glu Val Ile His Leu Arg Asn Gly Arg Glu
            180                 185                 190
Val Arg Arg Ser Ser Ala Ala Gly Asn Ala Val Gly Lys Arg Arg
        195                 200                 205
Ser Ala Ser Ala His Ala Ile Thr Ala Ala Asn Ser Lys Arg Ser
    210                 215                 220
Arg Ser Arg Val Met Thr Ala Thr Ile Asp Glu Glu Pro Asn Glu Gly
225                 230                 235                 240
Gly Thr Pro Pro Lys Arg Cys Arg Asp Asp Gly Ser Thr Pro His Gln
                245                 250                 255
Glu Met Thr Thr Thr Thr Thr Thr Thr Thr Thr Thr Ile His Asn
            260                 265                 270
Ser Arg Ala Gln Asn Gln Asp Pro Pro Arg Val Ser Leu His Arg Gln
        275                 280                 285
Leu Thr Arg Arg Ser Leu Ser Cys Gly Ser Ile Pro Ser Cys Asp Gln
    290                 295                 300
Thr Pro Gly Gln Thr Thr Asn Asn Ile Gly Leu Gly Met Ser Ser Ala
305                 310                 315                 320
Ile Leu Thr Lys Ser Thr Leu Asp Ile Arg Thr Leu Lys Arg Gly Thr
                325                 330                 335
Pro Ala Trp Thr Asn Gly Thr Thr Arg Asp Ile Ala Met Arg Pro His
            340                 345                 350
Thr Phe Ile Glu Ala Gly Ile Lys Ala Met Arg Lys Cys Asp Lys Cys
        355                 360                 365
Ala Thr Ala Leu Lys Leu Ala Thr Ser Met Lys Cys Arg Asp Cys His
    370                 375                 380
Gln Val Val His Arg Ser Cys Cys Asn Lys Leu His Leu Pro Cys Ile
385                 390                 395                 400
Pro Arg Pro Lys Thr Met Met Thr Pro Lys Ser Ala Leu Arg Gly Ala
                405                 410                 415
Lys Pro Gly Ala Gly Glu Phe Arg Leu Gln Asp Leu Cys Thr Ser Ala
            420                 425                 430
Lys Pro Met Ile Pro Ala Ala Val Ile His Cys Val Val Ala Leu Glu
        435                 440                 445
Ala Arg Gly Leu Thr Gln Glu Gly Ile Tyr Arg Val Pro Gly Gln Val
    450                 455                 460
Arg Thr Val Asn Val Leu Leu Asp Glu Leu Arg Ser Lys Thr Val Pro
465                 470                 475                 480
Asn Val Gly Leu His Asp Val Glu Val Ile Thr Asp Thr Leu Lys Arg
                485                 490                 495
Phe Leu Arg Asp Leu Lys Asp Pro Leu Ile Pro Arg Thr Ser Arg Gln
            500                 505                 510
Glu Leu Ile Val Ala Ala Asn Leu Tyr Ser Thr Asp Pro Asp Asn Gly
        515                 520                 525
Arg Leu Ala Leu Asn Arg Val Ile Cys Glu Leu Pro Gln Ala Asn Arg
```

-continued

```
                    530                 535                 540
Asp Thr Leu Ala Tyr Leu Phe Ile His Trp Arg Lys Val Ile Ala Gln
545                 550                 555                 560

Ser Ser Arg Asn Lys Met Asn Cys Glu Ala Met Ala Arg Met Val Ala
                    565                 570                 575

Pro Ala Val Met Gly His Pro Val Lys Gln Ser Gln Ser Gln Ala Ile
                    580                 585                 590

Ala Gly Arg Asp Ala Thr Asp Cys His Arg Ala Met Thr Ala Leu Phe
                595                 600                 605

Glu Phe Asp Asp Val Tyr Trp Gln Arg Phe Leu Gly Thr Ser Ala Val
                610                 615                 620

Ser Met Ala Ser Asn Gln Ile Glu Thr Ala Arg His Gln Asp Asn Phe
625                 630                 635                 640

Ala Leu Cys Asp Arg Ser Ile Leu Gly Pro Val Thr Thr Ser Pro Ala
                645                 650                 655

Thr Pro Leu Leu Ala Arg Ser Ala Asn Ala Thr Arg Ala Arg Gly Ala
                660                 665                 670

His Leu Leu Gly Ser Met Phe His Asp
                675                 680
```

METHODS FOR IDENTIFYING INHIBITORS OF CYTOKINESIS USING CYK-4 PROTEINS

The present application claims the benefit, under 35 U.S.C. § 119, of the earlier filing dates of European Patent Application No. EP 00 112 880.0, filed Jun. 19, 2000; European Patent Application No. EP 01 110 554.1, filed Apr. 30, 2001; U.S. Provisional Application No. 60/241,231, filed Oct. 18, 2000; and U.S. Provisional Application No. 60/297,434, filed Jun. 13, 2001. The contents of each of these applications are entirely incorporated herein by reference.

The present invention relates to a new protein Cyk-4, which is involved in cytokinesis, to its use in screening assays, and to therapies interfering with cell division, in particular tumor therapy.

The process of cytokinesis produces two daughter cells from a single parental cell and permanently segregates the products of the cell division cycle. Cytokinesis is one of the few processes in biology known to require coordination between microtubules and actin filaments. Indeed, in animal cells there are two steps in cytokinesis that rely on interactions between microtubules and the actin-based contractile ring (for review see (Field et al., 1999; Glotzer, 1997). In the first instance, the microtubule-based mitotic spindle specifies the position of the contractile ring. This allows the division plane to be positioned so that the separated chromosomes are partitioned equally into the two daughter cells. Subsequently, after ingression of the cleavage furrow, there is a second step that depends on both microtubules and the contractile ring. Completion of cytokinesis requires the central spindle, which contains bundled, antiparallel microtubules. The molecular mechanisms underlying these two microtubule dependent steps in cytokinesis are not known.

The degree to which the progression of cytokinesis depends on the central spindle varies somewhat in different experimental organisms. In invertebrate embryos, a transient interaction between astral microtubules of the mitotic spindle and the cell cortex is sufficient to position the cleavage furrow (Rappaport, 1985). Furrows specified in this manner ingress, but if the spindle is removed, these furrows do not usually complete cytokinesis (Rappaport, 1985). In contrast, in *Drosophila* spermatocytes, contractile ring formation requires the central spindle (Giansanti et al., 1998). Similarly, in cultured mammalian cells, astral microtubules appear to be insufficient to induce furrow ingression, instead the presence or absence of a central spindle determines whether or not a cleavage furrow forms (Cao and Wang, 1996; Eckley et al., 1997; Rieder et al., 1997; Savoian et al., 1999; Wheatley and Wang, 1996). Moreover, in cultured cells, the central spindle is also required for completion of cytokinesis (Wheatley and Wang, 1996). In *C. elegans* embryos, as in invertebrate embryos, only the later stages of cytokinesis appear to depend on the central spindle. Embryos depleted of the kinesin-like protein ZEN-4/CeMKlp1 fail to assemble the central spindle, yet cleavage furrows form and ingress, but cytokinesis does not proceed to completion (Powers et al., 1998; Raich et al., 1998). In summary, the initiation of cytokinesis depends on the central spindle in some but not in all organisms, whereas there appears to be a general requirement for the central spindle for the completion of cytokinesis in animal cells. While it is clear that the central spindle plays an important role in cytokinesis the underlying mechanism remains elusive.

Cleavage furrow ingression is driven by the actin-based contractile ring. Like many actin-based structures, the contractile ring requires the RhoA GTPase for its assembly. Rho family GTPases are thought to act as molecular switches that cycle between inactive GDP-bound forms and active GTP-bound forms; their ability to exchange and hydrolyze GTP is regulated by additional factors, the so-called guanine nucleotide exchange factors (GEFs) and GTPase activating proteins (GAPs). Inactivation of RhoA by the exoenzyme C3 (Aktories and Hall, 1989), inhibits cytokinesis in a wide variety of experimental settings by causing disassembly of cortical actin structures and the contractile ring (Drechsel et al., 1997; Kishi et al., 1993; Mabuchi et al., 1993; Moorman et al., 1996; O'Connell et al., 1999). Further, a Rho GEF is essential for cytokinesis (Prokopenko et al., 1999; Tatsumoto et al., 1999). GTP-bound RhoA interacts with a number of putative effectors including formins, Rho Kinase, Citron kinase, and a regulatory subunit of myosin phosphatase (for review see (Van Aelst and D'Souza-Schorey, 1997). The requirement for RhoA in cytokinesis may reflect its ability to regulate formins since members of the formin gene family are required for cytokinesis in budding yeast (BNI1/BNR1) (Imamura et al., 1997), fission yeast (Cdc12) (Chang et al., 1997), *Drosophila* (dia) (Castrillon and Wasserman, 1994) and *C. elegans* (cyk-1) (Swan et al., 1998). Several formins also bind to profilin (Chang et al., 1997 ; Evangelista et al., 1997; Imamura et al., 1997; Watanabe et al., 1997), a key regulator of actin polymerization. It is conceivable that GTP-bound RhoA promotes contractile ring assembly by activating actin polymerization via the formins and by activating myosin motor activity.

There is compelling evidence that the microtubule-based central spindle and the actin-based cleavage furrow are both essential for cytokinesis. Nest, the question was asked how these two cytoskeletal polymers interact. There are a few cases in which an interaction between the microtubule and actin cytoskeletal systems have been characterized. Examples include nuclear positioning in budding yeast (Carminati and Stearns, 1997; Fujiwara et al., 1999; Miller et al., 1999), spindle orientation in epithelial cells (Busson et al., 1998) and in certain asymmetrically dividing cells, such as the posterior blastomere of the two cell *C. elegans* embryo (Gönczy et al., 1999a; Hyman and White, 1987; Skop and White, 1998; Waddle et al., 1994). In these examples there is evidence that the dynein/dynactin microtubule motor complex may mediate the interaction of microtubules with the cell cortex.

It was an object of the invention to elucidate the microtubule dependent steps in cytokinesis. In particular, it was sought to define the role of the central spindle in this process, in order to be able to interfere with this process and thus with cytokinesis, which provides a new approach for therapy, in particular cancer therapy.

Therefore, to solve the problem underlying the invention, it was investigated how the central spindle assembles and how it functions in cytokinesis.

In the present invention, a novel gene designated cyk-4 was identified and cloned and its role in the early divisions of the *C. elegans* embryo was characterized.

It was shown that Cyk-4 is required for the late stages of cytokinesis. Interestingly, cyk-4 mutant embryos fail to assemble the central spindle. Positional cloning and localization studies revealed that the cyk-4 gene encodes a novel GTPase activating protein (GAP) for the Rho family of GTPases that localizes to the central spindle. The missense mutation in the cyk-4(t1689ts) allele is found in a domain dispensable for GAP activity suggesting that Cyk-4 may have another function in addition to activating GTP hydrolysis by Rho family proteins. Accordingly, it was found that Cyk-4 and the kinesin-like protein Zen-4/CeMKlp1 are interdependent for their proper localization. Based on these data, a model is proposed by which Cyk-4 acts in concert with Zen-4/CeMKlp1 to assemble the central spindle. The concentration of Cyk-4 to the central spindle would then serve to target the GAP domain to the fully ingressed contractile ring where it could promote GTP hydrolysis by RhoA, thereby facilitating the completion of cytokinesis.

In further experiments, the biochemical state of CYK-4 and ZEN-4 has been examined and it was found that they do indeed associate in vivo. These proteins also efficiently associate in vitro and an in vitro binding assay has been used to molecularly dissect the regions of both proteins that are necessary and sufficient for this interaction. It is shown that the protein encoded by the ts allele cyk-4(t1689) is defective in binding to ZEN-4. The identification of mutations in zen-4 that partially rescue cyk-4(t1689) and map to the CYK-4 binding region provides strong evidence for the importance of the interaction between CYK-4 and ZEN-4 for progression of cytokinesis. It has also been shown that the human orthologs of CYK-4 and ZEN-4, HsCYK-4/MgcRacGAP and MKLP1, are in a complex which has been purified. The complex contains approximately stoichiometric amounts of HsCYK-4 and MKLP1. The human complex localizes to the central spindle and to division remnants, as do the nematode proteins. Thus, in the present invention, an evolutionarily conserved complex that is essential for central spindle assembly has been identified.

The division of a cell into two daughters requires dynamic interactions between the microtubule-based mitotic spindle and the actin-based contractile ring. In animal cells the position of the cleavage furrow, an actomyosin-based structure, is determined by the mitotic spindle in a manner that is poorly understood. In recent years is has become clear that the central spindle, an array of microtubule bundles that forms during anaphase, also plays an important role in cytokinesis. To gain insight into this fundamental cellular process, the cytokinesis-defective mutant, cyk-4, was analyzed. Cytological analysis reveals that cyk-4 mutant embryos fail to assemble the central spindle. Though lacking a central spindle, cyk-4 mutant embryos furrow extensively, but they fail to complete cytokinesis. The mutation responsible for the cyk-4 phenotype was found to be a missense mutation in a gene encoding a Rho family GAP that, in vitro, stimulates GTP hydrolysis by Rho, Rac, and Cdc42. CYK-4 localizes to the central spindle and to cell division remnants. CYK-4 colocalizes with the ZEN-4/CeMKLP1 kinesin-like protein. Moreover, CYK-4 and ZEN-4/CeMKLP1 are interdependent for their localization. It is concluded that the CYK-4 GAP and the ZEN-4/CeMKLP1 kinesin-like protein cooperate to assemble the central spindle. Furthermore, it is proposed that a concentrated source of CYK-4 GAP on the central spindle could downregulate the RhoA GTPase and thereby promote the late stages of cytokinesis. The findings of the present invention provide a model for CYK-4 dependent assembly of the central spindle:

In cyk-4 mutant embryos the robust microtubule bundles that constitute the central spindle do not form. Instead, the spindle develops into two mitotic asters separated by a few overlapping, disorganized, microtubules. A similar phenotype is observed in zen-4 mutant embryos (Powers et al., 1998; Raich et al., 1998). Thus both the ZEN-4/CeMKLP1 kinesin-like protein and the CYK-4 GAP are essential for this microtubule bundling. The *Drosophila* orthologue of ZEN-4/CeMKLP1 is also required for cytokinesis, though it seems to be required for all aspects of furrow ingression (Adams et al., 1998). Members of the MKLP1 subfamily of kinesin-like proteins have microtubule bundling activity in vitro (Kuriyama et al., 1994; Nislow et al., 1992). However, in vivo, ZEN-4 mediated microtubule bundling requires CYK-4.

In answering the question how CYK-4 and ZEN-4 could cooperate to assemble the central spindle, it is proposed that a complex containing multiple motor proteins could specifically localize to overlapping, antiparallel microtubules (FIG. 10). If such a motor complex transits along a microtubule it might continue to an end and dissociate. However, if such a motor complex transited along a microtubule in the vicinity of an antiparallel microtubule, the complex might bind simultaneously to both microtubules and attempt to move alternately in opposite directions, the net result being that the complex would concentrate in the region of microtubule overlap. Since CYK-4 does not have a microtubule motor domain, yet it is essential for the formation of the central spindle, it is proposed that CYK-4 forms a complex with multiple ZEN-4 homodimers that localizes to and stabilizes overlapping antiparallel microtubules (FIG. 10).

It was of interest to find out if the RhoGAP activity of CYK-4 necessary to promote microtubule bundling by ZEN-4. It is proposed that central spindle assembly is unlikely to require CYK-4 GAP activity. This is suggested by two lines of evidence. First, central spindle assembly is defective in the cyk-4(t1689ts) allele that carries a missense mutation at amino acid 15. This substitution is distant from the C-terminal GAP domain, and in vitro, the amino terminus of CYK-4 is dispensable for GAP activity. Thus this allele would be predicted to retain catalytic activity in vivo and therefore GAP activity is not sufficient for central spindle assembly. Moreover, Rho RNAi experiments reveal that central spindle assembly is Rho independent, suggesting that Rho GAP activity is not required for this process. Thus CYK-4 may act to promote central spindle assembly, independent of its GAP activity.

In the present invention, the function of the CYK-4 gap domain was analysed:

If CYK-4 function in central spindle assembly is independent of the Rho GTPase, it was of interest to determine the function of the CYK-4 GAP domain. CYK-4 is likely bifunctional, one function being to promote the assembly of the central spindle, the second function being to promote GTP hydrolysis by Rho family members. These two functions might be related in that the first function would serve to concentrate CYK-4 at a site where GAP activity is required. It may be assumed that CYK-4 GAP activity is required late in cytokinesis, to promote GTP hydrolysis by a Rho family GTPase whose downregulation causes disassembly of the contractile ring and cell separation (FIG. 10).

It was determined which GTPase might CYK-4 act on to promote cytokinesis. The CYK-4 GAP domain has all the hallmarks of a Rho family GAP and it may therefore be expected that it will act on this subfamily of the GTPase superfamily. Like many other RhoGAPs, the GAP domain of CYK-4 is promiscuous in its ability to promote GTP hydrolysis on Rho, Rac, and Cdc42 (Lamarche and Hall, 1994). The strongest piece of evidence that CYK-4 acts on Rho is based on the observation that of the GTPases tested, Rho is the only one that is clearly essential for cytokinesis. The requirement for Rho in cell division is well documented in a variety of experimental systems. To date there is no evidence that Rac is required for cytokinesis and the data using RNAi to deplete Rac also failed to detect a role for this GTPase in this process. Moreover, it has been recently reported that ced-10 mutants, which are defective in corpse engulfment subsequent to apoptosis and distal tip cell migration, contain mutations in the rac gene (Reddien and Horvitz, 2000). ced-10 mutants do not have any gross phenotypes indicative of a role in cytokinesis. Moreover, Rac1 deficient mice are gastrulation defective, but the embryos do not contain multinucleate cells indicative of a cell division defect (Sugihara et al., 1998). The sum of these data argue that Rac is not an essential target of CYK-4 during cytokinesis. With regard to Cdc42, previous studies have implicated this GTPase in cytokinesis (Drechsel et al., 1997; Dutartre et al., 1996). Superficially, the weakly penetrant cytokinesis phenotype observed in Cdc42(RNAi) embryos is consistent with these earlier data. However the Cdc42 (RNAi) embryos that are cytokinesis defective are also osmotically swollen and therefore cytokinesis defect may be indirect. Thus at this juncture it appears most likely that RhoA is the key substrate for the CYK-4 GAP activity.

Further support for the hypothesis that completion of cytokinesis requires downregulation of RhoA by CYK-4 would be supported by experiments in which the cyk-4 phenotype is phenocopied by RhoA mutants that are hydrolysis defective. However the genetic tools necessary to express such dominant mutants in the early *C. elegans* embryo are currently unavailable. It is surprising that the CYK-4 GAP domain is less active towards RhoA as compared to Rac or Cdc42, if indeed RhoA is the relevant target of its GAP activity. One possible explanation is that full length CYK-4 has a different activity profile as compared to the isolated GAP domain. A more interesting possibility is that CYK-4 localization is important for CYK-4 GAP activity. The phenotype of cyk-4 mutant embryos suggests that CYK-4 needs to act when the contractile ring is in close proximity to the central spindle. Since CYK-4 is concentrated on the central spindle at this time, its high local concentration might overcome its lower activity towards RhoA.

In the present invention, the central spindle was shown to be at the center of cytokinesis:

There appear to be at least two microtubule-dependent steps in cytokinesis, contractile ring positioning and completion of cytokinesis. In some cells both processes are dependent on the central spindle. An important open question is whether these two reactions are mechanistically similar. While assembly of the contractile ring requires activation of RhoA, it was previously shown that the position of the contractile ring is specified in a RhoA-independent manner in *Xenopus embryos* (Drechsel et al., 1997). It has been shown here that a Rho GAP is required for the late stages of cytokinesis, suggesting that the second process, completion of cytokinesis, does involve RhoA. It is therefore assumed that the two microtubule-dependent steps in cytokinesis are distinct.

CYK-4 and ZEN-4 are not the only components of the central spindle, a number of other components, some of which are required for cytokinesis, are also present at this site. Polo kinase is known to associate with MKLP1 and to concentrate in the central spindle (Adams et al., 1998; Lee et al., 1995), and this kinase is essential for cytokinesis. Rho associated kinase also localizes to this site (Kosako et al., 1999). The AIR-2 aurora-like kinase localizes to the central spindle (Schumacher et al., 1998). This kinase seems to be required primarily for chromosome segregation (Woollard and Hodgkin, 1999), its direct involvement in cytokinesis requires further analysis. INCENP and the TD-60 antigen also localize to the central spindle and there is evidence that they may play a role in cytokinesis (Eckley et al., 1997; Mackay et al., 1998; Martineau-Thuillier et al., 1998; Savoian et al., 1999). Interestingly, a Rho GEF that is required for cytokinesis, ECT2, also accumulates on the central spindle (Tatsumoto et al., 1999), however the *Drosophila* ortholog, Pebble, does not localize in this manner (Prokopenko et al., 1999).

Further analysis of the specific functions of all of these cytokinesis regulators is the basis to determine which of these proteins are functionally interdependent as has been shown is the case for Cyk-4 and Zen-4/CeMKlp1.

Furthermore, it was shown that the central spindle is a structure that is essential for completion of cytokinesis. Two proteins required for central spindle assembly, CYK-4 and ZEN-4, were shown to co-localize to the central spindle and to somehow act in concert with one another. In experiments of the present invention, it was demonstrated that in vivo, CYK-4 and ZEN-4 are present in an evolutionarily conserved protein complex and the nature of this complex in *C. elegans* embryos and in human cells was characterized in detail. These data suggest that the CYK-4/ZEN-4 complex, which was named centralspindlin, consists of a two molecules each of CYK-4 and ZEN-4. CYK-4 binds to the neck region of the ZEN-4 kinesin, raising the possibility that the motor activity of the ZEN-4 is directly regulated by the CYK-4 RhoGAP.

Analytical biochemistry of the native centralspindlin complex isolated from *C. elegans* embryos demonstrates the existence of a complex containing the ZEN-4 kinesin and the CYK-4 RhoGAP. In vitro binding experiments were used to define the critical determinants for this interaction and to demonstrate that the two subunits are able to self associate. Genetic and biochemical suppression of the CYK-4 S15L mutation by a second site mutation in ZEN-4 strongly argues that the interaction between CYK-4 and ZEN-4 is critical for CYK-4 function. Indeed, in vivo, the majority of ZEN-4 is in a complex with CYK-4. Moreover, three lines of evidence indicate that HsCYK-4 and MKLP1 are in a tetrameric complex. First, immunopurification of HsCYK-4 and MKLP1 reveals equal amounts of the two proteins. Second, these two proteins co-migrate on sucrose density gradients with a similar S value as observed for the *C. elegans* proteins. Third, the two proteins precisely co-migrate on a gel filtration column and their fractionation behavior suggests a native molecular mass for the complex of ~300 kDa. Previous determinations of the native molecular mass of MKLP1 have been reported and the values are similar to those obtained in the present invention here (Chui et al., 2000; Kuriyama et al., 1994). Previous studies had not taken the presence of CYK-4 into consideration and therefore they interpreted their data to indicate that MKLP1 exists as a homotetramer. However, the data obtained in the experiments of the invention are not compatible with this interpretion, but they rather indicate that the centralspindlin complex is a tetramer containing two molecules of the kinesin ZEN-4/MKLP1 and two molecules of the RhoGAP CYK-4.

CYK-4 binds to ZEN-4 in a particularly interesting region of this kinesin family member. Rice et al., 1999 have established that a critical element of the kinesin molecule lies just C-terminal to the catalytic core; the neck linker region. ATP binding to one catalytic core induces a large scale conformational change in the neck linker region that causes the other catalytic core to extend towards the adjacent tubulin dimer situated on the plus side of the initial microtubule contact (Rice et al., 1999). In the present invention, it was found that CYK-4 binds to a region of ZEN-4 that includes the neck linker region. In conventional kinesin, the neck linker region corresponds to a region 15 amino acids long that connects the catalytic core of kinesin to the coiled coil stalk domain. Among the family of KIN-N motors, the MKLP1 subfamily has a distinctly divergent neck linker region, it lacks several nearly invariant residues and the linker between the catalytic core and the coiled coil region is about 5 times longer than in other members on the KIN-N family. The divergence of this critical region of the kinesin suggests that MKLP1-mediated microtubule motility may differ from that of other kinesins. Moreover, since CYK-4 binds to the neck linker region of ZEN-4 it is possible that CYK-4 binding may in fact regulate ZEN-4 motor activity.

Previous work had suggested that MKLP1 may exist as a tetramer containing 4 motor domains (Chui et al., 2000; Kuriyama et al., 1994). If the two dimers were arranged in an antiparallel orientation, this arrangement could easily explain how this complex could crosslink antiparallel microtubules. However, the data obtained in the present invention are not consistent with this proposed structure. The complex that has been characterized appears to contain two kinesin motors and two RhoGAP molecules. Since most kinesin motors are dimers in which both catalytic cores interact with a single microtubule protofilament, the architecture that is described here can not easily explain how microtubule bundling is achieved. If the two kinesin subunits of centralspindlin bind to the same microtubule protofilament, then how might microtubule crosslinking occur? At this point, at least three possible mechanisms can be envisaged (FIG. 18).

The first possibility is that there is an additional microtubule binding site elsewhere in the CYK-4/ZEN-4 complex. No additional binding site has been identified yet in CYK-4 nor has MKLP1, ZEN-4, or Pav been found to have an additional microtubule binding site. However, it has been shown, and was confirmed by the inventors, that MKLP1 interacts differently with microtubules than most kinesin-like proteins. Specifically, ATP is usually sufficient to elute most kinesins from microtubules, but in the case of MKLP1, both ATP and high salt are required (Kuriyama et al., 1994; Nislow et al., 1992). Thus it is possible that MKLP1 interacts with two microtubules, one by the motor domain and another via a different interaction surface. Consistent with this possibility is the finding that Rab6KIFL kinesin, which is quite similar to MKLP1 in primary structure as well as in its localization and proposed function (Fontijn et al., 2001; Hill et al., 2000), has been reported to contain a second microtubule binding activity in the C-terminal half of the molecule (Echard et al., 1998). However this possibility does not explain why CYK-4 is required for central spindle assembly.

The second alternative is that MKLP1 forms higher order structures and that the tetramer that has been characterized in the present invention is merely a building block. This possibility gains some support from localization studies. In both *C. elegans* and in mammalian cells, ring-like structures are found that are termed division remnants that persist in the cell cortex after division. These remnants appear to be large aggregates of centralspindlin which are not in direct association with microtubules. Higher order oligomers could potentially form in early anaphase and promote microtubule bundling.

The third possibility is that, unlike most N-terminal kinesins, the two catalytic cores of the kinesin subunits in the centralspindlin complex could bind to different microtubules. This would not be without precedent in that the KIN-N KIF1A moves processively along a microtubule using a single head (Okada and Hirokawa, 2000). The association of the two catalytic cores of MKLP1 with different microtubules is made feasible by the fact that the linker region between the catalytic core and the coiled coil domain is much longer than that present in most N-terminal kinesins. Perhaps CYK-4 ensures that the two motor domains are oriented in such a way to bind to antiparallel microtubules (FIG. 18). Structural analysis and biochemical reconstitution of centralspindlin from purified components will allow further insight into mechanism of antiparallel microtubule bundling.

One critical question, which has not be rigorously explored to date is the function of the central spindle during the process of cytokinesis. The obtained data do not shed extensive new light on this question. However, it may be noted that the RhoGAP domain of CYK-4 is highly conserved at the primary sequence level. Interestingly CYK-4 is significantly less active at inducing GTP hydrolysis by RhoA as compared to Rac and Cdc42 (Jantsch-Plunger et al., 2000), and this feature of CYK-4 is conserved in HsCYK-4 (Toure et al., 1998). It has been proposed by the inventors that one function of the central spindle is to concentrate CYK-4 to a position in the cell where it could promote inactivation of RhoA at a late stage in cytokinesis. Consistent with this model, inactivation of RhoA by RNAi does not prevent CYK-4 localization nor does it impair central spindle assembly. In addition, the RhoGAP domain seems to be required at some stage of cytokinesis, since overexpression of a HsCYK-4/MgcRacGAP bearing a mutation in the RhoGAP domain causes cytokinesis defects (Hirose et al., 2001). Further structure-function analysis of CYK-4 is necessary to test this model further. However such analyses must take into consideration that CYK-4 is able to dimerize or oligomerize and therefore such analysis is best done in the absence of endogenous CYK-4.

Although centralspindlin appears to be a simple tetrameric complex, there are several lines of evidence that suggest that it may be subject to regulation by at least two different kinases. Genetic analysis of Polo kinase in *Drosophila* indicates Pav localization is Polo dependent (Carmena et al., 1998) and moreover a biochemical interaction between Polo and MKLP1 orthologs have been shown in extracts from both mammalian cell and *Drosophila* embryos (Adams et al., 1998; Lee et al., 1995). In addition, the Aurora-B/Incenp complex is also required for the stable localization of centralspindlin in *C. elegans* embryos (Kaitna et al., 2000; Schumacher et al., 1998; Severson et al., 2000) and an in vitro biochemical interaction has been detected between Aurora-B (AIR-2) and ZEN-4 (Severson et al., 2000).

A stable association between Polo kinase or Aurora-B kinase with centralspindlin has not been observed. Reconstitution of central spindle assembly in vitro will allow the role of these and other regulators of centralspindlin to be dissected.

In summary, the experiments of the present invention comprise an initial phenotypic, molecular, biochemical, and cell biological analysis of the cyk-4 gene. Furthermore, they comprise an analysis of the CYK-4/ZEN-4 complex (centralspindlin) that consists of two molecules of each CYK-4 and ZEN-4.

The experiments of the present invention (Examples 1–5) indicate that Cyk-4 is an active GTPase activating protein that is required for cytokinesis, likely by its ability to regulate the RhoA GTPase. Quite surprisingly, one additional function of this protein is to promote assembly of the central spindle. Cyk-4 is a key molecule required for cytokinesis that regulates both the structure of the late mitotic spindle and the function of the contractile ring.

Thus, in a first aspect, the present invention generally relates to Cyk-4 polypeptides, which have been shown to be essential for this second microtubule dependent step and thus define a functional link between the central spindle and the contractile ring.

In a preferred embodiment, the invention relates to a mammalian Cyk-4 polypeptide, in particular murine and human Cyk-4.

In a first aspect, the invention relates to the murine Cyk-4 polypeptide with the amino acid sequence as set forth in SEQ ID NO:4 or with the amino acid sequence encoded by a polynucleotide which hybridizes under stringent conditions to a polynucleotide having a nucleotide sequence as set forth in SEQ ID NO:3.

In a preferred aspect, the invention relates to the human Cyk-4 polypeptide with the amino acid sequence as set forth in SEQ ID NO:2 or with the amino acid sequence encoded by a polynucleotide which hybridizes under stringent conditions to a polynucleotide having a nucleotide sequence as set forth in SEQ ID NO:1.

In a further aspect, the present invention relates to an isolated DNA molecule comprising a polynucleotide with the nucleotide sequence as set forth in SEQ ID NO:1 encoding human Cyk-4 polypeptide, or an isolated DNA molecule encoding human Cyk-4 polypeptide comprising a polynucleotide which hybridizes under stringent conditions to a polynucleotide having a nucleotide sequence as set forth in SEQ ID NO:1.

In a further aspect, the present invention relates to an isolated DNA molecule comprising a polynucleotide with the nucleotide sequence as set forth in SEQ ID NO:3 encoding murine Cyk-4 polypeptide, or an isolated DNA molecule encoding murine Cyk-4 polypeptide comprising a polynucleotide which hybridizes under stringent conditions to a polynucleotide having a nucleotide sequence as set forth in SEQ ID NO:3.

By "stringent hybridization conditions" as used herein is meant overnight incubation at 42° C. in a solution comprising: 50% formamide, 5× SSC (1× SSC 150 mM NaCl, 15 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1× SSC at about 65° C., or equivalent conditions.

In the following, if not otherwise stated, the term "Cyk-4" refers to both the murine and the human Cyk-4.

Homologues of the subject Cyk-4 polypeptides also include versions of the polypeptide which are resistant to post-translation modification or which alter the activity of the protein. Cyk-4 polypeptides may comprise a full length protein, such as represented in SEQ ID NO:2 or 4, or they may comprise fragments or variants therof.

Beside DNA molecules, the present invention relates to nucleic acid molecules in the form of RNA, such as mRNA. The DNA molecules include cDNA and genomic DNA obtained by cloning or produced synthetically. The DNA may be double-stranded or single-stranded. Single-stranded DNA or RNA may be the coding strand, also known as the sense (or plus) strand, or it may be the non-coding strand, also referred to as the antisense (or minus) strand. The present invention also relates to preparations of double stranded Cyk-4 RNA or derivatives thereof that can be used to interfere with gene expression by ds-RNA mediated gene interference as described by Fire et al. 1998 and reviewed by Fire, 1999; Bosher and Labouesse, 2000; Sharp, 1999.

By "isolated" nucleic acid molecule(s) is intended a nucleic acid molecule, DNA or RNA, which has been removed from its native environment. Recombinant DNA molecules contained in a vector are considered isolated for the purposes of the present invention. Further examples of isolated DNA molecules include recombinant DNA molecules maintained in heterologous host cells, and those DNA molecules purified (partially or substantially) from a solution whether produced by recombinant DNA or synthetic chemistry techniques. Isolated RNA molecules include in vivo or in vitro RNA transcripts of the DNA molecules of the present invention. However, it is intended that "isolated" as used herein does not include the Cyk-4 cDNA present in a cDNA library or in a preparation of purified or isolated genomic DNA containing the Cyk-4 gene or a portion thereof in admixture with one or more other cDNA molecules or DNA fragments.

The nucleic acid molecules of the present invention further include genetic constructs comprising one or more Cyk-4 DNA sequences operably linked to regulatory DNA sequences (which may be heterologous regulatory sequences), such as promoters or enhancers, wherein upon expression of these DNA sequences in host cells, preferably in bacterial, fungal (including yeast), plant or animal (including insect or mammalian) cells, one or more Cyk-4 polypeptides are produced. In such constructs, the design of which is described in laboratory manuals (see e.g. Sambrook et al., 2000) and is routine to the skilled artisan, the regulatory sequences may be operably linked to a Cyk-4 polynucleotide encoding mature Cyk-4 polypeptide or any of its variants, precursors, fragments or derivatives described herein, which may include one or more polynucleotides having a nucleic acid sequence that is complementary to substantially all or a portion of a nucleic acid molecule having a nucleic acid sequence as shown in SEQ ID NO:1 or 3. As used herein, the terms "a portion" or "a fragment" of a nucleic acid molecule or a polypeptide means a segment of a polynucleotide or a polypeptide comprising at least 15, and more preferably at least 20, contiguous nucleotides or amino acids of a reference polynucleotide or polypeptide (for example, the polynucleotide and polypeptide shown in SEQ ID NOs: 1 or 3, respectively, unless otherwise specifically defined below.)

Besides the DNA molecules having a nucleotide sequence corresponding to that depicted SEQ ID NO:1 or 3, the invention also relates to DNA molecules which comprise a sequence substantially different from those described above but which, due to the degeneracy of the genetic code, still encode the Cyk-4 mouse or human polypeptides. Since the genetic code is well known in the art, it is routine for one of ordinary skill in the art to produce the degenerate variants described above without undue experimentation.

In addition, the invention relates to Cyk-4 polypeptides which have deviations from the sequence shown in SEQ ID NO:2 or 4, caused by the conservative exchange of amino acids, if they are Cyk-4 derivatives or fragments or peptides with the properties which are desirable for their use in therapy or in screening assays, or isolated DNA molecules encoding such derivatitives or fragments with a polynucleotide sequence varying in their sequence from SEQ ID NO:1 or 3.

Nucleic acid molecules of the present invention which encode a Cyk-4 polypeptide or a derivative or fragment thereof may include, but are not limited to, those encoding the amino acid sequence of the polypeptide by itself, together with additional, non-coding sequences, including for example introns and non-coding 5' and 3' sequences, such as the transcribed, untranslated regions (UTRs) or other 5' flanking sequences that may play a role in transcription (e.g., via providing ribosome- or transcription factor-binding sites), mRNA processing (e.g. splicing and polyadenylation signals) and stability of mRNA; the coding sequence for the Cyk-4 polypeptide operably linked to a regulatory DNA sequence, particularly a heterologous regulatory DNA sequence such as a promoter or enhancer; and the coding sequence for the Cyk-4 polypeptide linked to one or more coding sequences which code for amino acids that provide additional functionalities. Thus, the sequence encoding the polypeptide may be fused to a marker sequence, such as a sequence encoding a peptide which facilitates purification of the fused polypeptide. In certain embodiments of this aspect of the invention, the marker amino acid sequence may be a hexa-histidine peptide, such as the tag provided in a pQE vector (Qiagen, Inc.), among others, many of which are commercially available. As described for instance in Gentz et al., 1989, hexa-histidine provides for convenient purification of the fusion protein. The "HA" tag is another peptide useful for purification which corresponds to an epitope derived from the influenza hemagglutinin protein, which has been described by Wilson et al., 1984. Yet another useful marker peptide for facilitation of purification of Cyk-4 is glutathione S-transferase (GST) encoded by the PGEX fusion vector (see, e.g., Winnacker, From Genes to Clones, New York: VCH Publishers, pp. 451–481 (1987)). As discussed below, other such fusion proteins include the Cyk-4 fused to immunoglobulin Fc at the N- or C-terminus.

A still further aspect of the present invention relates to antibodies and antibody preparations specifically reactive with an epitope of the Cyk-4 polypeptide.

Polyclonal antibodies are conventionally obtained by immunising animals, particularly rabbits, by injecting the antigen or fragments thereof and subsequently purifying the immunoglobulin.

Monoclonal anti-Cyk-4-antibodies may be obtained by standard procedures following the principle described by Köhler and Milstein, 1975, by immunising animals, particularly mice, then immortalising antibody-producing cells from the immunised animals, e.g. by fusion with myeloma cells, and screening the supernatant of the hybridomas obtained by immunological standard assays for monoclonal anti-Cyk-4-antibodies. For therapeutic or diagnostic use in humans, these animal antibodies may optionally be chimerised in the conventional way (Neuberger et al., 1984, Boulianne et al., 1984) or humanised (Riechmann et al., 1988, Graziano et al., 1995).

Cyk-4 specific antibodies can be used for both diagnostic and screening applications.

Cyk-4 specific antibodies are useful in clinical situations, where determining overexpression or underexpression of CYK-4 has predictive value. Anti-CYK-4 antibodies can be used on tissue of cell specimens to evaluate the level of expression or changes in the subcellular localization in various disease states. In addition, anti-CYK-4 antibodies can be used to detect the presence of CYK-4 in solid-phase binding assays as described in the subsequent subsection related to finding compounds that affect the interaction of CYK-4 with other proteins.

In a further aspect, the present invention provides screening methods for identifying compounds capable of modulating, in particular inhibiting, cytokinesis by modulating, in particular inhibiting, the function of CYK-4.

In a first embodiment, the screening method of the invention is used to identify compounds that modulate the function CYK-4 to promote GTP hydrolysis by Rho family GTPases. (Due to the evolutionary conservation of the GTPase domain and the requirement for Rho in cytokinesis, it can be concluded from the findings of the invention that the ability of CYK-4 to promote GTP hydrolysis by Rho is crucial for CYK-4 function.)

In this embodiment of the invention, a compound's ability to promote GTP hydrolysis by a Rho family GTPase is determined by incubating a substrate selected from the members of the Rho family GTPases with GTP for a period of time sufficient to allow saturation of the substrate's GTP binding sites, adding Cyk-4 and allowing it to react in the presence or absence of the test compound, and determining the amount of hydrolyzed GTP.

This type of assay may be conducted on the basis of the so-called "GTP hydrolysis assay", which is a biochemical assay carried out according to standard protocols, as described, inter alia, by Self et al., 1995, or by Settleman and Foster, 1995. By way of example, this assay may be carried out as follows: In a first step, the substrate is incubated with GTP that carries a radioactive label (e.g. like the commercially available $\gamma$-$^{32}$P-GTP, or an otherwise measurable, e.g. a fluorescent label, as described, inter alia, by Hazlett et al., 1993, under conditions and for a period of time sufficient to allow saturation of GTP binding sites. Subsequently, CYK-4 is added, optionally at various concentrations of from 0 to eg 1 uM; in the presence of absence of test compounds. After the appropriate time (e.g. 5 min.) the amount of GTP that has been hydrolysed is determined.

After the time required for CYK-4 stimulated GTP hydrolysis by Rho in the control reaction (absence of test compound), the reaction solution may be filtered through a protein binding matrix, e.g. nitrocellulose, that is arranged in the same geometrical pattern as the original microtiter plate where the reaction took place, and the radioactivity retained in the filters, or the amount of liberated free phosphate (or other label as appropriate) is quantified.

To simplify the screening assay, the Rho protein may be immobilized on a solid matrix, either via a tag that allows for binding to a suitably modified solid support, e.g. by using a biotinylated Rho protein and a streptavidin-coated microtiter plate, the solid matrix may also be in the form of beads. In the above-described assays that measure GTP hydrolysis, the Rho protein is preferably human.

By way of example, the assay may be conducted as follows: A member of the Rho family GTPases is immobilized on a solid support, e.g. a SPA (proximity scintillation assay bead) using either an epitope tag such as His6 or other similar tags. The Rho protein is loaded with radioactive $^{32}$P-gamma-GTP in the presence of EDTA. Magnesium and Cyk-4 are added in the absence or presence of test compounds, incubated for various times at which point the amount of radioactivity or other suitable label remaining associated with the beads is measured. Other embodiments of the assay include using alternative labels such as fluorescent GTP or other radioisotopes and using alternative measures of GTP hydrolysis such as measuring the amount of free $^{32}$P released, as described above.

Alternatively to using the full-length Rho protein, a truncated version may be used, as long the GTPase activity is maintained, e.g. a fragment that lacks the critical cysteine residue in the CaaX box at the C-terminus that is required for membrane targetting.

A number of Rho proteins are available that are suitable for use in a GTP hydrolysis assay as a substrate, they have been cloned from various species. Preferably, the are employed as recombinant proteins.

Examples for Rho substrates that may be employed are human RhoA (Swiss Prot Primary Accession Number P06749), human RhoB (Swiss Prot Primary Accession Number P01121), human RhoC (Swiss Prot Primary Accession Number P08134), human RAC1 (Swiss Prot Primary Accession Number P15154), human RAC2 (Swiss Prot Primary Accession Number P15153), human RAC3 (Swiss Prot Primary Accession Number O14658) and human GB25 (Swiss Prot Primary Accession Number P21181).

Based on the sequence information, the Rho substrates and the potentially present co-factor(s) can be produced recombinantly in suitable host cells, e.g. in E. coli or by means of baculovirus in insect cells, according to standard methods.

Compounds that have the ability to prevent CYK-4 stimulated GTP hydrolysis by Rho family GTPases are then tested for specificity in a similar assay format using other proteins that have Rho family GAP domains, e.g. p190 or RhoGAP (Lamarche and Hall, 1994).

In an alternative embodiment of the screening method, the compound's ability to inhibit Cyk-4 function is determined by determining the compound's ability to interfere with the biochemical interaction of CYK-4 with a member of the MKLP1 subfamily.

The function of CYK-4 in cytokinesis is intimately tied to its ability to interact with MKLP1, a kinesin like protein that is also required for central spindle assembly. Therefore compounds that inhibit this interaction are expected to prevent cytokinesis and to inhibit cell proliferation.

Examples for members of the MLKP1 family are CeM03D4.1b (C. elegans; GenBank ID U61955, Protein ID 1397342) (SEQ ID NO:7) and HsMKLP1 (human; GenBank ID X67155; SwissProt Q02241) (SEQ ID NO:8). Preferably, HsMKLP1 is employed.

In C.elegans extracts, CYK-4 and CeMKLP1 are present in a protein complex and can be co-immunoprecipitated and co-purified. The nature of this protein interaction can be further characterized, in particular by determining whether additional proteins also interact with this complex.

In an assay that employs an additional protein component involved in this interaction, a compound's ability to modulate Cyk-4 function is determined by determining its effect on the interaction of said protein with the Cyk-4/MKLP1 complex.

In carrying out an assay based on the Cyk-4/MKLP1 interaction, a minimal set of proteins necessary to form a stable complex, i.e. Cyk-4, MLKP1, and additional potential protein co-factors are produced in recombinant form.

The domains required for the interaction of Cyk-4 and MKLP1 have been identified by the present inventors.

In an embodiment of the invention, the domain of Cyk-4 that interacts with MKLP1 (i.e. the N terminal Cyk-4 region containing at least amino acids 1–120), or the whole Cyk-4 protein, is immobilized on a solid support, as described below. The domain of MKLP1 that interacts with CYK-4 (i.e. the central MKLP1 domain containing at least amino acids 503–603) or the whole MLKP1 protein that is modified with a suitable label to allow for rapid detection (i.e. radiolabelled, fluorescently labeled, hapten labelled etc., as described below) is incubated in the presence or absence of the test compounds.

After an incubation period that allows for interaction of the proteins, e.g. for about 20 minutes at 25° C., the amount of MKLP1 bound to the immobilized CYK-4 is measured by use of the label outlined above or by the use of suitable antibodies in an ELISA type assay. The assay may also be setup in the reverse, e.g. with Cyk-4 being labeled or with MKLP1 immobilized, or by performing the binding reaction in solution and then capturing one of the components on a solid support and measuring the amount of the other component that is co-immobilized.

According to another aspect, the invention relates to a screening method that takes advantage of the biochemical multimerization of CYK-4 on the one hand and the biochemical multimerization of the MKLP1 subfamily of the kinesin-like protein superfamily on the other hand. This approach is based on the finding that the domain of CYK-4 that is required for interaction with MKLP1 contains a coiled-coil domain that mediates self association. Likewise the domain of MKLP1 that is required to interact with CYK-4 contains a coiled-coil domain that mediates self association.

Since the ability of these proteins to self association is expected to be required for their function in vivo, compounds that inhibit the self assocation of either one or both of the interaction partners Cyk-4 and MKLP1 are candidates for perturbing cytokinesis.

In an embodiment of the invention that is based on determining whether a test compound has the ability to interfere with the self association of Cyk-4, the N-terminal domain of CYK-4 (containing at least amino acids 1–120), or the whole Cyk-4 protein, is immobilized on a solid support, either directly or through a tag. (Suitable tags are commercially available, e.g. the FLAG, HA, MYC, HIS tag, etc.).

Examples for solid supports useful in the present invention are commercially available immunobeads or immunoplates, e.g. 96- well immunoplates, or microchips, which are coated with an antibody directed against one of the above-listed tags fused to the interacting protein.

A second CYK-4 fragment consisting of or containing the N terminal domain of CYK-4, i.e. amino acids 1–120, or the whole Cyk-4 protein is modified with a suitable label that allows for rapid detection. (The immobilized and the labeled Cyk-4 protein (fragments) may be identical or different.)

Examples for suitable labels are commercially available radioactive or fluorescence labels, hapten labels, or peptide labels, e.g. Europium or the Green Fluorescent Protein (GFP), an enzyme label, e.g. luciferase, alkaline phosphatase etc.)

The labeled Cyk-4 (fragment) is incubated with the immobilized CYK-4 in the presence or absence of the test compounds.

After an incubation period that allows for interaction of the proteins, e.g. for ca. 20 min, the amount of CYK-4 bound to the immobilized CYK-4 is determined by measuring the signal of the label or by the use of suitable antibodies in an ELISA type assay.

In a further embodiment of the invention, the screening method to identify modulators of Cyk-4 function is based on determining whether a test compound has the ability to interfere with the self association of MKLP1. In this embodiment, the central domain of MKLP1 (containing at least amino acids 503–603) or the whole MKLP1 protein, is immobilized on a solid support.

A second MKLP1 fragment, consisting of or containing the above-defined central domain of MKLP1, or the whole MKLP1 protein is modified with a suitable label that allows for rapid detection. (The immobilized and the labeled MKLP1 protein (fragments) may be identical or different).

The assay for identifying inhibitors of MKLP1 self assembly may be conducted in the the same way as described above for identifying inhibitors of Cyk-4 self assembly.

All embodiments of the screening methods of the invention may be performed in the high throughput format by automation of the reaction steps. In this case, a great number of compounds, e.g. from compound or natural product libraries, are applied to microtiter plates containing the components necessary for the reaction.

Due to their ability of inhibiting the function of Cyk-4 to promote GTP hydrolysis by Rho family GTPase, of interfering with the interaction between Cyk-4 and MKLP1, or by interfering with self assembly of Cyk-4 and/or MKLP1, respectively, compounds identified in the above screens have the potential to perturb cytokinesis. In tumor cells, this effect may result in a decrease or a stop of tumor growth. In addition, inhibition of cytokinesis may cause the activation of a cell cycle arrest check point that will trigger apoptosis of the tumor cells.

In light of the recent observation (Van de Putte et al 2001) that murine CYK-4 is highly expressed in Purkinje cells of the brain, in particular in cells that have abundant antiparallel bundles of microtubules (as is the case in the central spindle), it may be assumed that compounds that inhibit CYK-4 function in cytokinesis may also impair CYK-4 function in neuronal cells. Inhibitors of CYK-4 function in these cells may have have utility in the treatment of neurological disorders, e.g. neuronal hyperactivity.

Compounds that have been identified in the above-described assays to specifically affect CYK-4 function are drug candidates which may be further developed, e.g. in a first step, by structure-function analysis.

To further evaluate the potential of the compounds as drugs, the candidate compounds can be assayed for their effect on cytokinesis and other cellular processes in tissue culture of normal or transformed cells. To test the inhibition of tumor cell proliferation, primary human tumor cells, are incubated with the compound identified in the screen and the inhibition of tumor cell proliferation is tested by conventional methods, e.g. bromo-desoxy-uridine or $^3$H thymidine incorporation.

Compounds that exhibit an anti-proliferative effect in these assays may be further tested in tumor animal models and used for the therapy of tumors.

Thus, in a further aspect, the invention relates to compounds identified in the above screens for the therapy of tumors and any other situation in which cell overproliferation is observed.

Toxicity and therapeutic efficacy of the compounds identified as drug candidates by the screening methods of the invention can be determined by standard pharmaceutical procedures, which include conducting cell culture and animal experiments to determine the $IC_{50}$, $LD_{50}$, the $ED_{50}$. The data obtained are used for determining the human dose range, which will also depend on the dosage form (tablets, capsules, aerosol sprays, ampules, etc.) and the administration route (oral, buccal, nasal, paternal or rectal). A pharmaceutical composition containing the compound as the active ingredient can be formulated in conventional manner using one or more physiologically active carriers and excipients. Methods for making such formulations can be found in manuals, e.g. Remington Pharmaceutical Sciences, 1980; Remington: The Science and Practice of Pharmacy, 2000.

BRIEF DESCRIPTION OF THE FIGURES

FIGS. 3A–3D: Positional cloning of the cyk-4 locus.

Figure 1:
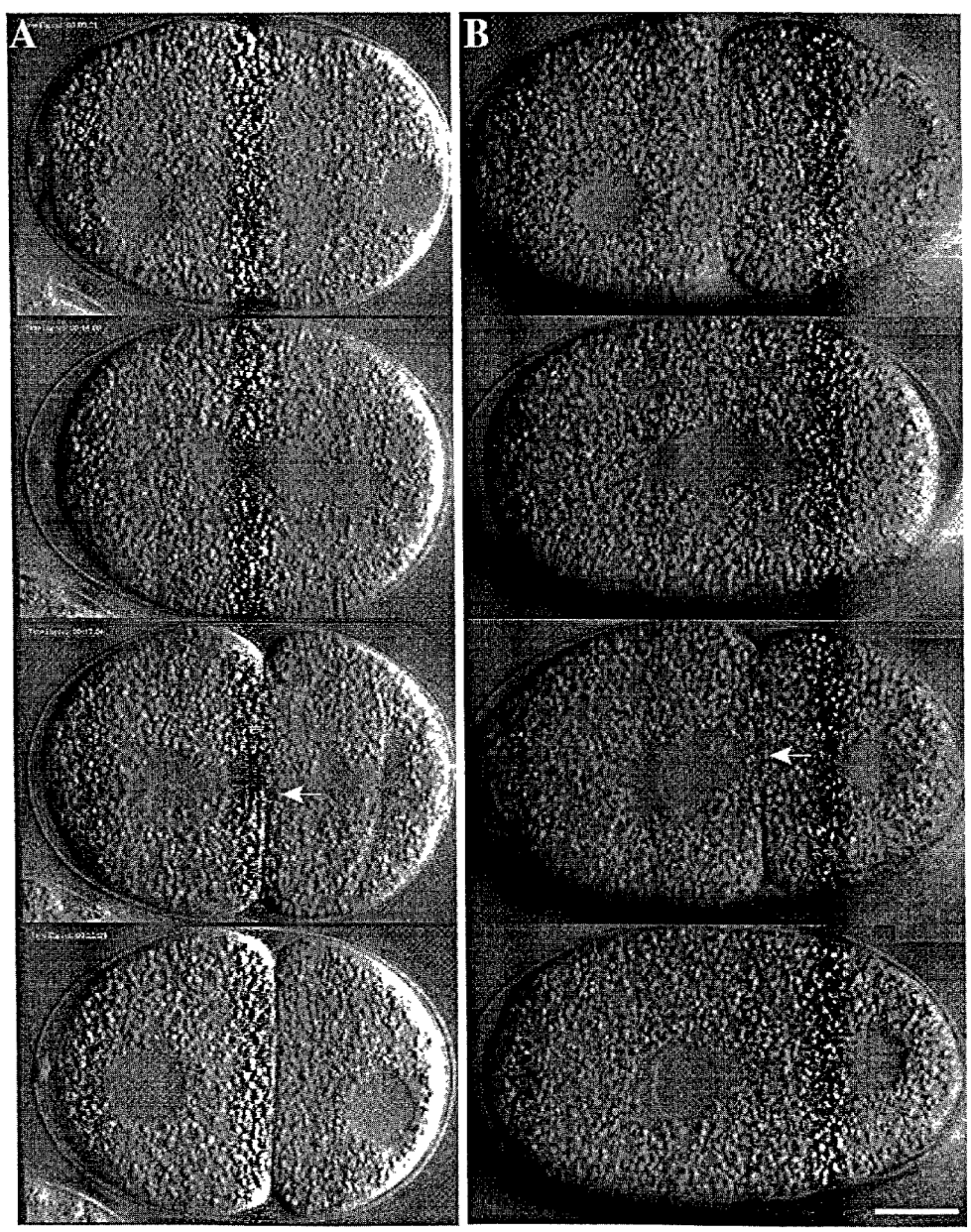
FIG. 1: cyk-4(t1689ts) mutant embryos fail to complete cytokinesis.

In the Examples 1–5, if not otherwise stated, the following materials and methods were used:

a) Strains and Alleles

The cyk-4(t1689ts) allele was identified in a search for maternal effect lethal mutations on chromosome III (see (Gönczy et al., 1999b) for details). The strains DR104, BW1535, BW1369, and RW7000 were obtained from the CGC (C. elegans Genetics Center). The strain EU699 containing the zen-4(or153ts) allele was described by Severson, et al., 2000. The end points of the deficiency tDf10 (Heinke Schnabel, unpublished data) are not molecularly defined, but it uncovers cyk-4, lit-1, and bli-5 and it does not uncover unc-64.

b) Antisera

Cyk-4 specific antisera were produced in rabbits using a His6-Cyk-4 fusion protein as immunogen (containing amino acids 407–613 of cyk-4). A GST-Cyk-4 fusion containing amino acids 407–681 of Cyk-4 was coupled to a Hi-Trap NHS resin (Amersham-Phamacia) and used to affinity purify anti-Cyk-4 antibodies which were used at a final concentration of 1:300. The antibodies used for the studies are specific for Cyk-4 since the staining can be blocked with antigen, a similar pattern is observed when anti-GFP antibodies are used to detect a Cyk-4:GFP fusion construct, and the staining pattern is disrupted in cyk-4 mutant embryos. The rat monoclonal YOL 1/34 anti-tubulin antibody was used at a dilution of 1:200–500. Anti-GFP antibodies (Roche) were used at a dilution of 1:500. Antisera specific for Zen-4/MKlp1 was generously provided by Bill Saxton and Susan Strome (Univ. of Indiana) and used at a dilution of 1:4000. Antisera specific for Air-2 was generously provided by Andy Golden (NIH) and used at a dilution of 1:1000.

c) Genetic Mapping of Cyk-4

The cyk-4 locus maps under the deficiency tDf6 which deletes a large fraction of the distal right arm of LGIII. Recombination mapping using unc-32(e189) cyk-4 (t1689ts)/dpy-18(e364) unc-25(e156) placed cyk-4 distal to (or very close to) unc-25 (23/23 Dpy non Unc's carried the cyk-4 mutation). Recombination between dpy-18 cyk-4/RW7000 which carries several Tc1 elements including one on the cosmid F14F7 gave rise to 45 Dpy non-Ts animals, 3 of which lacked the TC1 insertion on F14F7, indicating that the cyk-4 gene is distal to this cosmid. Crosses to strains carrying the deficiencies ctDf3, ctDf2, tDf10 revealed that cyk-4(t1689ts) is not uncovered by ctDf3 and is uncovered by both ctDf2 and tDf10. Since tDf10 does not uncover unc-64, cyk-4(t1689ts) must be distal to unc-64.

d) Time Lapse Recordings

Time lapse Nomarski imaging was performed as described previously (Jantsch-Plunger and Glotzer, 1999). Time lapse imaging of Cyk-4:GFP was performed on a Zeiss Axiovert microscope using a 100x/1.3 neofluar objective. The illumination source, an Atto-arc HBO-103, was reduced to 50% intensity. An intensified cooled CCD camera (GenIV pentamax, Princeton Instruments) was used for image acquisition. The camera and other electronics were controlled with MetaMorph software (Universal Imaging). Typical acquisition times were 40–80 msec. Each 10 seconds, 4–5 fluorescent images were acquired at different focal planes and a nomarski image was acquired. The fluorescent images were projected onto a single frame using the maximum intensity from the stack of images. Under these conditions, embryos could be filmed for more than one hour without affecting the cell cycle timing or pattern of cell divisions.

e) Rescue Experiments

To identify the cyk-4 gene in this region cosmid DNA (from stocks kindly provided by Alan Coulson, Sanger Center) was coinjected with the rol-6(su1006) dominant marker (Mello et al., 1991) into the gonad of unc-32 cyk-4/qC1 worms. Heterozygous F1 hermaphrodites that carried the rol-6 dominant marker were cloned to individual plates at 25° C. and the presence of Unc progeny, indicating zygotic rescue of the cyk-4 mutation, was assessed. Individual unc-32, cyk-4 worms carrying the extrachromosomal arrays were cloned to individual plates to assess the extent of germline rescue. The cyk-4 genomic rescue construct MP17, contains a 4.9 kb genomic XbaI fragment excised from K08E3 and inserted into pBS-KS+.

f) RNA Interference

Approximately 500 bp of DNA corresponding to predicted coding regions of Rho (Y51H4A.B), Rac-1 (C09G12.8B), Cdc42 (R07G3.1), F22E12.2, Y32F6B.3, K08D3.9, K08E3.2, K08E3.3, K08E3.4, K08E3.6, K08E3.7, K08E3.8 were amplified by PCR and cloned into pGEM-T (Promega). Double stranded RNA was transcribed (Ambion) and annealed, and injected into the gonads of wildtype N2 hermaphrodites as described (Fire et al., 1998).

g) Production of Cyk-4:GFP Transgenes

The GFP cassette from vector pPD119.16 was excised with BspLUIII and inserted into the unique NcoI site of MP17 (see above). This construct was linearized with XbaI, and complex arrays containing linearized genomic DNA and linearized rol-6(su1006) DNA were mixed in a ratio of 1:100:1 and injected into unc-32(e189) cyk-4(t1689ts)/qC1 hermaphrodites. Rolling F1 heterozygotes were singled out at 25° C. and rolling Unc F2 animals were picked. A line MG110, was obtained that gave stable rescue of the cyk-4 (t1689ts) mutation.

The structure of the cyk-4 gene was established by analysis of a large number of EST sequences available in the sequence databases at the Sanger Center and the National Institute of Genetics and by sequencing the clones yk63D6 and yk104g12 (kindly provided by Yuji Kohara). The structure of the gene is identical to the structure predicted by the *C. elegans* genome consortium.

h) Immunolocalization

Immunolocalization studies were performed as previously described (Jantsch-Plunger and Glotzer, 1999). Briefly, gravid hermaphrodites were placed on aminoproyl-silane treated slides, a coverslip was added, and sufficient pressure to extrude the embryos was applied. The slide was placed into liquid nitrogen. The coverslip was removed while the sample was still frozen, the preparation fixed with −20° C. methanol and then antibody staining was performed according to standard procedures.

i) Biochemical Analysis of Cyk-4

The coding regions of Rho, Rac, and Cdc42 were PCR amplified and cloned into pET28b with an C-terminal polyhistidine tag. The GTPases were expressed at 25° C. and purified using $Ni^{2+}$-NTA-agarose (QIAGEN). Proteins were dialyzed into 50 mM Tris pH 7.5, 50 mM NaCl, 5 mM $MgCl_2$ and quick frozen. The GAP domain of Cyk-4 (amino acids 407–681) was cloned into pGEX4T-1. Proteins were expressed at 25° C. and purified using GSH-agarose (Sigma). Proteins were dialyzed into 50 mM Tris pH 7.5, 50 mM NaCl, 5 mM $MgCl_2$, 1 mM DTT and quick frozen. To assess GAP activity, 15 pmol of the GTPases were loaded with 1 pmol $^{32}P$-α-GTP in 20 mM Tris pH 7.6, 4 mM EDTA, 25 mM NaCl, 1 mM DTT, 1 mM ATP, 0.1 mg/ml BSA at room temperature. The sample was place on ice and $MgCl_2$ was added to 17 mM. GST-Cyk-4-GAP was added at the indicated concentrations and, at intervals, samples were taken by dilution into 2% SDS, 20 mM EDTA. Aliquots were spotted onto TLC plates (PEI-cellulose, Machery-Nagel) and developed in 1M LiCl. The plates were dried and exposed using a Storm Phosphoimager (Molecular Dynamics) and the data analysis was performed using the public domain NIH Image program (developed at the U.S. National Institutes of Health; http://rsb.info.nih.gov/nih-image/).

EXAMPLE 1 cyk-4 Mutants Initiate, but do not Complete, Cytokinesis

The cyk-4(t1689ts) allele was isolated in a screen for maternal effect embryonic lethal mutations on chromosome III (Gönczy et al., 1999b). The cyk-4 locus is defined by a single, temperature sensitive (ts), allele. The phenotype of embryos derived from homozygous cyk-4 hermaphrodites at the restrictive temperature (hereafter referred to as cyk-4 mutant embryos) during the first division is shown in FIG. 1B. cyk-4 mutant embryos appear normal until cytokinesis, except that defects in polar body extrusion are frequently observed (data not shown). The first cleavage furrow forms at the correct time and place, it ingresses extensively, but, invariably, it regresses. Quantitation of the extent of furrow ingression in cyk-4 mutant embryos reveals that, on average, furrows ingress to 73+/−13% (n=14) of the egg diameter. A multipolar spindle develops in the second cell cycle and the process of furrow ingression and regression occurs again. This pattern is repeated until the embryos become grossly disorganized. (FIG. 1 shows that cyk-4(t1689ts) mutant embryos fail to complete cytokinesis. Wildtype embryos (A) and embryos from cyk-4 mutant hermaphrodites (B) were dissected from young adults, mounted on agarose pads and observed by time-lapse nomarski microscopy. The ingressing cleavage furrow is indicated (arrows) 0.10 μm scale bars.)

Although the majority of cell divisions in worm development occur early in embryogenesis, cells of the germline and and many cells in the nervous system are produced during post embryonic development (Sulston and Horvitz, 1977). A number of mutations in genes required for cell division cause worms to become sterile and uncoordinated (O'Connell et al., 1998; Woollard and Hodgkin, 1999). To determine if cyk-4 is required post embryonically, temperature shift experiments with worms homozygous for the cyk-4(t1689ts) allele were performed (table 1). Homozygous animals grown at 16° C. are viable and fertile. Homozygous cyk-4 animals shifted to 25° C. at the L4 stage produce embryos with the cytokinesis defects described above. Homozygous animals shifted to 25° C. at earlier stages either fail to hatch or become sterile and uncoordinated, depending on the time of the temperature shift. Thus cyk-4 is required postembryonically, perhaps due to its role in cell division. Unexpectedly, animals shifted at the L2/L3 stages become highly uncoordinated adults, even though most motor neurons would be expected to have completed all their divisions at the time of the shift. This may suggest that CYK-4 has additional roles besides its role in cell division. However, not out the possibility cannot be ruled out that some of the cells in the ventral nerve cord divide later in cyk-4 mutants.

Figure 2:
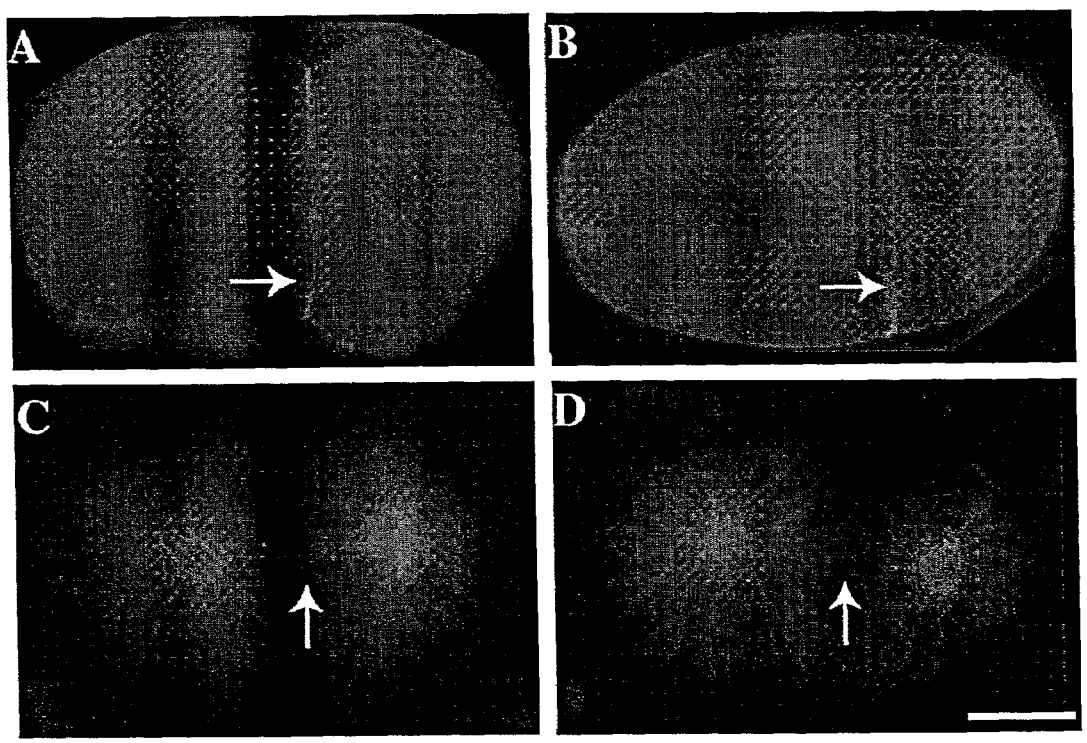
FIG. 2: cyk-4 mutant embryos produce deeply ingressing cleavage furrows, but do not form a prominent central spindle.

To investigate why cyk-4 mutant embryos fail to complete cytokinesis, actin and tubulin were localized in wild-type and cyk-4 mutant embryos. Both wild-type and mutant embryos contained deeply ingressing cleavage furrows that stain with an anti-actin antibody; the results are shown in FIG. 2. FIG. 2A,B shows that cyk-4 mutant embryos produce deeply ingressing cleavage furrows, but do not form a prominent central spindle. Wild type (A, C) and cyk-4 mutant embryos (B,D) were fixed and stained for actin (green) and DNA (blue) (A,B); tubulin (green) and DNA (blue) (C,D)0.10 µm scale bars.

The metaphase spindles of cyk-4 mutant embryos appeared normal. However, spindle morphology during early anaphase was significantly different in mutant embryos as compared to wild type. In wild-type embryos (20/20) prominent microtubule bundles form between the separating masses of chromatin, forming the central spindle (FIG. 2C). In cyk-4 mutant embryos (9/10) such bundles were largely reduced and disorganized (FIG. 2D). It is concluded that CYK-4 is required for the organization of the central spindle during anaphase. Since the central spindle is required for cytokinesis, it is possible that the cyk-4 mutant embryos fail to complete cytokinesis because they fail to assemble the central spindle.

EXAMPLE 2

Cloning of the cyk-4 Gene

Figure 3D:
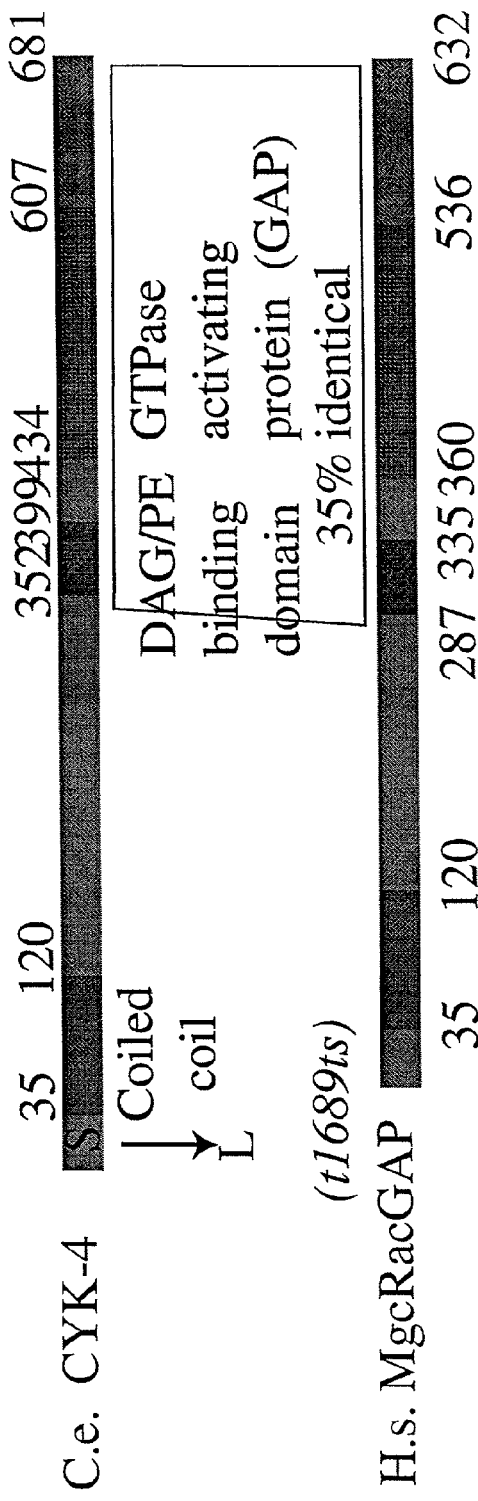

To investigate the molecular basis for the phenotypes described above, it was first sought to map the cyk-4 locus and clone the affected gene (see methods for details). The cyk-4 gene maps distal to unc-64 on the extreme right arm of LG III. FIG. 3 shows the positional cloning of the cyk-4 locus. (A) A schematic of LGIII showing the positions of various loci and the extent of the deficiencies. cyk-4 is uncovered by tDf10, tDf6, and ctDf2, but not ctDf3. (B) An enlargement of the physical map from the unc-64 locus until the end of LGIII. The ability of various cosmid pools to rescue cyk-4 is indicated. (C) A map of the predicted genes on K08E3. All the predicted genes except for K08E3.1 and K08E3.5 were inactivated by RNAi and only RNAi of K08E3.6 produced multinucleate embryos. (D) A schematic representation of the domain structure of CYK-4 and its human ortholog. The position of the point mutation identified in cyk-4(t1689ts) is indicated.

The cyk-4 gene was then identified by functional rescue of the zygotic requirement for cyk-4 using pools of cosmids. A pool of three cosmids (ZK520, WO6F12, and K08E3) allowed cyk-4 homozygotes to hatch and develop to adulthood at 25° C. These cosmids were injected individually and cosmid K08E3 contained rescuing activity. Further subcloning revealed that a 4.9 kb genomic fragment, predicted to contain the complete K08E3.6 gene and no other intact gene, could rescue the cyk-4 zygotic and germline phenotypes. Finally, the coding region was amplified from DNA derived from cyk-4(t1689) homozygotes and sequenced and a single point mutation was identified that differed from the sequence provided by the genome project; this mutation was not observed in another line derived from the same parental strain. These data show that the defect in cyk-4(t1689ts) embryos is due to a point mutation in the K08E3.6 gene.

The predicted protein product of the cyk-4 gene has a C-terminal domain that contains the consensus motifs of GTPase activating proteins for Rho family GTPases (FIG. 3). Adjacent to the C-terminal GAP domain is a C1 domain that is predicted to bind to diacylglycerol or phorbol esters. At the amino terminus of the protein is a 90 amino acid region predicted to form a coiled-coil domain. The S15L point mutation found in cyk-4(t1689ts), is located just amino terminal to the coiled-coil domain. Human and mouse proteins with structural similarities to cyk-4 have been described (Toure et al., 1998; Wooltorton et al., 1999). These genes are expressed in a variety of proliferating tissues. In addition, the $Drosophila$ sequence database contains an entry (ascension no. AC005977 (CLOT 94)) that, together with CYK-4 and the previously mentioned human gene, share a common structure consisting of approximately 650 amino acids, an $NH_2$-terminal coiled-coil domain and a conserved C-terminus containing C1 and GAP domains. The structural conservation of CYK-4 suggests that its function is conserved among metazoans.

In the present invention, the the human and mouse cDNA's were identified by searching the DNA databases with the $C.elegans$ CYK-4 protein sequence.

Since the cyk-4(t1689ts) mutation may contain residual activity RNA-mediated interference (RNAi) was used to deplete embryos of CYK-4 protein.

Figure 4:
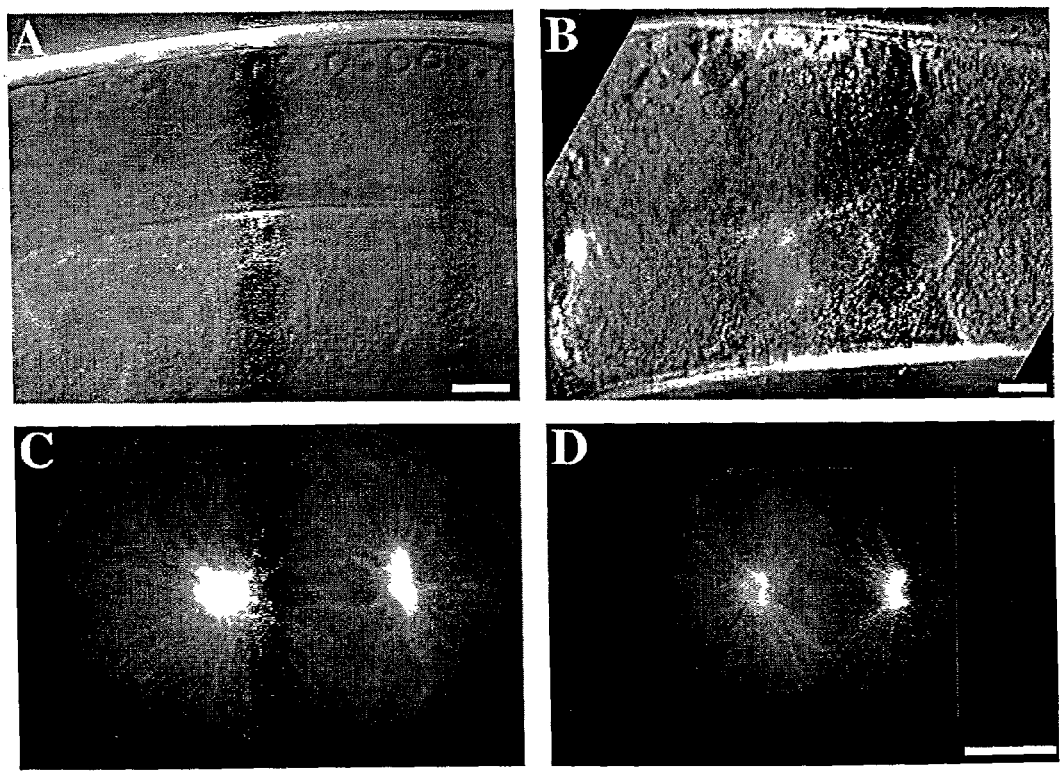
FIG. 4: cyk-4(RNAi) causes disorganization of the proximal gonad and affects formation of the central spindle.

FIG. 4 shows that cyk-4(RNAi) causes disorganization of the proximal gonad and affects formation of the central spindle. Young adults were injected with cyk-4 dsRNA and the injected animals were analyzed 30 hours after injection (B). The gonad of an uninjected worm is shown for comparison (A). Wild-type embryos (C) and embryos from cyk-4(RNAi) injected animals (D) were fixed and stained for tubulin. 10 µm scale bars.

RNAi of the predicted open reading frame K08E3.6 generated multinucleate embryos which exhibited a similar phenotype to that of the cyk-4 mutant, including loss of the central spindle (FIG. 4 D) and incomplete cytokinesis (not shown). Interestingly, the gonads of cyk-4(RNAi) animals become disorganized 30 hours post-injection (FIG. 4 B) and irregularly sized embryos are produced, suggesting that CYK-4 acts not only during embryonic and zygotic development, but also in the female germline.

EXAMPLE 3

Biochemical Activity of the Cyk-4 GAP Domain

Figure 5:
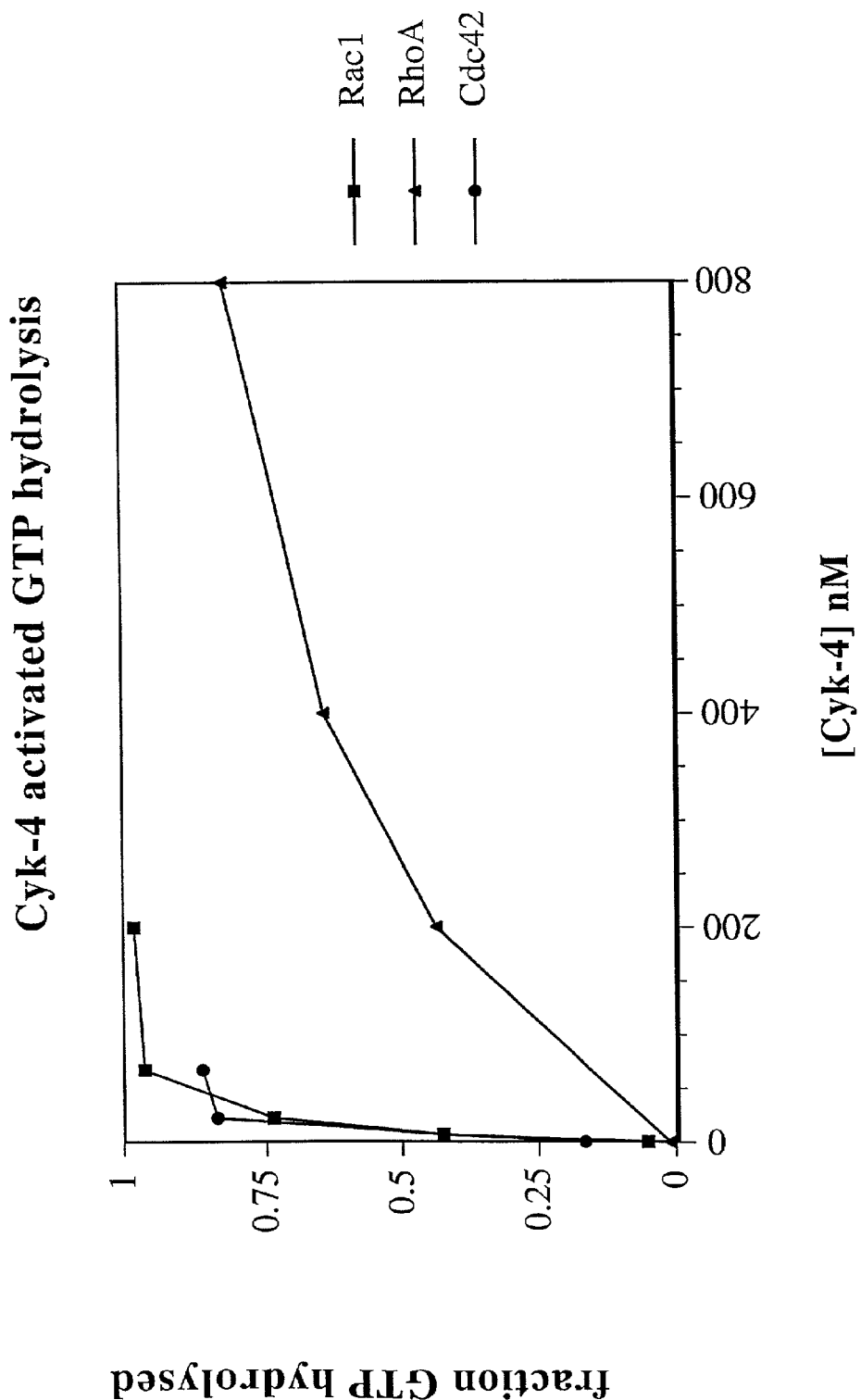
FIG. 5: CYK-4 enhances GTP hydrolysis by Rho, Rac, and Cdc42.

The presence of a Rho-family GAP domain suggests that CYK-4 may regulate one or more GTPases of Rho branch of the GTPase superfamily. To determine whether CYK-4 is active as a GAP and whether its GAP activity is restricted to particular members of the Rho subfamily, a recombinant fusion protein containing GST and the CYK-4 GAP domain was prepared and GTP hydrolysis assays were performed with recombinant *C. elegans* Rho, Rac, and Cdc42. The GAP domain of CYK-4 promotes GTP hydrolysis by all three tested GTPases. FIG. 5 shows that CYK-4 enhances GTP hydrolysis by Rho, Rac, and Cdc42. The GTPases were preloaded with $^{32}P$-$\alpha$-GTP and then GST-CYK-4-GAP or GST was added at the indicated concentration. Samples were taken at two minute intervals, the labeled nucleotide was resolved by thin layer chromatography, the fraction of GTP and GDP was quantitated. This graph shows the fraction of GTP hydrolyzed at the 2 minute time point as a function of CYK-4 concentration. These data are representative of at least three independent experiments.

However kinetic differences were observed. At the conditions used in the assays it was found that the CYK-4 GAP domain is more active towards Rac and Cdc42 than towards Rho. The human ortholog has a similar activity profile in vitro (Toure et al., 1998). However, since CYK-4 has activity towards all three GTPases, these data are not sufficient to determine the in vivo target(s) of the CYK-4 GAP domain.

Next RNAi was used to determine which, if any, of the Rho family GTPases are required for cytokinesis in the *C. elegans* embryo. RNAi experiments were performed with RhoA, Rac1, Cdc42 and three additional GTPases found in the genome that fall into the Rho subfamily. Approximately 90% of Rho(RNAi) embryos exhibit cytokinesis defects in the first and/or second cell cycle (table 2 and FIG. 6).

Figure 6:
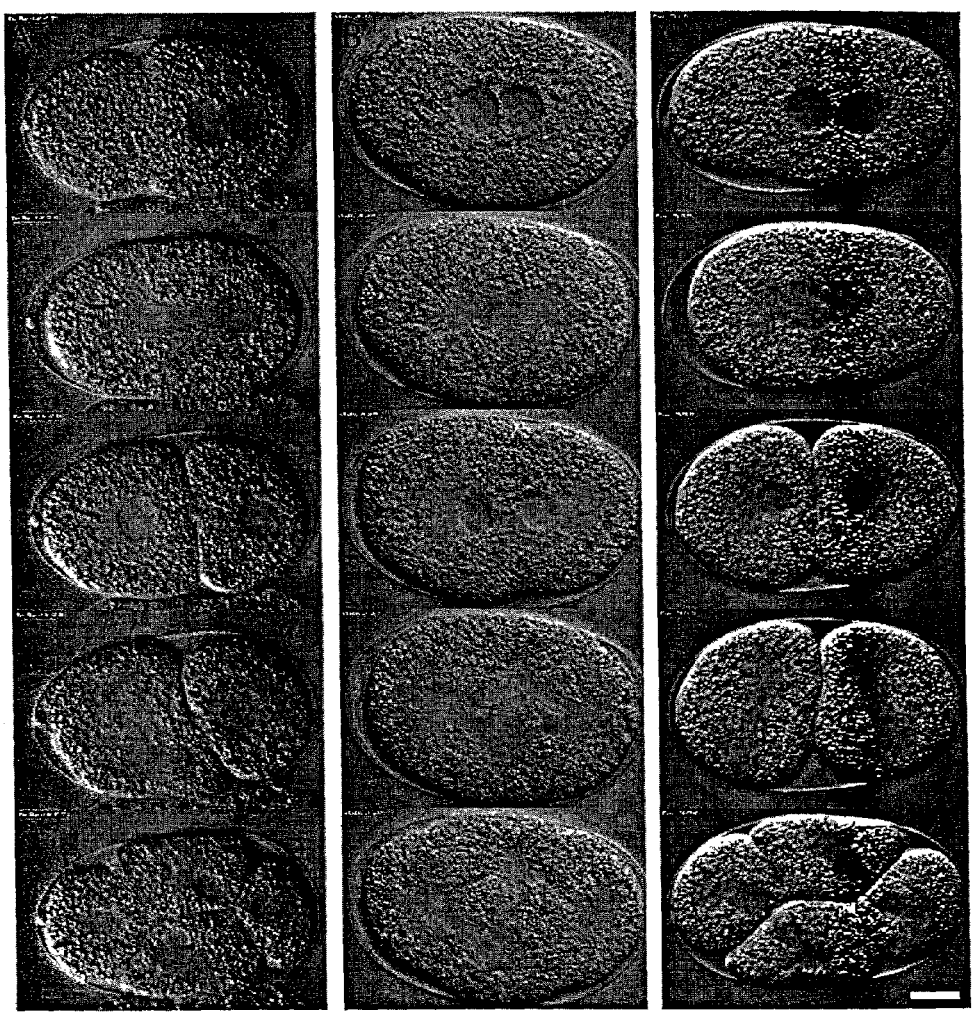
FIG. 6: rho(RNAi) causes cytokinesis defects and cdc42 (RNAi) causes defects in spindle positioning.

FIG. 6 shows that rho(RNAi) causes cytokinesis defects and cdc42(RNAi) causes defects in spindle positioning. Young adults were injected with the indicated dsRNAs (see table 2) and the embryos produced by the injected worms were analyzed by time lapse nomarski microscopy. Images from a wild-type (A), rho (RNAi) (B) and a cdc42(RNAi) (C) embryo are shown. 10 µm scale bars.

In most embryos, furrow ingression was inhibited. Interestingly, central spindles assemble in RhoA(RNAi) embryos (data not shown). In contrast, 88% of Cdc42(RNAi) embryos complete cytokinesis normally. However, a distinct defect in the early embryo is observed in 54% of Cdc42 (RNAi) embryos; defects in spindle positioning are observed in P0 and/or P1. A minority (12%) of Cdc42(RNAi) embryos fail to initiate cytokinesis; in most cases, these embryos appear osmotically swollen even when provided with osmotic support. Rac(RNAi) embryos hatch with high efficiency and did not exhibit a detectable phenotype in the early embryo. RNA interference experiments with the additional GTPases either alone or in combinations did not reveal any additional defects in the early embryo. Thus RhoA is the only member of the Rho family that is clearly required for cytokinesis and is therefore likely to be the critical target for the CYK-4 GAP domain.

EXAMPLE 4

The Subcellular Localization of Cyk-4

Figure 7:
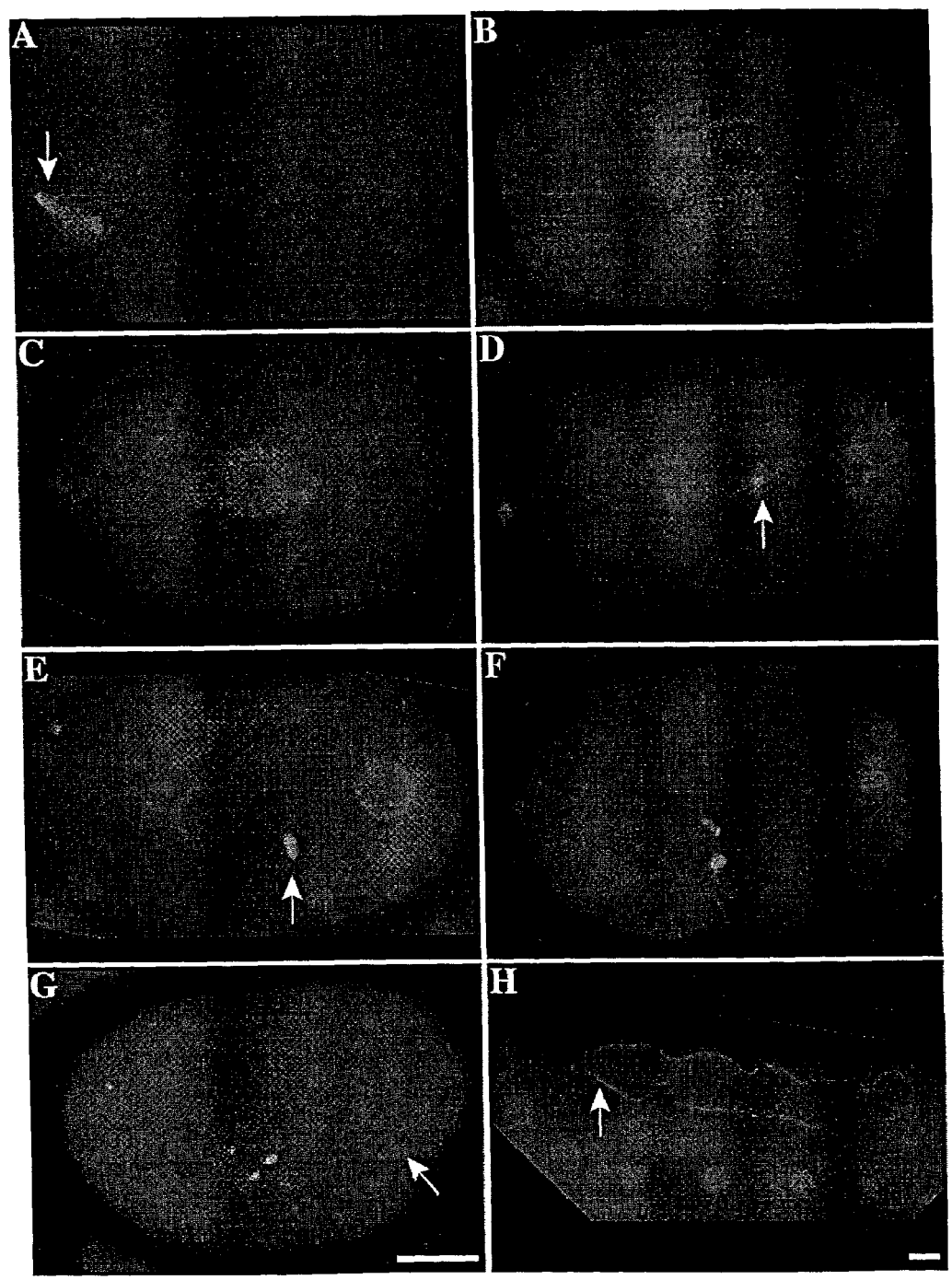
FIG. 7: CYK-4 localizes to the central spindle and division remnants.

Next the subcellular localization of CYK-4 protein was determined. CYK-4 localization is cell cycle dependent FIG. 7 shows that CYK-4 localizes to the central spindle and division remnants. (A–F) Wild-type embryos were fixed and stained for CYK-4 (green), tubulin (red) and DNA (blue). The localization of CYK-4 to the central spindle (arrow) in a one cell embryo (D) and a two cell embryo (F) is shown. The localization of CYK-4 to the division remnant from the polar body (A), and between the AB and P1 blastomeres is indicated with arrows. (E). (G) An embryo from a line expressing CYK-4:GFP is stained with anti-GFP antibodies. The same structures are seen as with CYK-4 antibodies (arrow). (H) The intrinsic fluorescence of the gonad of a worm expressing CYK-4:GFP. CYK-4 is seen at the incomplete membranes of the syncytial gonad (arrow) and in oocyte nuclei. 10 µm scale bars.

In interphase cells, CYK-4 is present in the cytoplasm and slightly concentrated in the nucleus. CYK-4 is also highly concentrated in a spot at the anterior of the embryo, DNA labeling reveals that this localization corresponds to the site of polar body extrusion. As embryos enter mitosis, CYK-4 protein concentrates around the mitotic spindle. In early anaphase, CYK-4 concentrates to the central spindle. As the cleavage furrow ingresses, CYK-4 becomes highly concentrated on the central spindle into a structure that often appears ring shaped (not shown). Upon completion of cytokinesis, CYK-4 staining persists at division remnants. CYK-4 organized in ring-like structures averaging 1.2 µm in diameter are occasionally observed in the cytoplasm (not shown).

To determine if CYK-4 localizes to the central spindle prior to the onset of cleavage furrow ingression , the dynamics of CYK-4 localization in live embryos was investigated. To accomplish this goal a transgenic line expressing a CYK-4:GFP fusion was generated and its localization followed by time lapse microscopy. The CYK-4:GFP fusion is partially functional since cyk-4 xsEx1[cyk-4:GFP] animals are viable and fertile at 25° C. whereas the parental cyk-4 strain is inviable at 25° C. However, the fusion construct does not fully rescue the mutation, since about 40% of embryos produced by this line fail to hatch (table 1).

Low light level fluorescence microscopy was used to visualize CYK-4:GFP in living embryos. Embryos were imaged using a multi-mode imaging system whereby a series of z-sections and a nomarski image were recorded every 10 seconds. The fluorescent images from each time point were projected to form a single image.

Figure 8:
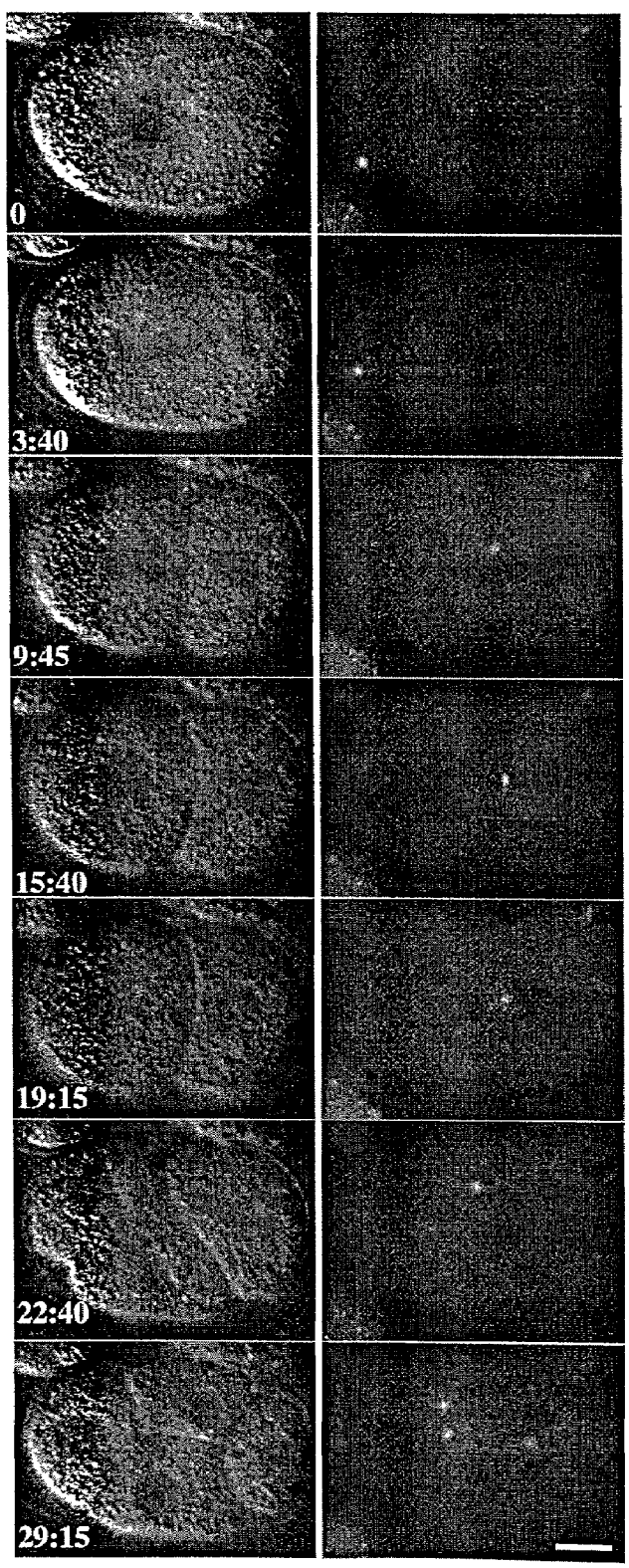
FIG. 8: Time lapse analysis of CYK-4:GFP.

FIG. 8 shows the time lapse analysis of CYK-4:GFP. An embryo from a line expressing CYK-4:GFP was imaged using low light level microscopy. The central spindle localization of CYK-4 is observed prior to furrow ingression. 10 µm scale bars.

These recordings reveal that CYK-4 accumulates on the central spindle prior to the initiation of furrowing (FIG. 8; 3:40). The CYK-4 that localizes to the central spindle becomes compressed into a bright spot which persists at the division remnant. The remnant persists for several cell cycles although instances were observed whereby the remnant (sometimes from the polar body) detaches from the cortex and is observed as a discrete spot in the cytoplasm. This detachment of CYK-4 from division remnants likely accounts for the CYK-4 rings seen in fixed specimens. It is concluded that CYK-4 localization on the central spindle precedes furrow ingression.

EXAMPLE 5

Cyk-4 and Zen-4/CeMklp1 are Functionally Interdependent

There are remarkable similarities between CYK-4 and the kinesin-like protein ZEN-4/CeMKLP1 (Powers et al., 1998; Raich et al., 1998). zen-4 mutant embryos also initiate, but fail to complete cytokinesis. They also fail to assemble a robust central spindle in early anaphase. Furthermore, ZEN-4 localizes to the central spindle and persists at division remnants after completion of cytokinesis. To test whether these proteins functionally interact, it was first assessed whether CYK-4 and ZEN-4/CeMKLP1 co-localize.

Embryos expressing CYK-4:GFP were fixed and CYK-4 and ZEN-4 were localized simultaneously (using an anti-GFP antibody to detect CYK-4:GFP). The two proteins co-localize both on central spindle structures and on division remnants (FIGS. 9A–C). It was next investigated if ZEN-4 localization requires functional CYK-4 protein. ZEN-4 staining of cyk-4 mutant embryos reveals that ZEN-4 localization to the central spindle is absent (FIG. 9E), although staining of some microtubule bundles in the spindle midzone could be detected using an AIR-2 antibody (FIG. 9G). Thus, recruitment of ZEN-4 to the central spindle is CYK-4 dependent.

Figure 9:
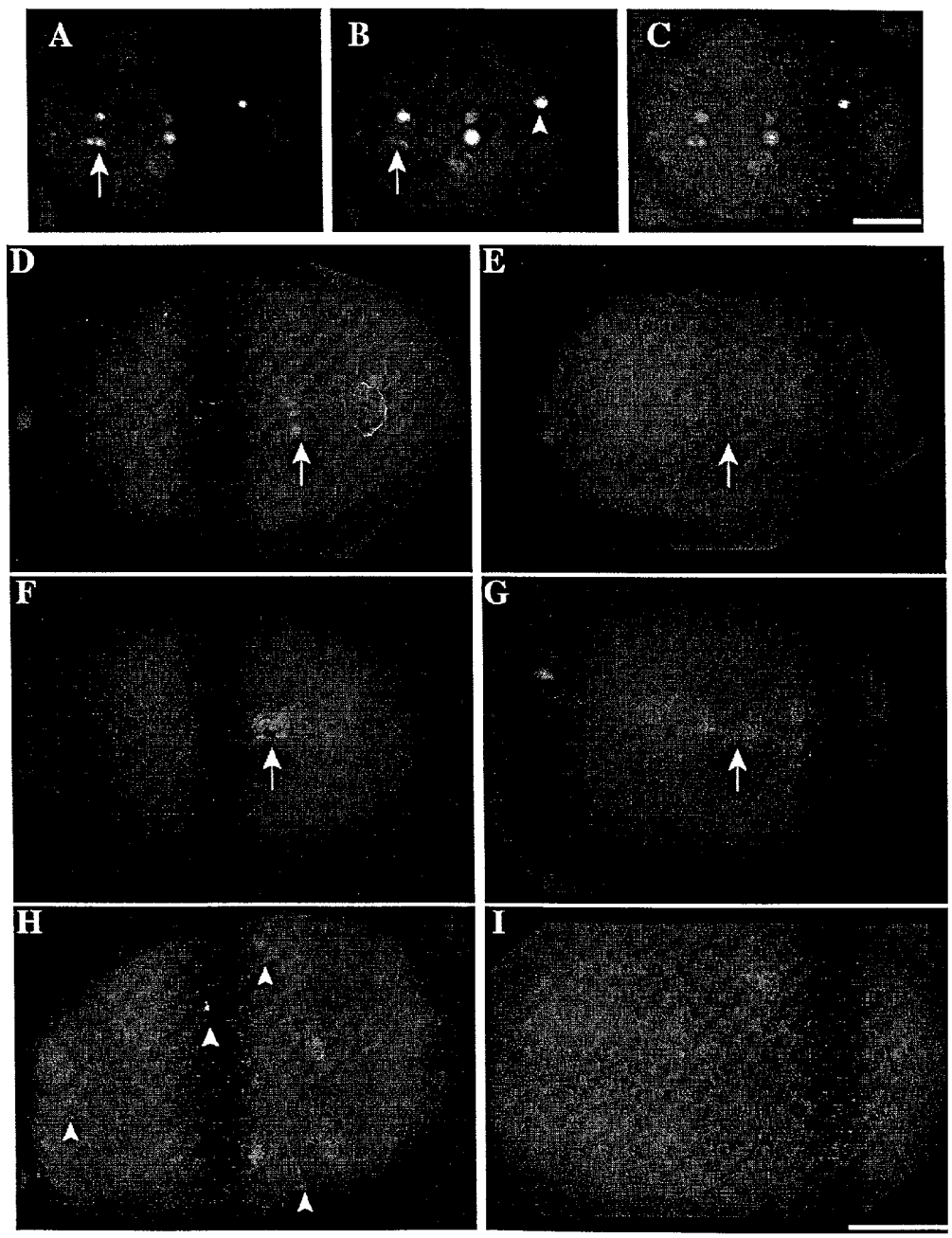
FIG. 9: CYK-4 and ZEN-4/CeMKLP1 colocalize and are interdependent for their localization.
Figure 10:
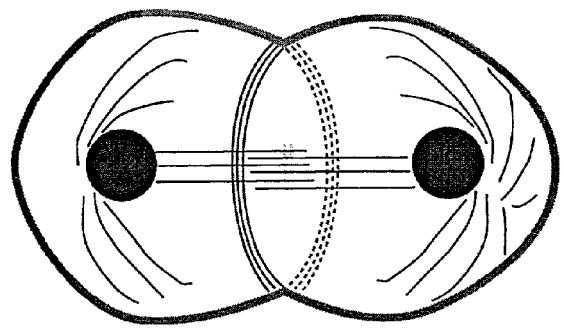
FIG. 10: Model for the function of CYK-4 in central spindle formation and cytokinesis.
Figure 10:
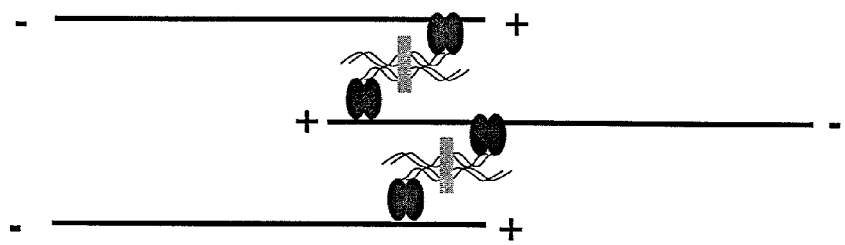
Figure 10:
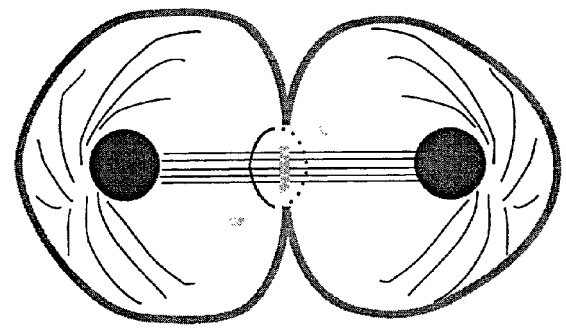
Figure 10:
Figure 10:

FIG. 9 shows an embryo expressing CYK-4:GFP stained for GFP (A), ZEN-4/CeMKLP1 (B) and the merged image (C). CYK-4 and ZEN-4/CeMKLP1 colocalize at division remnants (arrow) and a central spindle (arrowheads) structures. ZEN-4 localization to the central spindle is CYK-4 dependent (arrow). Wild-type (D) and cyk-4(t1689ts) embryos (E) were fixed and stained for ZEN-4/CeMKLP1 (green), tubulin (red) and DNA (blue). AIR-2 localization to the central spindle is CYK-4 independent (arrow). Wild-type (F) and cyk-4(t1689ts) embryos (G) were fixed and stained for AIR-2 (green), tubulin (red) and DNA (blue). CYK-4 maintenance to division remnants (arrowheads) is ZEN-4/CeMKLP1 dependent. zen-4(or153ts) worms were maintained at 16° C. and either fixed immediately (H) or shifted to 25° C. for 18 minutes (I). Embryos were fixed and stained for CYK-4 (green), tubulin (red) and DNA (blue). 10 μm scale bars.

Next it was tested whether maintenance of ZEN-4 at division remnants requires functional CYK-4. cyk-4 mutant embryos grown at 16° C. were shifted to 25° C. for 15 minutes prior to fixation and staining with anti-ZEN-4 antibodies. The number of cells and number of division remnants labeled with the anti-ZEN-4 antibody were counted. Embryos maintained at the permissive temperature had a large number of ZEN-4 staining division remnants (table 3) whereas the embryos shifted to the non-permissive temperature lacked defined staining of division remnants. Thus both recruitment of ZEN-4 to the central spindle and its maintenance at division remnants is CYK-4 dependent. The reverse experiment was conducted with a temperature sensitive allele of zen-4(or153ts). In this case CYK-4 staining at division remnants was observed in zen-4 mutant embryos at the permissive temperature but this staining disappeared upon a brief shift to the non-permissive temperature (FIGS. 9H,I and table 3). Thus maintenance of CYK-4 at division remnants is ZEN-4 dependent. It is concluded that CYK-4 and ZEN-4/CeMKLP1 colocalize and that the two proteins are interdependent for their localization.

Next, it was determined if embryos carrying mutations in both cyk-4 and zen-4 are distinguishable from the single mutants. Two strains were built, one strain was homozygous for zen-4(or153ts) and heterozygous for cyk-4(t1689ts) and the second strain was homozygous for cyk-4(t1689ts) and heterozygous for zen-4(or153ts). Both strains were viable at 16° C., but they failed to produce doubly homozygous larvae. It was found that worms of genotype unc-32(e189) cyk-4(t1689ts)/qC1 III, zen-4(or153ts) laid a fraction of embryos that arrested during embryonic development, typically before the comma stage. Thus cyk-4(t1689ts) and zen 4(or153ts) are synthetically lethal.

In the subsequent Examples, the following Materials and Methods were used:

i) Worm Strains and Alleles

The following alleles were used: N2(Bristol), CB4856, cyk-4(t1689ts), unc-64, bli-6(sc16), unc-24(e138), unc-44 (e1260), lag-1 (q385), and mIs11 IV. Some strains were obtained from the *C. elegans* Genetics Center.

ii) Isolation and Mapping of cyk-4 Suppressor Alleles

Suppressors of the cyk-4(t1689ts) mutation were obtained by mutagenizing cyk-4(t1689ts) animals with 30–40 mM EMS or 0.5 mM ENU. P0 animals were allowed to self fertilize for two generations at the permissive temperature. When F2 animals reached early adulthood, the population was shifted 20° C. and fertile animals were selected. Approximately 110,000 F1 genomes were screened and 18 suppressor mutations, all but 2 being unambiguously independent, were isolated. While all of the suppressor strains were viable and fertile at 20° C., none were able to grow at 25° C., suggesting that none of them precisely reverted the original mutation. Several intragenic suppressor mutations were identified. The ZEN-4 coding region of the remaining mutants were sequenced and 7 strains were found to contain substitutions within the CYK-4 binding region of ZEN-4 and one contained a substitution in the catalytic domain. One suppressor strain, xs82, was characterized in detail. Suppressor activity was mapped using single nucleotide polymorphisms (SNPs) to the central region of chromosome IV (see methods). The ZEN-4 coding region was sequenced in this strain and a point mutation was found that causes a substitution of glutamic acid for a lysine at position 502 (FIG. 15A).

iii) Cell Culture

HeLa cells were routinely grown in Dulbecco's modified Eagle's medium (DMEM), supplemented with 10% fetal calf serum, 2 mM L-glutamine, 100 U/ml penicillin, 100 mg/ml streptomycin.

iv) Antibodies

Rabbit CYK-4 specific and ZEN-4 specific antisera were reported previously (Jantsch-Plunger et al., 2000). CYK-4 and ZEN-4 antibodies were affinity-purified with His6-CYK-4 (407–613) or His6-ZEN-4 (578–775) immobilized on NHS-Sepharose (Pharmacia).

MKLP-1 specific antisera and HsCYK-4 specific antisera were produced in rabbits and mice (Gramsch Laboratories, Schwabhausen, Germany) using C-terminal peptides (QLG-PGYQHHAQPKRKKP and SKSKSATNLGRQGNFFASP-MLK, respectively) conjugated to keyhole limpet hemocyanin as immunogens. Rabbit antibodies were affinity purified using peptides immobilized on Poros epoxide resin.

v) Plasmids

A cDNA clone for ZEN-4 in pBluescript (yk391b3) which lacks 13 nts at 5' of the coding region which were introduced by PCR. The PCBD-TEV vector was constructed by inserting the sequences encoding the chitin-binding domain (CBD) and a TEV protease site into pET28a (Novagen). ZEN-4 fragments were amplified by PCR and cloned into pCBD-TEV.

vi) In Vitro Binding Assay

Full length and fragments of CYK-4 and ZEN-4 were expressed by in vitro transcription and translation system with reticulocyte lysates using the TNT® Coupled Reticulocyte Lysate Systems (Promega) or the PROTEINscript™

II (Ambion) kits, typically in 20 µl reactions. Full length proteins without tag were expressed from the T3 promoter of pBluescript SK(−). Fragments of CYK-4 and ZEN-4 tagged with chitin-binding domain (CBD) at N-terminus were expressed from the T7 promoter of pET-CBD. In some experiments (FIGS. 12C, 13C and 16), CYK-4 and ZEN-4 were co-expressed in the same reactions. In other experiments, they were separately expressed and mixed. Following incubation at 20° C. for 30 min in 100 µl buffer A (20 mM Hepes, 150 mM NaCl, 2 mM $MgCl_2$, 10 mM EDTA, 1 mM DTT, 1 mM PMSF, 10 µg/ml leupeptin, 10 µg/ml pepstatin, 10 µg/ml chymostatin) with 0.5% (w/v) Triton X-100, ZEN-4 or CYK-4 proteins were immunoprecipitated with specific antibodies, or affinity-purified by chitin beads. For immunoprecipitation, 0.5 µg antibody was added to the reactions and incubated on ice for 1 hr, followed by incubation with 5 µl protein A-Sepharose beads at 4° C. for 1 h. For CBD-affinity purification, 5 µl of chitin beads (New England Biolabs) were added. In both cases, the beads were washed three times with buffer A containing 0.5% (w/v) Triton X-100. Proteins bound to the beads were analyzed by SDS-PAGE followed by autoradiography with PhosphoImager.

vii) Preparation of Cell Lysates

C. elegans embryos were prepared by bleaching a synchronous culture of adult worms grown on "egg plates" as described (Lewis and Fleming, 1995). The embryos were washed with buffer A without Triton-X 100 and frozen with liquid nitrogen and kept at −80° C. until use. Embryos were crushed by grinding in a mortar and pestle in liquid nitrogen.

HeLa cells were synchronised by treatment with 0.1 µg/ml nocodazole for 16 h. Cells were washed twice with cold PBS, frozen by liquid nitrogen and kept −80° C. until use. Cells were lysed and thawed by suspending into 10 volumes of buffer A with 0.5% (w/v) Triton X-100.

viii) Preparation of Microtubule-binding Fraction

Frozen pellet (0.5 ml) of nocodazole arrested M-phase cells was thawed and lysed in 5 ml ice-cold BRB80 (80 mM K-Pipes, 1 mM $MgCl_2$, 1 mM EGTA, pH 6.8) with 0.1% (w/v) Triton X-100. The lysate was clarified by centrifuging at 10,000× g for 15 min. The resulting supernatant was centrifuged at 25,000×g for 20 min at 4° C. in S100AT6 rotor (Hitachi). Microtubules polymerized with glycerol and taxol was added to the supernatant. After incubating at 20° C. for 20 min, microtubules were pelleted by centrifuging at 25,000×g for 20 min at 20° C. The bound proteins were released from microtubules by incubation in 0.5 M NaCl, 5 mM ATP in BRB80 at 20° C. for 20 min, followed by centrifugation at 25,000×g for 20 min at 20° C.

ix) Mass Spectrometry Analysis

Hydrodynamics

Sedimentation coefficient was estimated by ultracentrifugation through 2 ml linear gradient of 5 to 20% (w/v) sucrose in buffer A without Triton X-100 using S55S rotor (Hitachi). 150 µl cell lysate or microtubule binding fraction was applied. Chicken ovalbumin (3.4 S), bovine gamma globulin (7.1 S), bovine catalase (11 S) and bovine thyroglobulin (19 S) were used as standards. The diffusion coefficient was estimated by gel filtration using Superdex 200 column (30 ml) in FPLC system (Pharmacia).

Immunoprecipitation and Western Blotting

Lysates (500 µl) were precleared with 50 µl protein A-Sepharose beads. For immunoprecipitation from worm embryos, 1 µg affinity-purified anitibody was added to the lysate. After incubation on ice for 1 hr, immunocomplex was recovered by incubation with 5 µl protein A-Sepharase (Pharmacia) at 4° C. for 1 hr. For immunoprecipitation from HeLa cells, antibodies were covalently immobilized on protein A-beads (1 µg per 1 µl beads) with dimethyl pimelimidate. The precleared lysate was incubated antibody-beads at 4° C. for 1 to 4 h. The beads were washed briefly with buffer A plus 0.5% Triton X-100 three times.

For western blotting, samples were run on 7.5% SDS-PAGE gel and electrotransfered to a nitrocellulose membrane (HiBond ECL, Amersham).

x) Immunolocalization

Immunolocalization studies in worm embryos were performed as previously described ref. In brief, gravid hermaphrodites were placed on aminopropyl-silane treated slides, a coverslip was added, and sufficient pressure to extrude the embryos was applied (Jantsch-Plunger et al., 2000). The slide was placed into liquid nitrogen. The coverslip was removed while the sample was still frozen, the preparation was fixed with −20° C. methanol, and antibody staining was performed according to standard procedures. Immunolocalization studies using HeLa cells were performed according to standard procedures following fixation in −20° C. methanol.

EXAMPLE 6

Central Spindle Assembly is Independent of RhoA

The process of central spindle assembly is dependent on the RhoGAP protein CYK-4. In the previous Examples, it was found that RhoA is essential for cytokinesis while Rac and Cdc42 are not (Jantsch-Plunger et al., 2000). Since RhoA is required for cytokinesis, it was tested if this GTPases is also required for central spindle assembly. To inactivate RhoA worms were grown on bacteria expressing dsRNA from the coding region of the gene (Timmons and Fire, 1998). Embryos were fixed and immunoflorescence-stained for CYK-4, microtubules and DNA with anti-CYK-4 antibody, anti-α-tubulin antibody and Hoechst 33342). In both control embryos and rhoA(RNAi) embryos, central spindles formed and were prominently labeled with anti-CYK-4 antibodies.

Figure 11:
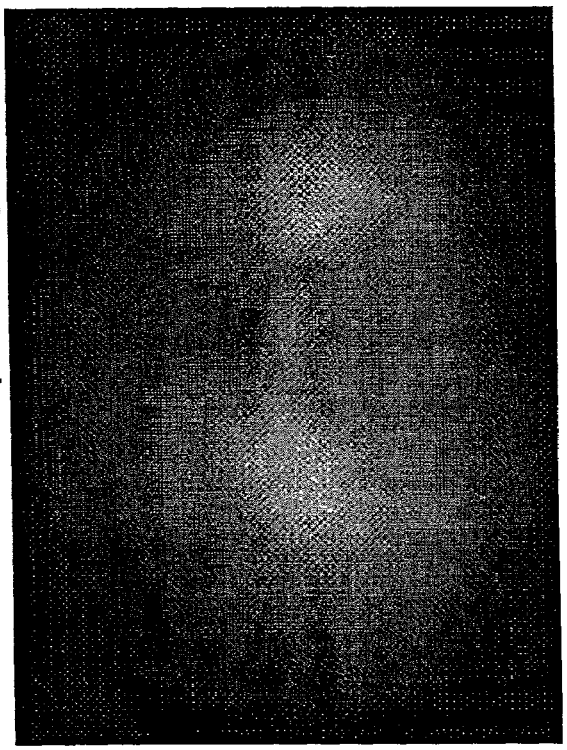
FIG. 11: RhoA does not have a role in the formation of central spindle
Figure 11:
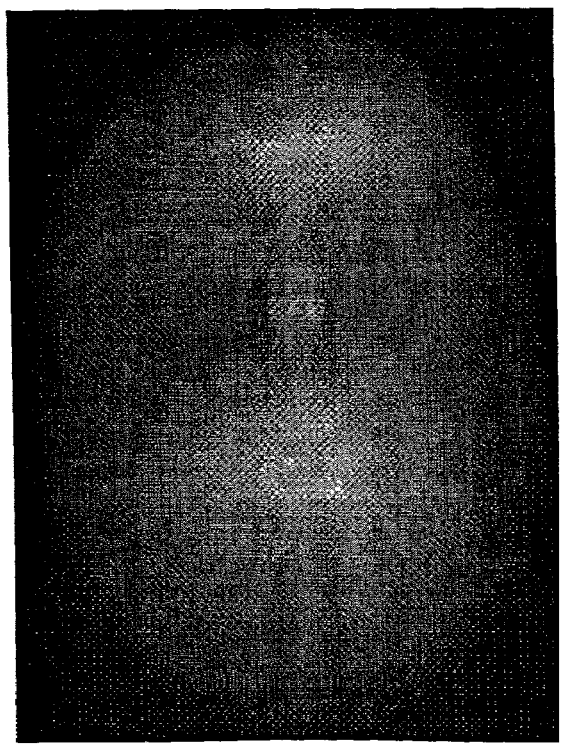

Although RhoA dsRNAi causes a fully penetrant inhibition of cytokinesis, central spindle assembly occurs normally, and CYK-4 localizes to the central spindle (FIG. 11). Thus the requirement for RhoA in cytokinesis can not be accounted for by a requirement for RhoA in central spindle assembly. These data indicate that the requirement for CYK-4 in central spindle assembly is independent of its ability to regulate RhoA.

EXAMPLE 7

CYK-4 and ZEN-4 Form a Complex in vivo and in vitro

Since central spindle assembly and cytokinesis requires both CYK-4 and ZEN-4 and these two proteins are interdependent for their proper localization, it is possible that these factors exist in a stable biochemical complex. In order to test this possibility, immunoprecipitation experiments were performed using extracts prepared from early C. elegans embryos. When embryo extracts were immunoprecipitated using anti-CYK-4 antibodies, it was found that significant amount of ZEN-4 co-immunoprecipitated suggesting the existence, in vivo, of a stable complex containing CYK-4 and ZEN-4 (FIG. 12A).

To determine whether CYK-4 and ZEN-4 are competent to interact in the absence of other nematode proteins, the two proteins were produced by in vitro translation and subjected to immunoprecipitation. When CYK-4 and ZEN-4 (fused to the chitin binding domain (CBD)) were translated in vitro and subsequently mixed, both proteins could be recovered in high yield by chitin beads (FIG. 12B). The co-precipitation of CYK-4 was dependent on ZEN-4; CYK-4 was not recovered on chitin beads when ZEN-4 was substituted by CBD alone. Moreover, when luciferase was substituted for CYK-4, it did not co-precipitate with ZEN-4. The association between CYK-4 and ZEN-4 could also be detected when anti-CYK-4 antibodies were used to retrieve the complex (FIG. 12C).

Figure 12:
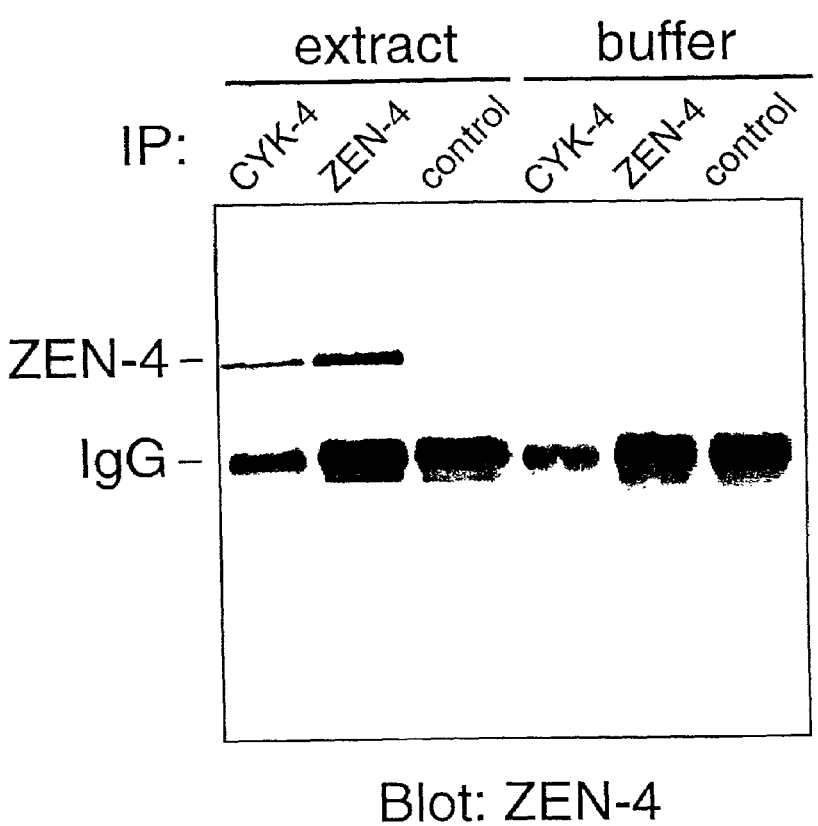
FIGS. 12A–12C: CYK-4 and ZEN-4 associate in vivo and in vitro
Figure 12:
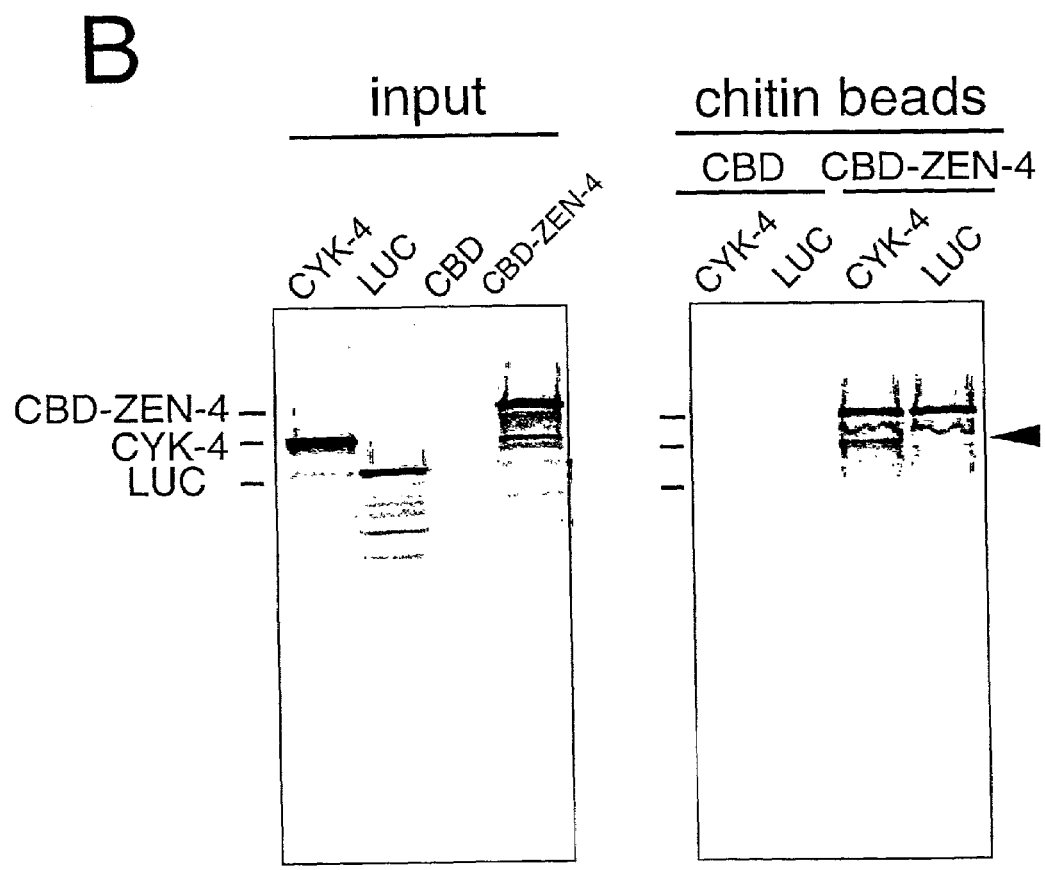
Figure 12:
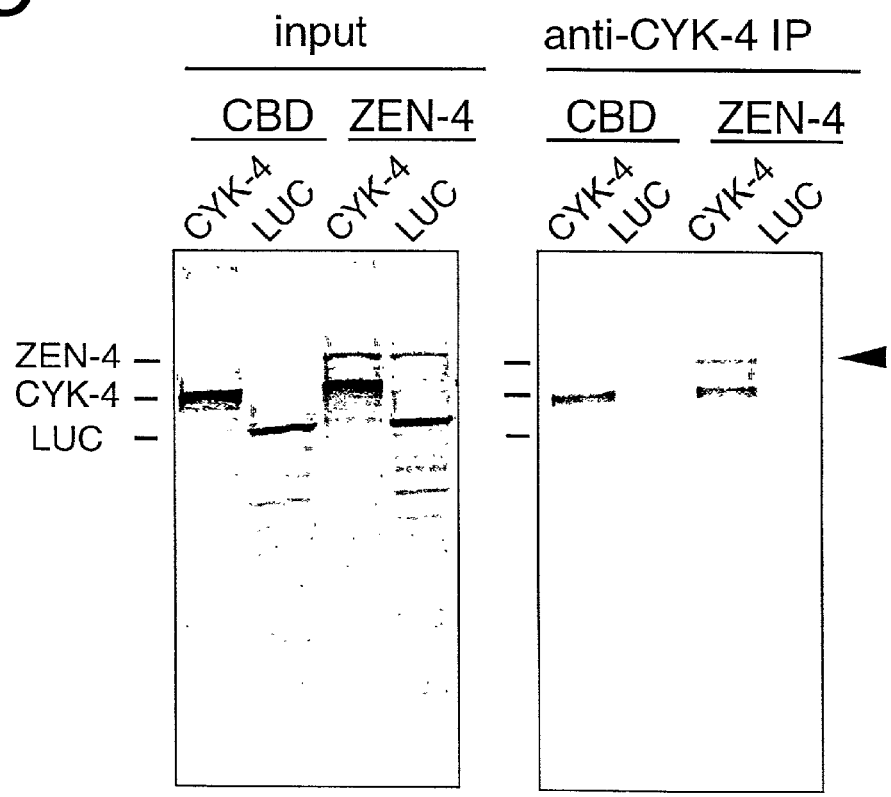

FIG. 12 shows that CYK-4 and ZEN-4 bind to each other in vivo (A) and in vitro (B and C). (A) CYK-4 and ZEN-4 were immunoprecipitated from worm embryo extracts with anti-CYK-4 antibody, anti-ZEN-4 antibody, or with non specific rabbit IgG as a control. The immunoprecipitates were resolved on SDS-PAGE gels followed by western blotting with an anti-ZEN-4 antibody. Mock immunoprecipitation without extract was included to control for cross reactivity with the antibodies. ZEN-4 specifically co-immunoprecipitated with CYK-4. (B) $^{35}$S-labeled CYK-4 (or luciferase, LUC) and chitin-binding domain (CBD)-tagged ZEN-4 (or CBD alone) were separately expressed by in vitro translation (left panel). Translation reactions were mixed and incubated in the indicated combinations and CBD-ZEN-4 or CBD alone were recovered with chitin beads (right panel). In this and all gels in this paper the input lanes contain the same amount of translation product as was added to the beads used for precipitation. The precipitates were resolved on SDS-PAGE gels and the labeled products detected using a phosphoimager. CYK-4 co-purified with CBD-ZEN-4 while the luciferase control did not. (C) CYK-4 (or luciferase) and CBD-ZEN-4 (or CBD alone) were co-expressed as $^{35}$S-labeled proteins in the indicated combinations (left panel). CYK-4 was immunoprecipitated with an anti-CYK-4 antibody (right panel). ZEN-4 co-immunoprecipitated with CYK-4 .

EXAMPLE 8

Delineation of the Region of CYK-4 Necessary to Bind to ZEN-4

Since the binding between CYK-4 and ZEN-4 could be easily reconstituted using in vitro translated proteins, this simple assay was used to dissect the regions of the two proteins that mediate this interaction. The experiment first concentrated on CYK-4. The N-terminal 30 amino acids of CYK-4 are poorly conserved and are followed by a 90 amino acid region predicted to form a coiled-coil (see schematic FIG. 13D). The C-terminal 250 amino acids contains a RhoGAP domain that is active in vitro against RhoA, Rac, and Cdc42 (Jantsch-Plunger et al., 2000). The RhoGAP domain is preceded by a C1 domain, a cysteine-rich domain that mediates interactions with diacylglycerol (Hurley and Meyer, 2001) other ref. Truncations of the C-terminus of CYK-4 revealed that the ZEN-4 binding region is contained within the N-terminal 232 amino acids (FIG. 13A). Further truncations within this region indicated that residues 1–120 (from the N-terminus to the end of the coiled-coil region) are sufficient to bind efficiently to ZEN-4 (FIG. 13B). Deletion of the N-terminal 35 amino acids of CYK-4 prevented the interaction with ZEN-4. A near full length version of CYK-4 lacking only the N-terminal 35 amino acids does not bind ZEN-4 (FIG. 13C). Thus the ability of CYK-4 to interact with ZEN-4 depends on the N-terminal 120 residues of CYK-4 (FIG. 13D).

Figure 13:
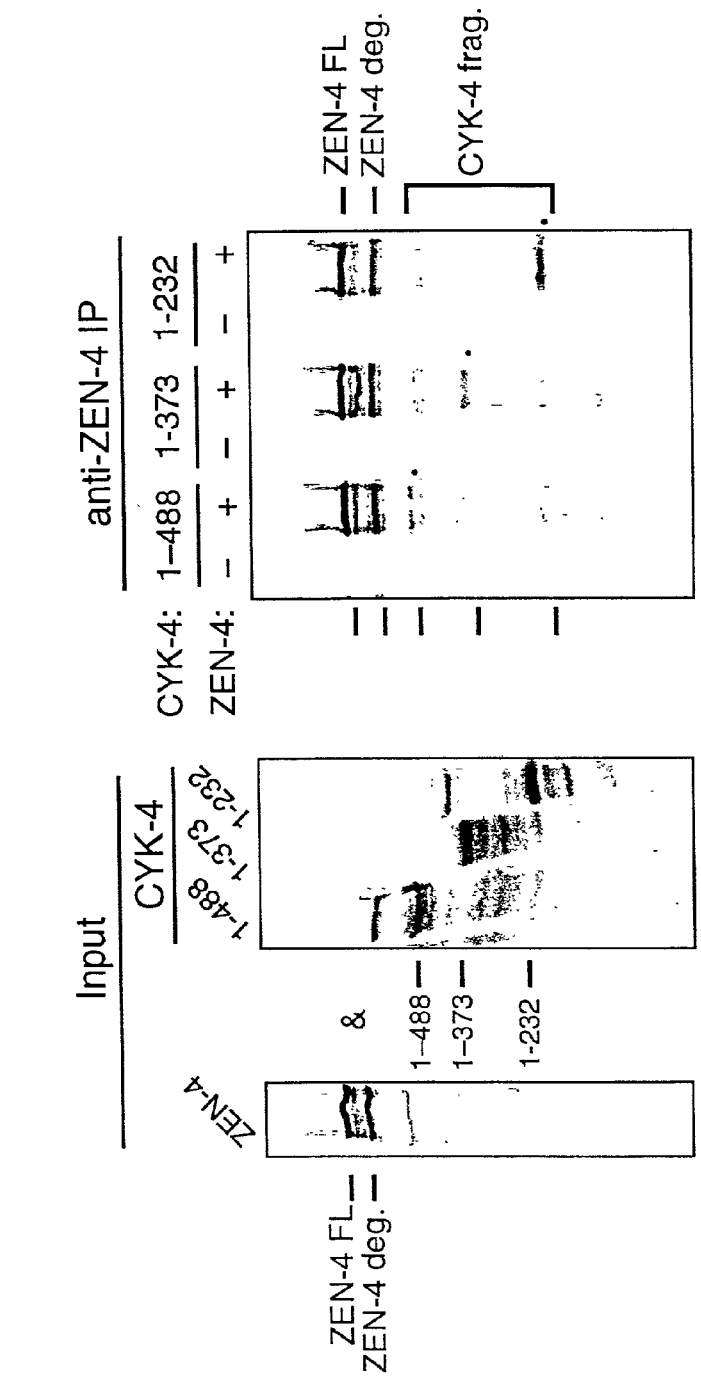
FIGS. 13A–13D: The N-terminus of CYK-4 is necessary and sufficient to bind to ZEN-4
Figure 13:
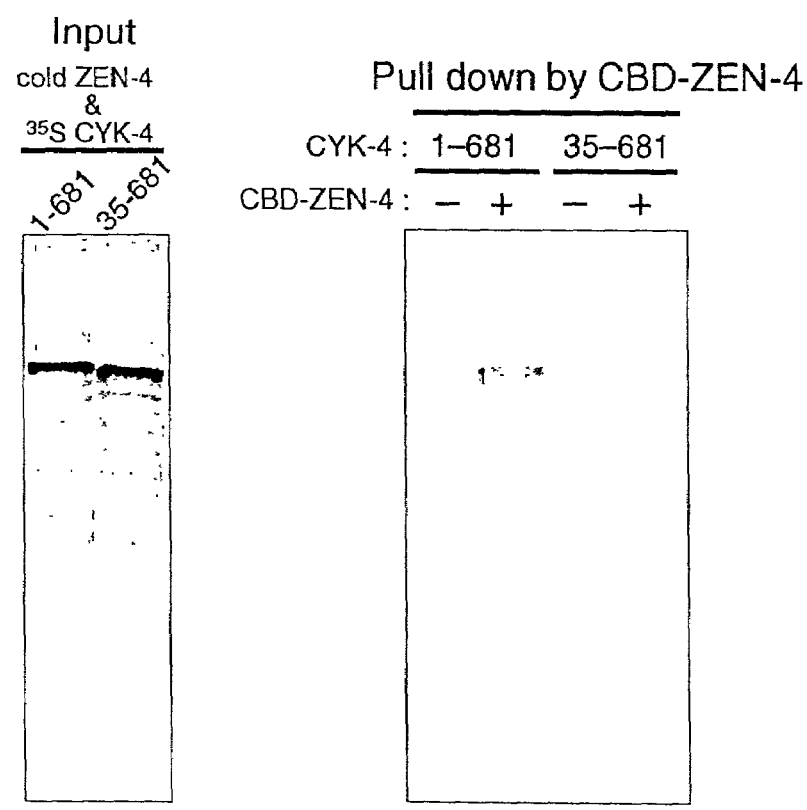
Figure 13:
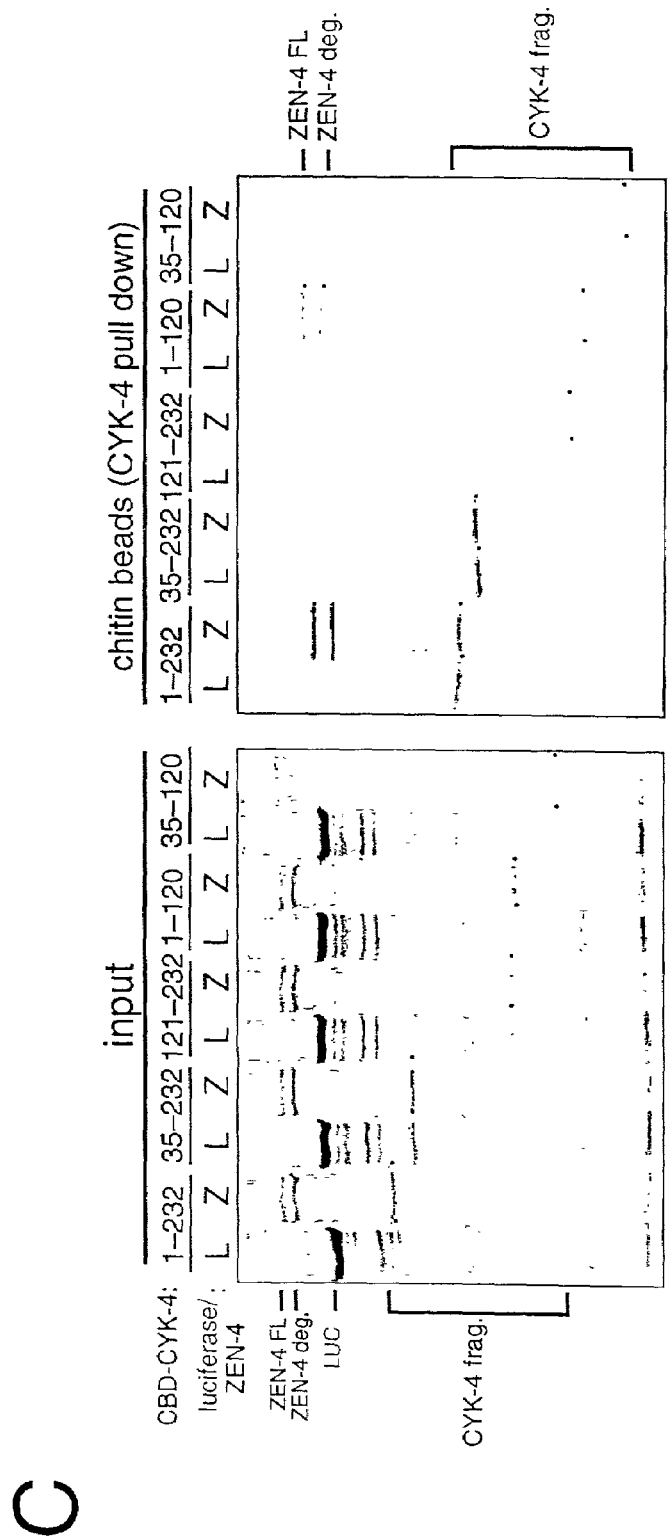
Figure 13:
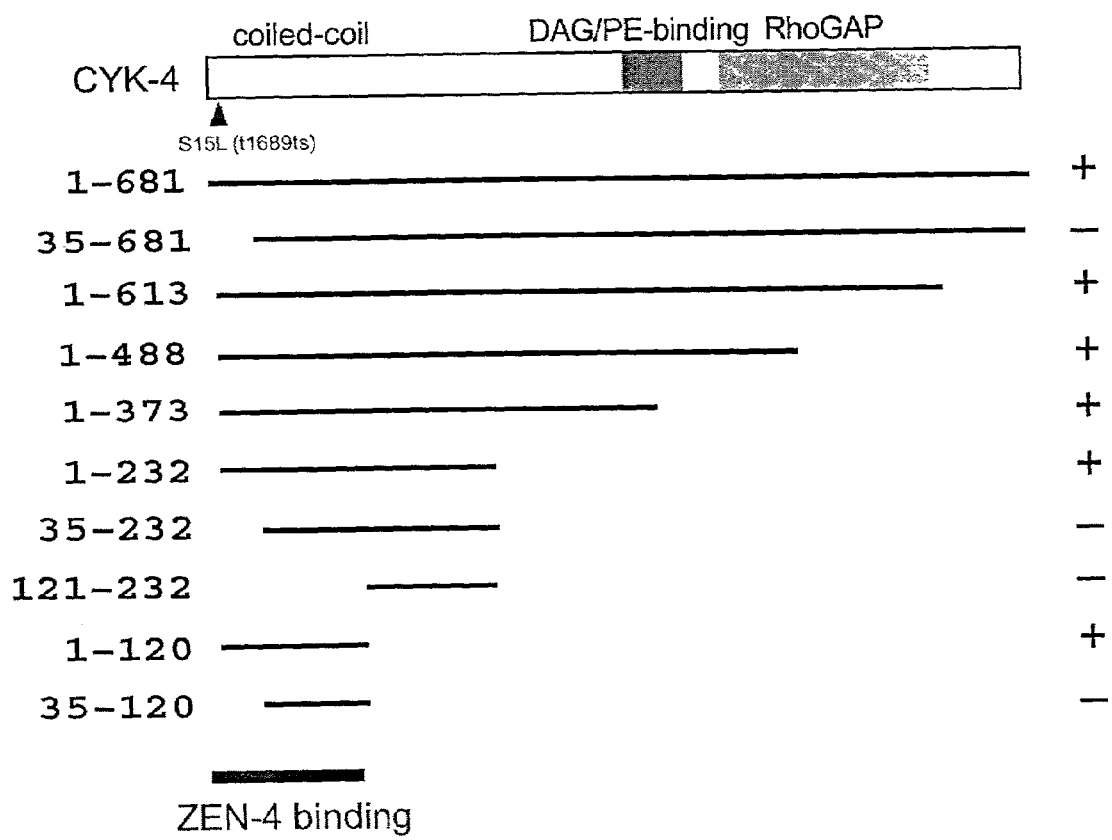

FIG. 13 shows the results of the in vitro binding assay that was used to define the ZEN-4 binding region of CYK-4.

(A) Full-length ZEN-4 and C-terminal deletion fragments of CYK-4 (1–232, 1–373 and 1–468) were separately expressed as $^{35}$S-labeled proteins by in vitro translation (left two panels). The reaction products were mixed and after incubation ZEN-4 was immunoprecipitated with an anti-ZEN-4 antibody (right panel). The three fragments of CYK-4 co-immunoprecipitated with ZEN-4. (B) Full length CYK-4 (1–681) and CYK-4 with N-terminal deletion (35–681) were expressed as $^{35}$S-labeled proteins and mixed with unlabeled CBD-ZEN-4 (left panel). After incubation, CBD-ZEN-4 was affinity purified on chitin beads (right panel). CYK-4 (35–681) did not copurify with CBD-ZEN-4, but full length CYK-4 did. (C) CBD-CYK-4 fragments (1–232, 35–232, 121–232, 1–120 and 35–120) and full length ZEN-4 (or luciferase as a control) were co-expressed as $^{35}$S-labeled proteins by in vitro translation (left panel). CBD-CYK-4 fragments were affinity purified (right panel). ZEN-4 copurified with CYK-4 (1–232) and (1–120), but not with CYK-4 (35–232), (121–232) or (35–120). (D) A schematic summary of the CYK-4 derivatives tested. The ZEN-4 binding region was defined as residues 1–120 of CYK-4. This region contains a coiled coil region and a N-terminal extension.

EXAMPLE 9

Delineation of the ZEN-4 Region Required to Bind CYK-4

Next, the in vitro assay was used to define the region of ZEN-4 that binds to the N-terminal binding of CYK-4. Initially the CYK-4 binding activity of full length ZEN-4 was compared to that of three C-terminal deletion fragments of ZEN-4: the N-terminal catalytic core alone (1–434), the catalytic core domain and the linker region (1–507), and a longer derivative that also includes the coiled coil domain (1–603). The full length protein bound CYK-4 with high affinity, as did the next longer fragment (1–603), but the two smaller fragments did not interact with CYK-4 (FIG. 14A). Next it was examined whether the binding activity could be further localized within the central region of ZEN-4. A minimal binding domain consisting of 169 amino acids was defined (FIG. 14B). This region appears to consist of two elements, the linker region and the coiled coil; neither of these individual elements had detectable binding activity on their own.

The interaction of CYK-4 with the neck linker/coiled coil region of ZEN-4 is particularly interesting in light of recent studies that indicate that in conventional kinesin, the neck linker region is critical for transducing chemical energy into mechanical energy (Case et al., 2000; Rice et al., 1999) (see discussion).

Figure 14:
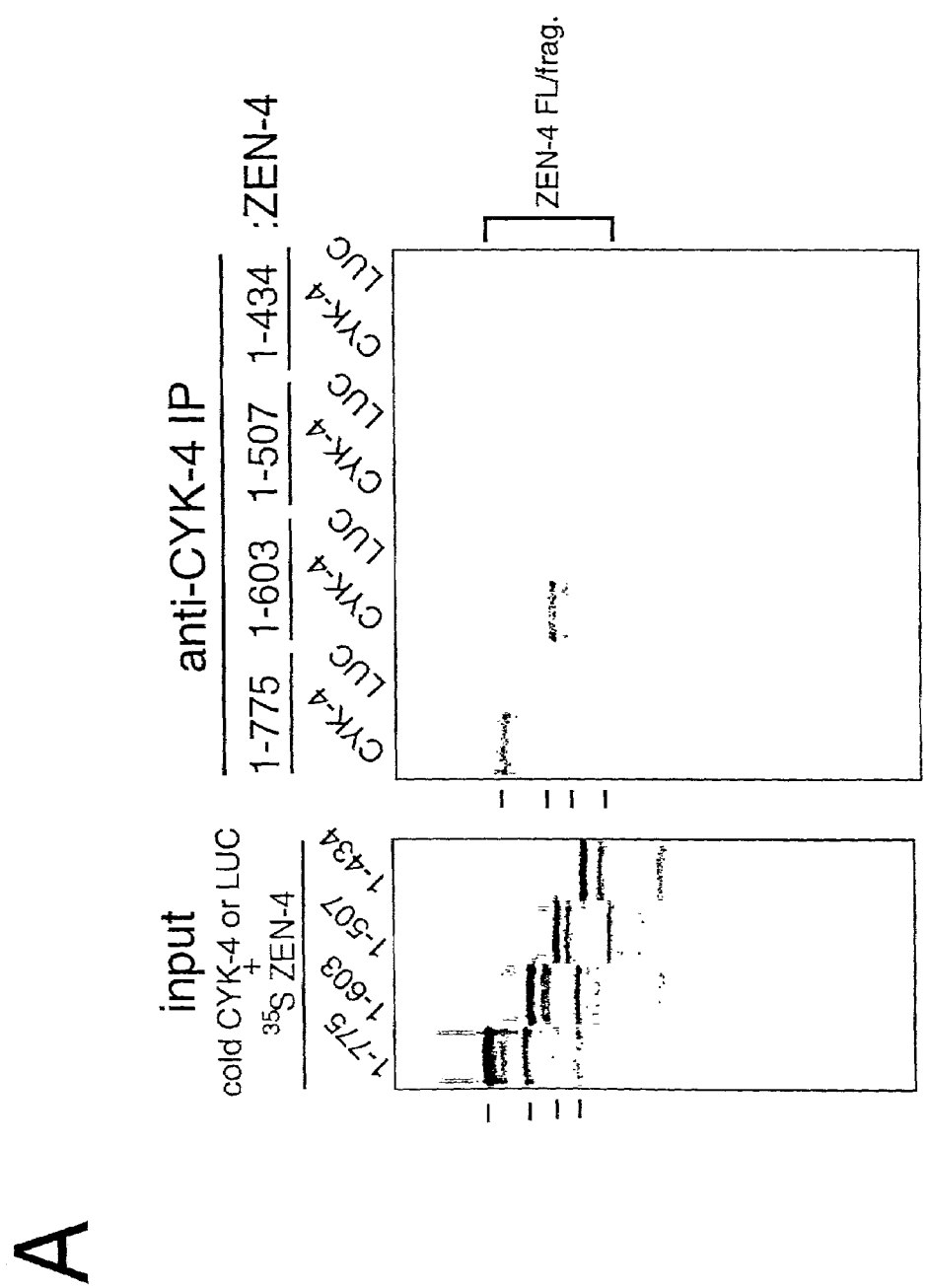
FIGS. 14A–14C: The central region of ZEN-4 is necessary and sufficient to bind to CYK-4
Figure 14:
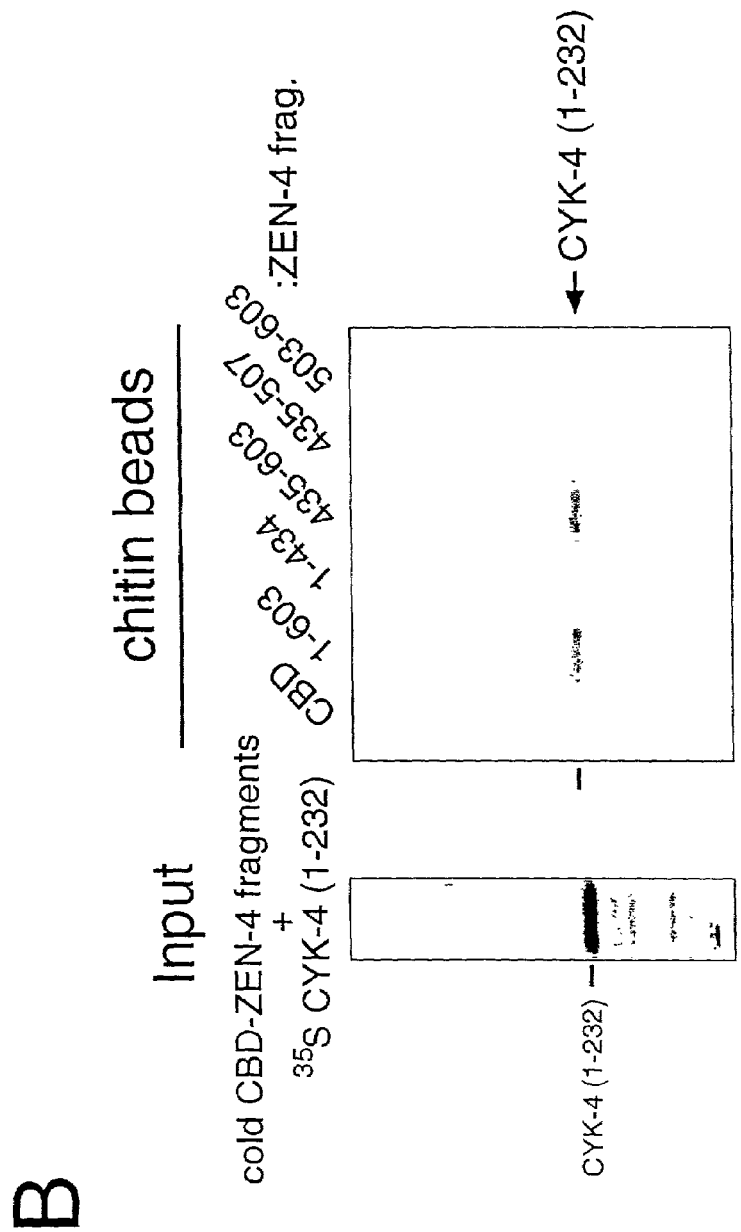
Figure 14:
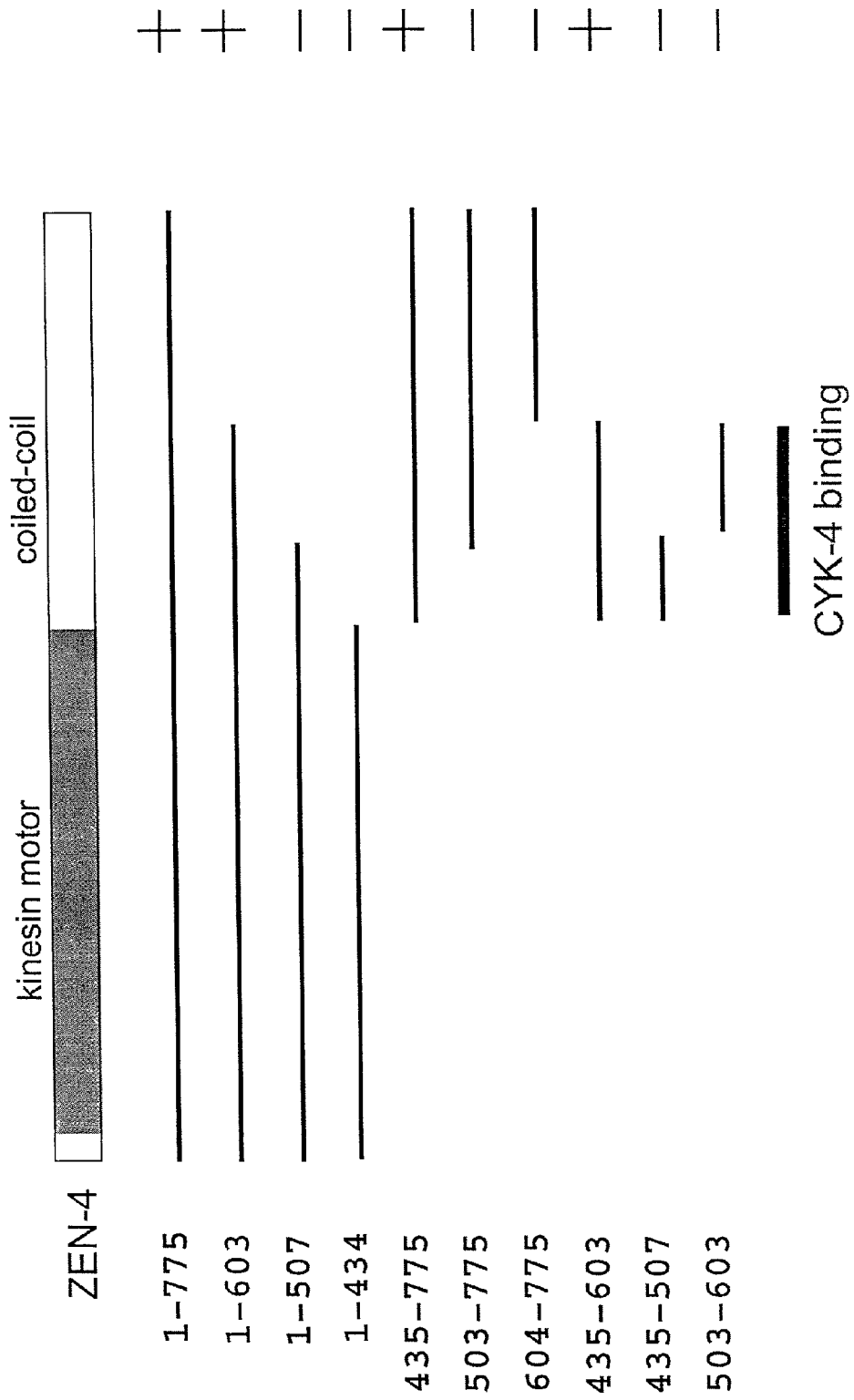

FIG. 14 shows the results of the in vitro binding assay that was used to show that the central region of ZEN-4 is necessary and sufficient to bind to CYK-4.

Full length ZEN-4 (1–775) and C-terminal deletion fragments of ZEN-4 (1–603, 1–507 and 1–434) were $^{35}$S-labeled by in vitro translation and incubated with unlabeled CYK-4 (or luciferase as a control) (left panel). CYK-4 was precipitated with anti-CYK-4 antibody (right panel). Full length ZEN-4 and ZEN-4 (1–603) co-precipitated with CYK-4, while shorter fragments (1–507, 1–434) did not. (B) CBD-tagged fragments of ZEN-4 (1–603, 1–434, 435–603, 435–507 and 503–603) were expressed in an unlabeled form and incubated with $^{35}$S-labeled CYK-4 (1–232) (left panel). ZEN-4 fragments were pulled down by affinity chromatography using chitin beads (right panel). CYK-4 (1–232) copurified with ZEN-4 (1–603) and (435–603), but not with ZEN-4 (1–434), (435–507) or (503–603). (C) A schematic summary of the ZEN-4 derivatives tested. ZEN-4 fragments containing residues (435–603) associate with CYK-4, while the fragments lacking this region did not. This region contains a "neck" region C-terminal to the kinesin catalytic core and a coiled coil region.

EXAMPLE 10 a) The Product of cyk-4(t1689TS) Does Not Interact With ZEN-4.

Although the amino terminal region of CYK-4 exhibits poor sequence conservation at the primary sequence level, earlier studies had indicated that this region is crucial for function since the mutant allele that was used to identify the cyk-4 gene had a Ser to Leu substitution at position 15. Since this point mutation maps into the ZEN-4 binding determinant and since, in vivo, this mutation seems to affect the ability of CYK-4 and ZEN-4 to colocalize, it was tested whether this mutation also affects the ability of these two proteins to interact in vitro. The S15L mutation was introduced into the amino terminal fragment of CYK-4 and used for ZEN-4 binding assays. Whereas an interaction between the N-terminal domain of CYK-4 and the central region of ZEN-4 can be readily detected, the S15L mutant does not interact with ZEN-4 (FIG. 15B). This experiment indicates that the primary cause for the defect in cyk-4(t1689ts) is a defect in the interaction with ZEN-4.

b) In vivo, ZEN-4 is in a Stochiometric Complex With Cyk-4

To gain further insight into the molecular architecture of the CYK-4/ZEN-4 complex and to determine whether a the majority of ZEN-4 is in a complex with CYK-4 in vivo, sucrose density gradient centrifugation experiments were performed with extracts prepared from C. elegans embryos. When wild-type extracts are prepared in the presence of 0.6 M NaCl, ZEN-4 migrates as a symmetrical 9 S peak (FIG. 15C). CYK-4 migrates at an identical S-value (data not shown). To determine whether the migration of ZEN-4 on sucrose gradients was dependent on its association with CYK-4, advantage was taken of the finding that the cyk-4 (t1689) allele is specifically defective in its ability to bind to ZEN-4. When extracts were prepared from cyk-4 mutant embryos and subjected to sucrose density centrifugation, ZEN-4 migrates as a symmetrical peak with a sedimentation value of 6 S, significantly less dense than ZEN-4 sediments in wild type extracts (FIG. 15C). These data indicate that, in vivo, the majority of ZEN-4 is in a complex with CYK-4.

c) In vivo Evidence For the CYK-4/ZEN-4 Interaction Domains

To gain further insight into the mechanism of CYK-4 function in vivo, it was sought to identify extragenic suppressors of the cyk-4(t1689ts) mutation. Homozygous cyk-4(t1689ts) animals were mutagenized and allowed to self fertilize for two generations at the permissive temperature. When the F2 animals reached early adulthood, the temperature was shifted to 20° C. to impose a selection for fertile animals carrying presumptive suppressor mutations. By screening through approximately 100,000 F1 genomes, 18 suppressor mutations were identified (see methods). Intragenic suppressors were identified by sequencing of the cyk-4 locus PCR amplified from suppressor strains. Six suppressor strains contain additional point mutations in the N-terminus of CYK-4; all of the mutations code for amino acid substitutions within the biochemically defined ZEN-4 binding region.

In addition to the mutations found within the cyk-4 gene itself, extragenic suppressor mutations were also identified. One suppressor strain that does not contain any mutations in the cyk-4 gene was characterized in more detail. The suppressor activity was mapped using single nucleotide polymorphisms (SNPs) to the central region of chromosome IV (see methods). Since the zen-4 gene maps to this region, the coding region of the zen 4 gene was sequenced. This strain, xs82, was found to contain a point mutation that causes a substitution of glutamic acid for a lysine at position 502 (FIG. 15A). Importantly, this substitution maps directly to the region of ZEN-4 that was found to mediate the interaction with CYK-4 in vitro. To confirm that the substitution in zen-4(xs82) is responsible for the suppressing activity, the position of the suppressor was mapped to less than 1 cM surrounding the zen-4 locus. This mapping data combined with the fact that the sequence polymorphism maps to the CYK-4 binding region suggests strongly that these point mutations are responsible for the suppressing activity.

To determine whether the substitution, E502K, has any phenotype on its own, in the absence of the cyk-4(t1689) allele, cyk-4(t1689) was crossed out and worms homozygous for zen-4(xs82) were identified. These worms grew normally at 16° C., 20° C., and 25° C.

d) ZEN-4(xs82) Partially Restores Binding to CYK-4 in vitro

As mentioned above, CYK-4 S15L is unable to interact with ZEN-4 in the in vitro binding assay. If the immediate consequence of the S15L substitution in the N-terminus of CYK-4 is defective ZEN-4 binding, then an extragenic suppressor mutation in zen-4 that rescues cyk-4(t1689) might be expected to restore binding to CYK-4 S15L. To test this possibility a N terminal fragment of CYK-4 carrying the S15L point mutation was translated and this product was mixed with a C terminal fragment of ZEN-4 carrying either the wild-type glutamic acid at position 502 or the lysine substitute allele. The wild-type CYK-4 fragment bound equally well to wild-type and the E502K derivative of ZEN-4. As discussed above the CYK-4 S15L is unable to bind to wild-type ZEN-4. However, CYK-4 S15L was able to bind to ZEN-4 E502K, though this interaction was weaker than that seen with the wild-type proteins (FIG. 15A). These data, together with the genetic suppression, prove that the interaction between the N-terminus of CYK-4 and the central region of ZEN-4 is crucial for its function in vivo.

Figure 15:
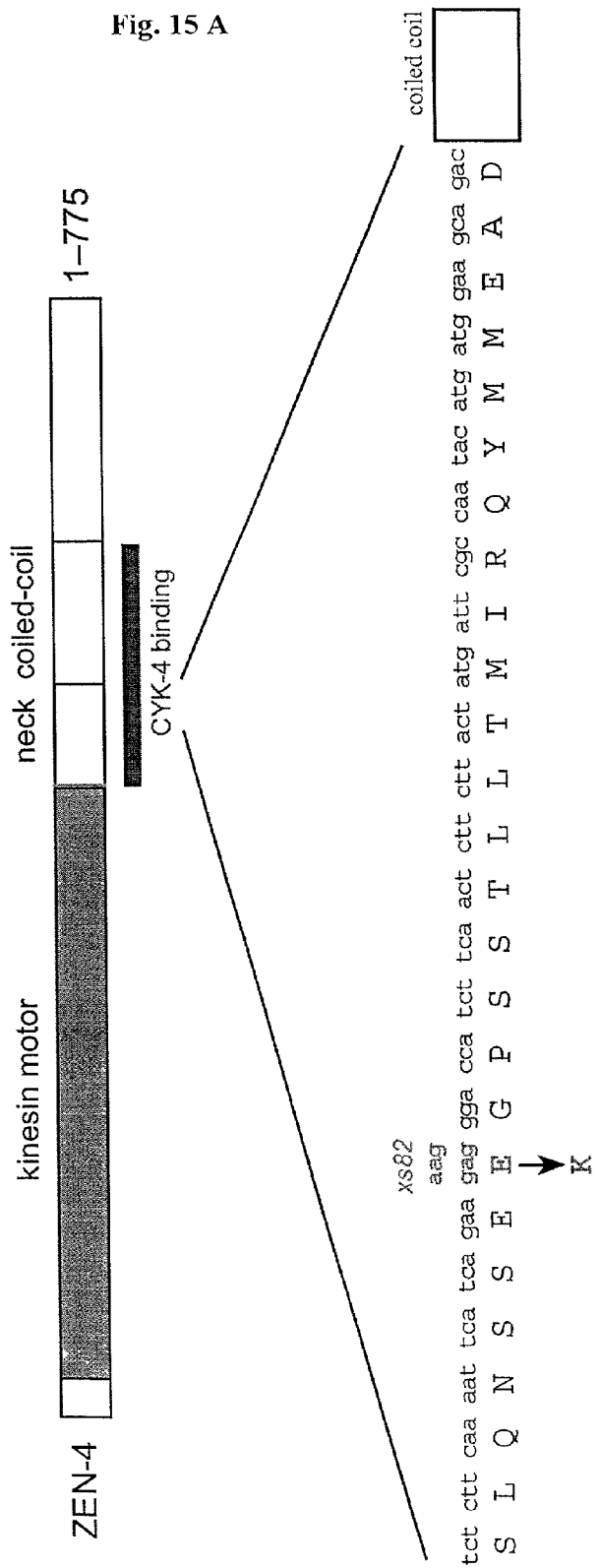
FIGS. 15A–15C: A complex of CYK-4 and ZEN-4 is required for function in vivo
Figure 15:
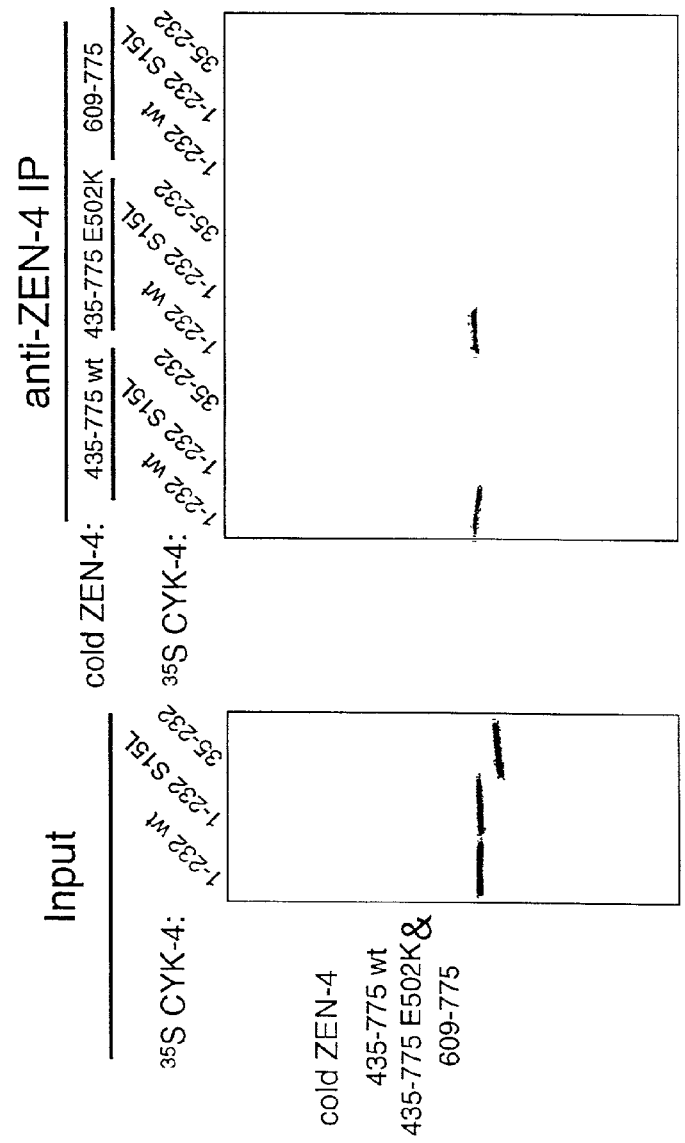
Figure 15:
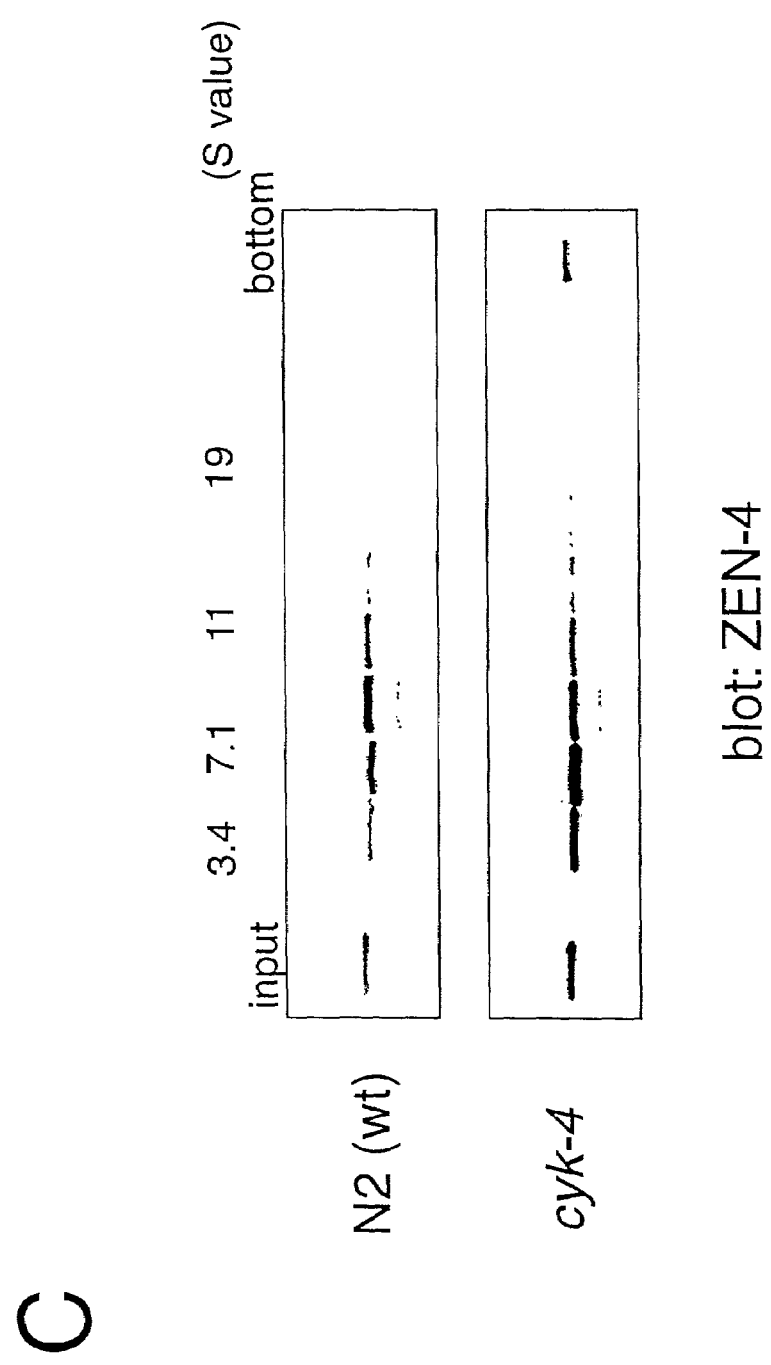

FIG. 15 shows that a complex of CYK-4 and ZEN-4 is required for function in vivo (A) A screen for suppressors of cyk-4(t1689ts) identified a point mutation of zen-4 (xs82). This allele has a G to A point mutation, resulting in substitution of glutamate at residue 502 to lysine. (B) The E502K mutation partially restores binding to CYK-4 S15L.CYK-4 fragments (1–232, 1–232 with a point mutation S15L, 35–232) were expressed as $^{35}$S-labeled protein and incubated with unlabeled ZEN-4 fragments (435–775, 435–775 with the E502K mutation, 609–775). ZEN-4 fragments were precipitated with anti-ZEN-4 antibody. CYK-4 (1–232) co-precipitated with ZEN-4 (435–775) but not with ZEN-4 (609–775) as shown in FIG. 13. The S15L mutation in CYK-4 abolishes its ability to bind to ZEN-4 (CYK-4 1–232 S15L and ZEN-4

435–775 wt). However, the suppressor mutation in ZEN-4 (E502K) partially recovered this interaction ((CYK-4 1–232 S15L and ZEN-4 435–775 E502K). The ZEN-4 E502K mutation does not affect the binding to wild-type CYK-4. (C) The majority of ZEN-4 is in a complex with CYK-4 in vivo. Extracts were made from wild type (N2) embryos or cyk-4(t1689ts) embryos. Sedimentation of ZEN-4 was analyzed by sucrose density gradient centrifugation followed by western blotting. The samples were spiked with the indicated standards and they ran identically in the two gradients. ZEN-4 from wild type embryos sediments at 8 S, whereas ZEN-4 from cyk-4 mutant embryos sediments at 7S.

EXAMPLE 11

CYK-4 and ZEN-4 Self-associate

Thus far it has been established that central spindle assembly is dependent on an interaction between CYK-4 and ZEN-4 and have defined the regions of both proteins that are required for this interaction. Interestingly, both binding domains contain coiled coil regions; these regions are required for binding activity. Since coiled coils are often dimerization motifs, and since kinesin motors are often composed of two motor domains tethered together through a coiled coil, it was examined whether CYK-4 and ZEN-4 are individually able self-associate.

To assess if CYK-4 self associates, full length CYK-4 and the CYK-4 derivative 1–232 were co-expressed. As a control, the full length protein was substituted by a truncated version lacking the N-terminal 120 amino acids. The longer CYK-4 fragments were immunoprecipitated with an antibody directed against the C-terminus of CYK-4 and the co-immunoprecipitation of the short N-terminal fragment was assessed. The N-terminal fragment bound to full length CYK-4 but not to CYK-4 lacking the N-terminal domain (FIG. 16A). These data demonstrate that CYK-4 self associates. This association is likely mediated by the coiled-coil domain.

The capacity of ZEN-4 to self-associate was examined using a similar strategy. Full length ZEN-4 was co-expressed with affinity-tagged deletion derivatives of ZEN-4. Neither the N-terminal region (1–507) nor the C-terminal region (604–775) of ZEN-4 bound appreciably to full length ZEN-4, but two internal fragments of ZEN-4 (503–775; 435–603) did bind to full length ZEN-4 (FIG. 16B). The region common to these two fragments consists of residues 503–603 which is the region predicted to form a coiled coil domain.

The ability of CYK-4 and ZEN-4 to self associate in vitro raise the possibility that in vivo, the CYK-4/ZEN-4 complex may contain, at a minimum, two molecules each of CYK-4 and ZEN-4.

Figure 16:
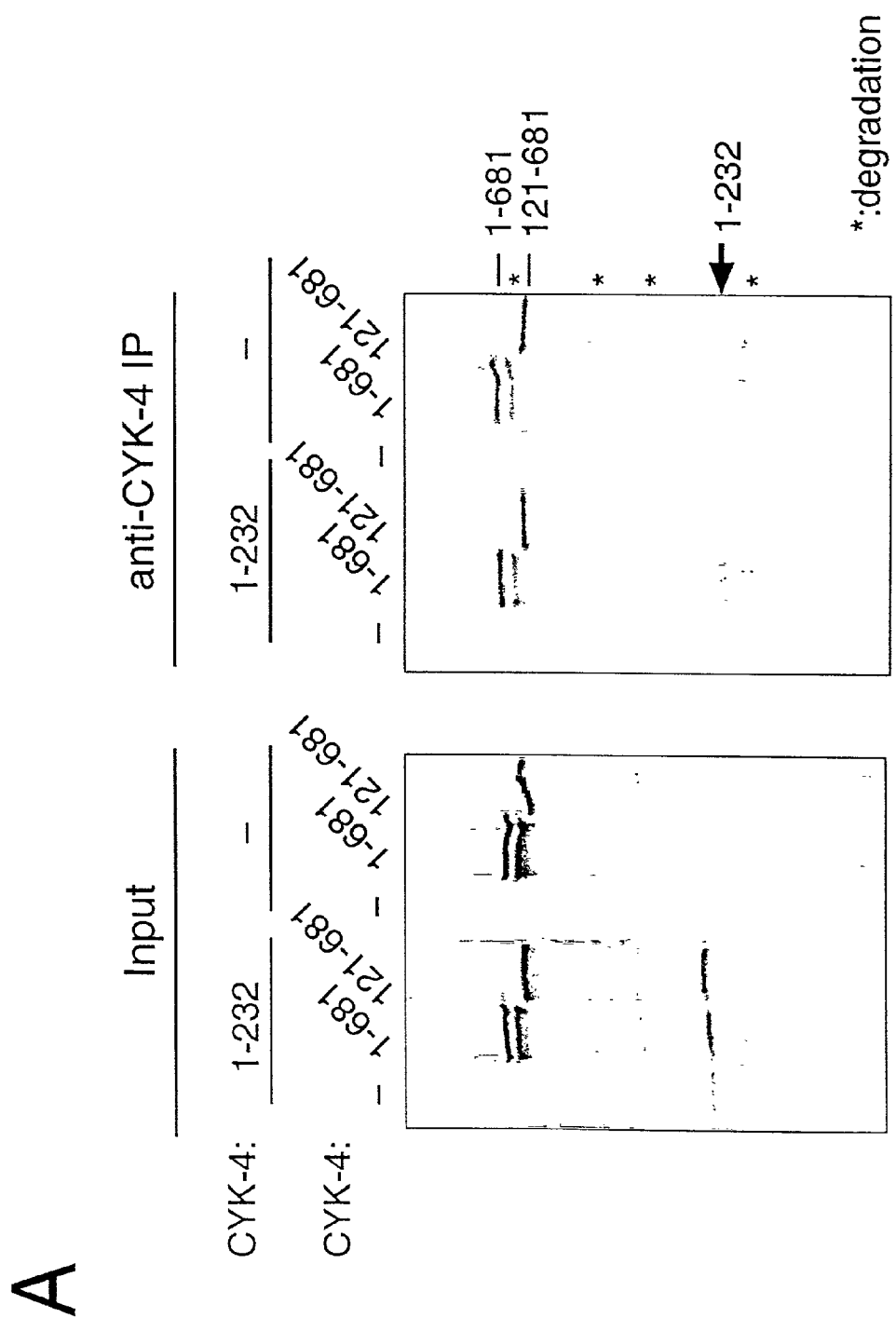
FIGS. 16A–16B: Self-association of CYK-4 and ZEN-4

FIG. 16 shows the self-association of both CYK-4 and ZEN-4

(A) CYK-4 (1–232), which does not contain the epitope recognized by the anti-CYK-4 antibody, was co-expressed as a $^{35}$S-labeled protein with CYK-4 (1–681) or (121–681), which do contain the epitope for this antibody (left panel). CYK-4 (1–681) and (121–681) were immunoprecipitated. CYK-4 (1–232) co-immunoprecipitated with CYK-4 (1–681), but not with CYK-4 (121–681). (B) CBD-tagged fragments of ZEN-4 (1–507, 503–775, 435–603 or 604–775) were co-expressed with untagged ZEN-4 (1–775) (left panel). CBD-tagged fragments were purified by affinity chromatography with chitin beads (right panel). Untagged ZEN-4 (1–775) copurified with CBD-ZEN-4 (503–775) and (435–603), but not with ZEN-4 (1–507) or (604–775). The low extent of labelling of 604–775 as compared to 435–603 is attributable to low cysteine and methionine content of the C-terminal fragment.

EXAMPLE 12

The human orthologs of CYK-4 and ZEN-4, HsCYK-4 and MKLP1, interact in vivo and colocalize.

In C. elegans, CYK-4 and ZEN-4 associate in vivo and in vitro and this complex is important for central spindle assembly and cytokinesis. To extend these findings it was evaluated whether mammalian cells contain a stable complex containing the human orthologs of these proteins, HsCYK-4/MgcRacGAP (Hirose et al., 2001; Toure et al., 1998; Wooltorton et al., 1999) and MKLP1, respectively. Extracts were prepared from mitotic Hela cells and antibodies directed against HsCYK-4 or MKLP1 were used for immunoprecipitation followed by western blotting. MKLP1 could be co-immunoprecipitated with anti-HsCYK-4 antibodies and vice versa (FIG. 17a). The immunoblots reveal that small amounts of HsCYK-4 and MKLP1 migrate with reduced mobility, likely due to phosphorylation.

To obtain evidence that these proteins play a similar role in human cells as was shown previously for the nematode proteins, the localization of HsCYK-4 and MKLP1 was examined in cultured (HeLa) human cells. During all stages of the cell cycle the two proteins precisely co-localize (insets FIG. 17b). In early anaphase, the two proteins localize to a discrete, central region of the central spindle. Three dimensional reconstruction of optically sectioned anaphase cells reveals that each bundle of microtubules in the central spindle is labeled at its distal end by MKLP1 antibodies. During mid-to-late anaphase, the MKLP1 staining region is 0.93+0.25 μm in length (n=56). This region largely corresponds to the region that appears deficient in tubulin staining, but this is a known artifact caused by epitope masking (Saxton and McIntosh, 1987). The extent of staining is somewhat narrower than previous ultrastructural determinations of the extent of microtubule overlap (>2 μM) (Mastronarde et al., 1993). Later in cleavage, both proteins localize to a discrete, central portion of the midbody. During interphase, some cells contain HsCYK-4 and MKLP1 in the nucleus, whereas others are do not. This is likely due to cell cycle regulated accumulation of these factors since, upon G2 arrest, HsCYK-4 and MKLP1 accumulate in the nucleus of all cells (data not shown). In addition, most cells contain brightly-staining, cortical ring-like structures. These structures likely correspond to division remnants; previous time-lapse microscopy with GFP-tagged CYK-4 and ZEN-4 in nematode embryos revealed that the central spindle matures into the midbody that later develops into a persistent spot or ring in the cell cortex. Thus there is a striking concordance between the biochemical properties and the subcellular localization of CYK-4/ZEN-4 in C. elegans embryos and HsCYK-4/MKLP1 in human cells. Since the names of the individual proteins vary from species to species, it is proposed to call this complex "centralspindlin". It is reasonable to speculate that centralspindlin performs a similar function in these two systems.

To gain insight into the architecture of centralspindlin, the hydrodynamic properties of its constituents were investigated. Lysates were prepared from mitotic Hela cells and run on sucrose density gradients. Western blotting of the gradient fractions indicates that HsCYK-4 and MKLP1 precisely co-migrate on the gradients with an S-value of 8 S (FIG. 17b). This sedimentation behavior is similar to that of centralspindlin isolated from C. elegans embryos. The two proteins also co-migrated on a gel filtration column with an apparent molecular weight of 800 kD (data not shown). Gel filtration chromatography can not accurately estimate native molecular mass of asymmetric particles, however, gel filtration data, combined with S-value measurements, allows a more accurate estimation of the native molecular mass. When the experimental values of centralspindlin are combined in this way, the complex is estimated to have a native molecular weight of ~300 kDa.

To determine if equimolar amounts of HsCYK-4 and MKLP1 are present in centralspindlin and whether or not other proteins are also present, the complex was immunopurified from a mitotic MAP (microtubule-associated protein) fraction that was eluted with ATP and 500 mM NaCl. Antibodies specific for HsCYK-4 and MKLP1 were used in parallel for the immunoprecipitation. Coomassie blue staining of both immunoprecipitates revealed two major bands and one minor band (FIG. 17C). Mass spectrometry analysis revealed that the slower migrating major band and the minor band are MKLP1 and the faster migrating major band is HsCYK-4. No additional bands reproducibly co precipitated with HsCYK-4 or MKLP1. Given that centralspindlin has a native molecular mass of 300 kD and that it does not appear to contain any proteins in addition to HsCYK-4 (70 kD) and MKLP1 (100 kD) and given that both components are capable of self-association, it is concluded that centralspindlin is a tetramer containing two molecules each of HsCYK-4 and MKLP1.

Figure 17:
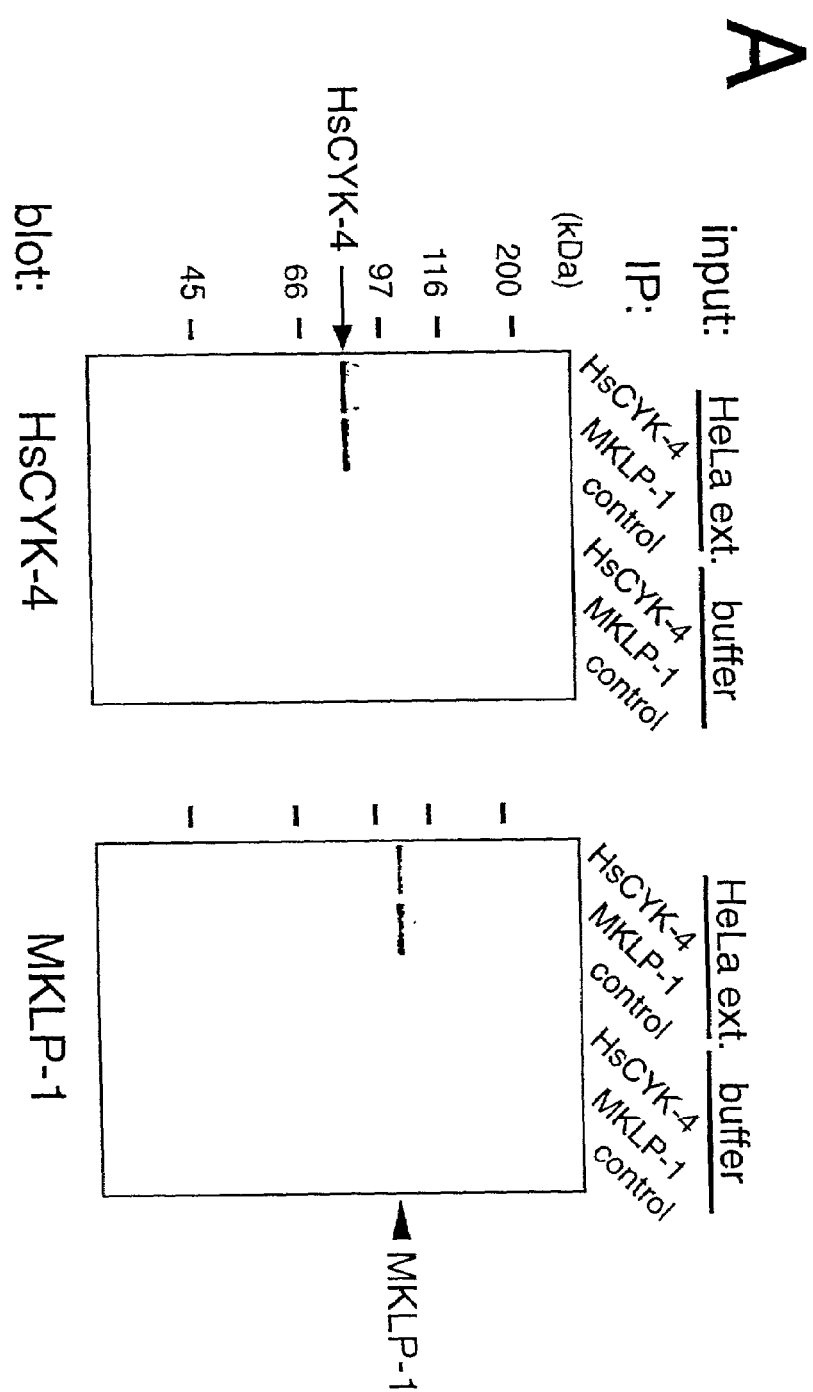
FIGS. 17A–17D: A complex of MKLP-1 and HsCYK-4 in HeLa cells
Figure 17:
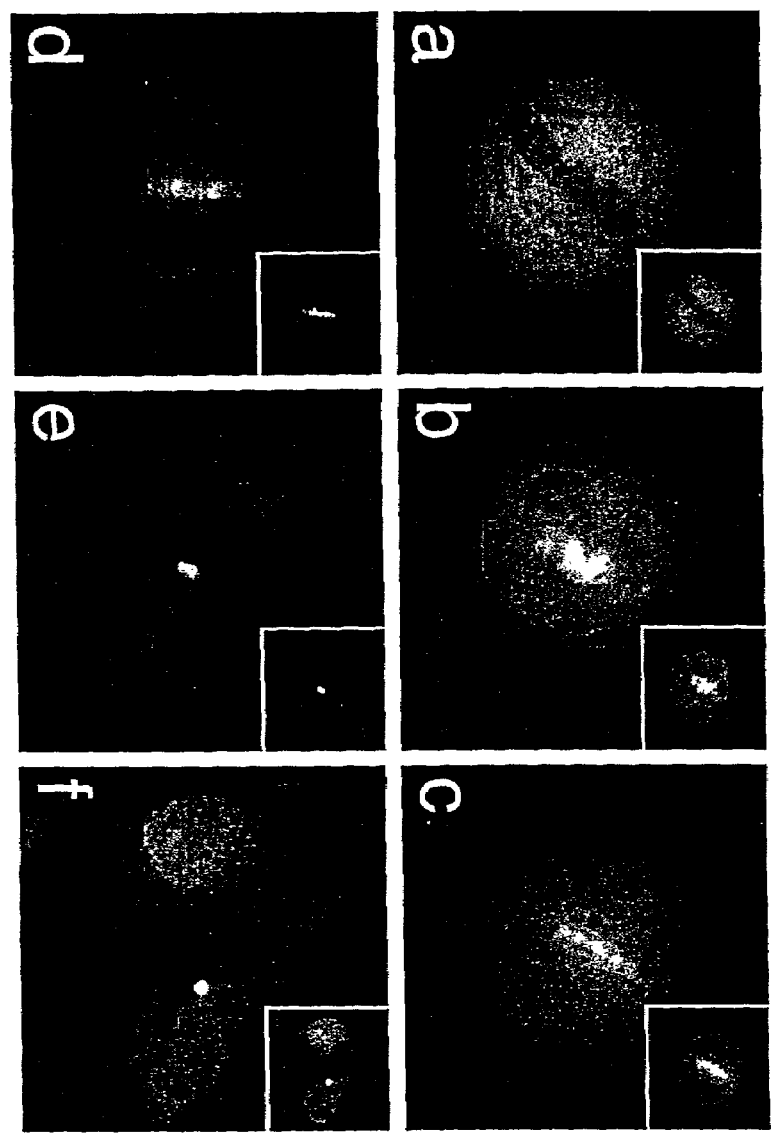
Figure 17:
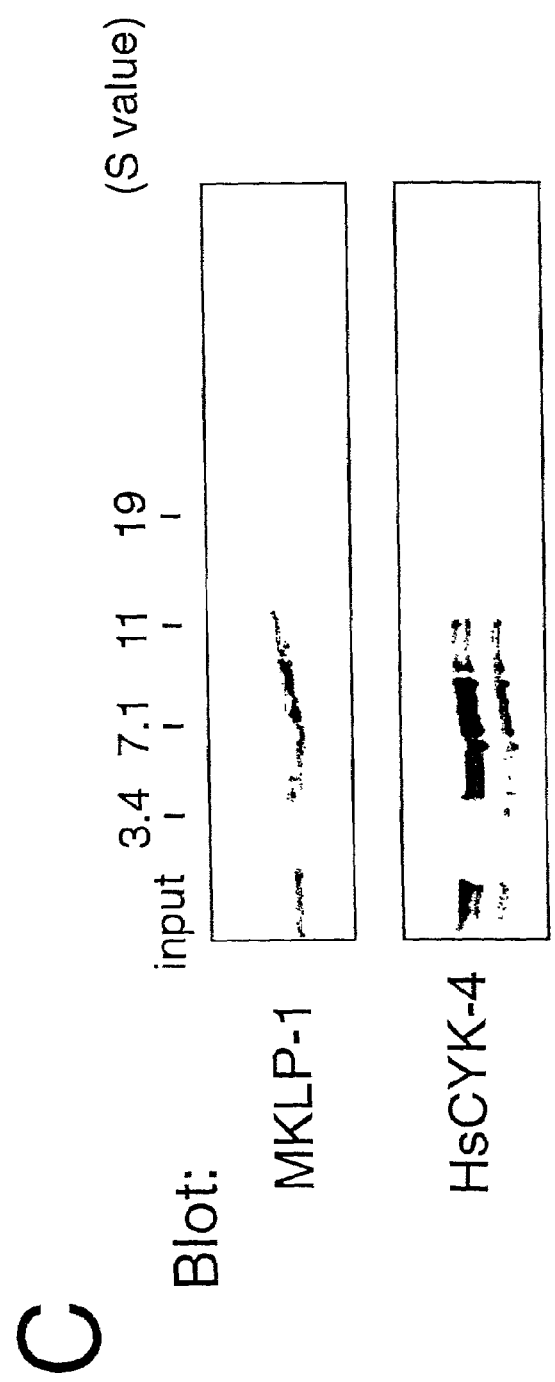
Figure 17:
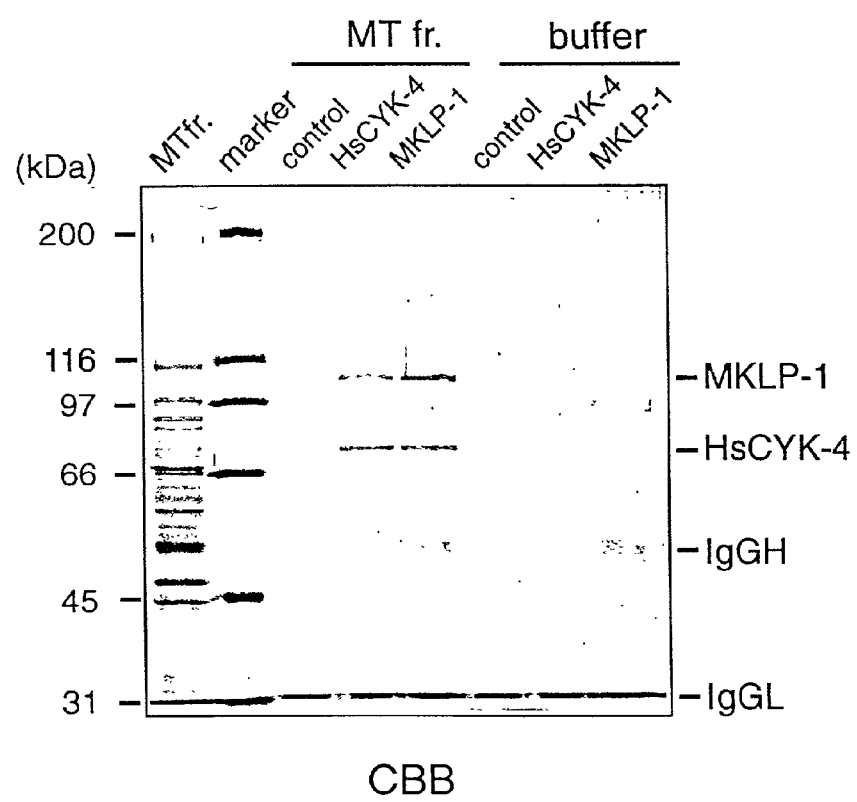
Figure 18:
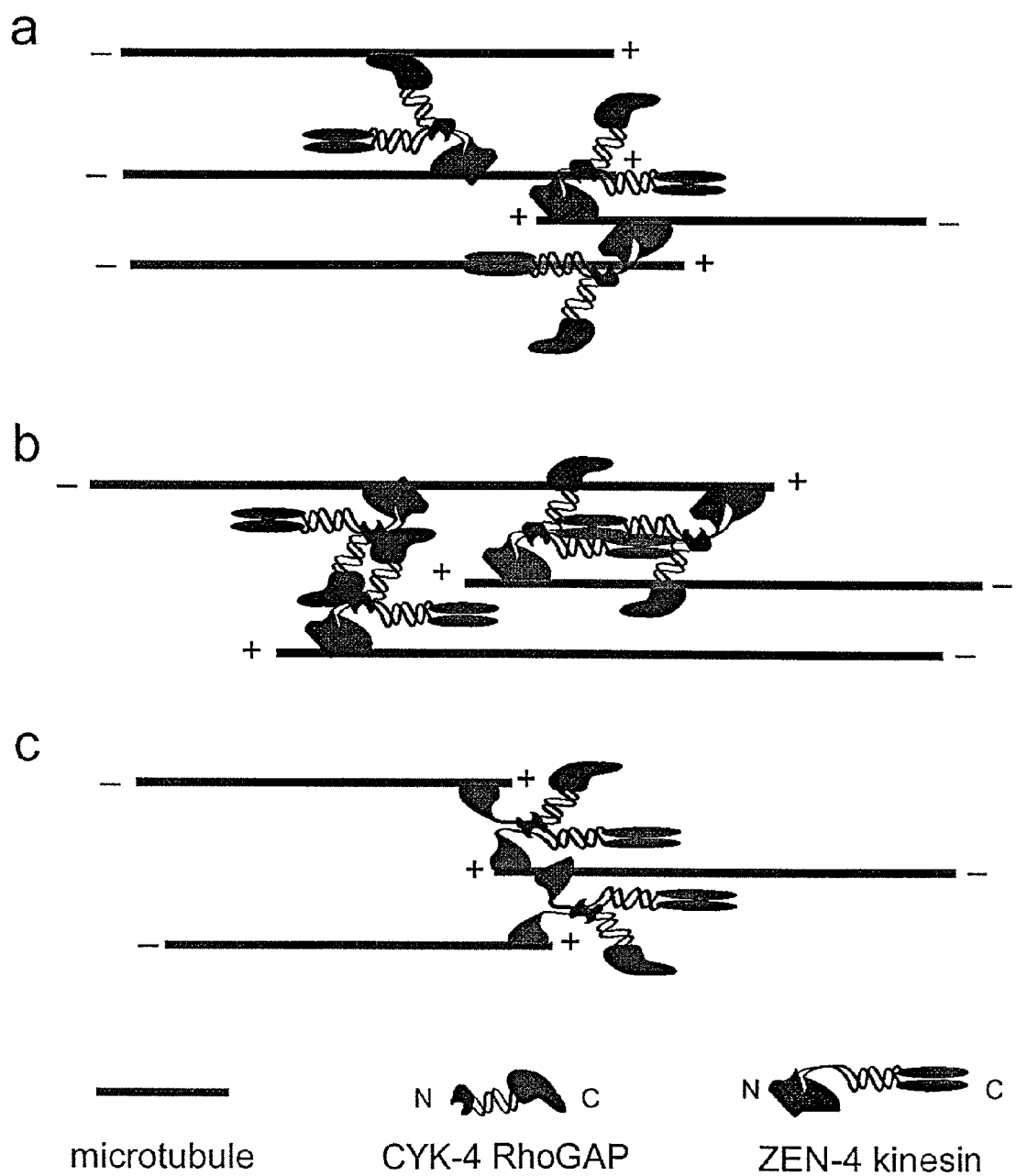
FIG. 18: Centralspindlin and its role in the formation of central spindle

FIG. 17 shows that there exists a complex of MKLP-1 and HsCYK-4 in HeLa cells

HsCYK-4/MgcRacGAP and MKLP-1, the human orthologs of CYK-4 and ZEN-4, respectively, exist as a complex in mitotic HeLa cells. (A) HsCYK-4 and MKLP-1 were immunoprecipitated from HeLa cell lysate with specific rabbit antibodies (IP:HsCYK-4 or MKLP-1) and blotted with specific mouse antibodies (blot: HsCYK-4 or MKLP-1). HsCYK-4 co-immunoprecipitated with MKLP-1 and vice versa. (B) HsCYK-4 and MKLP1 co-localize to the central spindle and the midbody. Hela cells were fixed and immunostained with anti-CYK-4, anti-MKLP1, anti-tubulin antibodies and DNA was stained with Hoechst. Shown are cells in interphase (a) and various stages of cytokinesis (b–f). In main panels, staining of CYK-4 (green), microtubules (red) and DNA (blue) was shown. In inset, staining of CYK-4 (green) and MKLP1 (red) was shown. (C) HeLa cell lysates were analyzed by sucrose density gradient centrifugation followed by blotting with anti-MKLP-1 antibody or anti-HsCYK-4 antibody. HsCYK-4 and MKLP-1 co-sediment at 8S. The lowest band reacting with the CYK-4 antibody is caused by proteolysis of the N-terminus. (D) MKLP-1 and HsCYK-4 complex was immunoprecipitated from a microtubule-binding fraction (MTfr.) of mitotic HeLa cells with specific antibodies. Major 110 kDa and 75 kDa bands were identified by mass spectrometry as MKLP-1 and HsCYK-4, respectively. The minor band at 115 kDa also corresponds to MKLP1. Broad bands around 50 kDa and bands near gel bottom are heavy (IgGH) and light (IgGL) chains of immunoglobulin leaked from antibody beads.

TABLE 1

| genotype | stage at time of shift to 25° C. | percent viable | phenotype of surviving progeny | N |
|---|---|---|---|---|
| N2 (wild type) | embryos | 98.8% | wild-type | 485 |
| cyk-4 | (not shifted) | 70.2% | fertile | 198 |
| cyk-4 | embryos | 1.5% | sterile, highly Unc | 324 |
| cyk-4 | L1 larvae | 100.0% | sterile, highly Unc | 89 |
| cyk-4 | L2/L3 | 100.0% | sterile, highly Unc | 55 |
| cyk-4 | L4 | 100.0% | fertile, lay dead embryos | 52 |
| cyk-4, xsEx1 [cyk-4: GFP] | embryos | 59.4% | fertile | 350 |

Except for the N2 control, the complete genotype of the strain was unc-32(e189) cyk-4(t1689ts). Gravid hermaphrodites were allowed to lay embryos for 2 hours at the permissive temperature. The adult was then removed and the number of embryos counted. After 24 hours at the indicated temperature the number of unhatched embryos was then counted.

TABLE 2

| injected dsRNA | locus | percent cytokinesis defective (N) | number of time lapse recordings | number cytokinesis defective | additional phenotypes |
|---|---|---|---|---|---|
| RhoA | Y51H4A.B | 95% (175) | 15 | 15 (100%) | |
| Rac-1 | C09G12.8 B | Not emb. lethal | 5 | 0 | |
| Cdc42 | R07G3.1 | 12% (74) | 22 | 3 (14%) | symmetric 1st division (5/22); no rotation in P1 (12/22); rotation of AB (2/22) |
| others | F22E12.2 | Not emb. lethal | | | |
| | Y32F6B.3 | Not emb. lethal | | | |
| | K03D3.9 | Not emb. lethal | | | |

Young adult hermaphrodites were injected with the indicated dsRNAs and broods of laid embryos were scored for embryonic lethality. dsRNAs that induced embryonic lethality were further characterized by dissecting embryos and scoring for multinucleate embryos and by performing time lapse recordings and evaluating cytokinesis, spindle orientation in the one-cell embryo (symmetric or asymmetric first cleavage), and spindle positioning in the P1 and AB blastomeres.

TABLE 3

| genotype | temperature | total number of stained remnants | total number of cells | average number of remnants/ cell | number of embryos |
|---|---|---|---|---|---|
| N2 (wildtype) | 25° C. | 110 | 137 | 0.80 | 16 |
| zen-4 (or198ts) | 16° C. | 61 | 83 | 0.73 | 10 |
| zen-4 (or198ts) | 25° C. (18 min.) | 11 | 147 | 0.07 | 24 |
| N2 (wildtype) | 25° C. | 150 | 205 | 0.73 | 22 |

TABLE 3-continued

| genotype | temperature | total number of stained remnants | total number of cells | average number of remnants/ cell | number of embryos |
|---|---|---|---|---|---|
| cyk-4 (t1689ts) | 16° C. | 61 | 98 | 0.62 | 10 |
| cyk-4 (t1689ts) | 25° C. (15 min.) | 10 | 176 | 0.06 | 19 |

Wild-type and zen-4(or153ts) embryos grown at the indicated temperatures were fixed and stained for Cyk-4. Similarly, Wild-type and cyk-4(t1689ts) grown at the indicated temperatures were fixed and stained for Zen-4/CeMKlp1. The number of cells in each embryo and the number of remnants staining with Cyk-4 or Zen-4 antibodies was counted.

REFERENCES

Adams, R. R., Tavares, A. A., Salzberg, A., Bellen, H. J., and Glover, D. M. (1998). pavarotti encodes a kinesin-like protein required to organize the central spindle and contractile ring for cytokinesis. Genes Dev 12, 1483–94.

Aktories, K., and Hall, A. (1989). Botulinum ADP-ribosyltransferase C3: a new tool to study low molecular weight GTP-binding proteins. Trends Pharmacol Sci 10, 415–8.

Bosher, J.M. and Labouesse, M., (2000), Nat Cell Biol, February; 2(2):E31–6

Busson, S., Dujardin, D., Moreau, A., Dompierre, J., and De Mey, J. R. (1998). Dynein and dynactin are localized to astral microtubules and at cortical sites in mitotic epithelial cells. Curr Biol 8, 541–4.

Cao, L. G., and Wang, Y. L. (1996). Signals from the spindle midzone are required for the stimulation of cytokinesis in cultured epithelial cells. Mol Biol Cell 7, 225–32.

Carmena, M., Riparbelli, M. G., Minestrini, G., Tavares, A. M., Adams, R., Callaini, G., and Glover, D. M. (1998). *Drosophila* polo kinase is required for cytokinesis. J Cell Biol 143, 659–71.

Carminati, J. L., and Stearns, T. (1997). Microtubules orient the mitotic spindle in yeast through dynein-dependent interactions with the cell cortex. J Cell Biol 138, 629–41.

Case, R. B., Rice, S., Hart, C. L., Ly, B., and Vale, R. D. (2000). Role of the kinesin neck linker and catalytic core in microtubule-based motility. Curr Biol 10, 157–60.

Castrillon, D. H., and Wasserman, S. A. (1994). Diaphanous is required for cytokinesis in *Drosophila* and shares domains of similarity with the products of the limb deformity gene. Development 120, 3367–77.

Chang, F., Drubin, D., and Nurse, P. (1997). cdc12p, a protein required for cytokinesis in fission yeast, is a component of the cell division ring and interacts with profilin. J Cell Biol 137, 169–82.

Chui, K. K., Rogers, G. C., Kashina, A. M., Wedaman, K. P., Sharp, D. J., Nguyen, D. T., Wilt, F., and Scholey, J. M. (2000). Roles of two homotetrameric kinesins in sea urchin embryonic cell division. J Biol Chem 275, 38005–11.

Drechsel, D. N., Hyman, A. A., Hall, A., and Glotzer, M. (1997). A requirement for Rho and Cdc42 during cytokinesis in Xenopus embryos. Curr Biol 7, 12–23.

Dutartre, H., Davoust, J., Gorvel, J. P., and Chavrier, P. (1996). Cytokinesis arrest and redistribution of actin-cytoskeleton regulatory components in cells expressing the Rho GTPase CDC42Hs. J Cell Sci 109, 367–77.

Echard, A., Jollivet, F., Martinez, O., Lacapere, J. J., Rousselet, A., Janoueix-Lerosey, I., and Goud, B. (1998). Interaction of a Golgi-associated kinesin-like protein with Rab6. Science 279, 580–5.

Eckley, D. M., Ainsztein, A. M., Mackay, A. M., Goldberg, I. G., and Earnshaw, W. C. (1997). Chromosomal proteins and cytokinesis: patterns of cleavage furrow formation and inner centromere protein positioning in mitotic heterokaryons and mid-anaphase cells. J Cell Biol 136, 1169–83.

Evangelista, M., Blundell, K., Longtine, M. S., Chow, C. J., Adames, N., Pringle, J. R., Peter, M., and Boone, C. (1997). Bni1p, a yeast formin linking cdc42p and the actin cytoskeleton during polarized morphogenesis. Science 276, 118–22.

Field, C., Li, R., and Oegema, K. (1999). Cytokinesis in eukaryotes: a mechanistic comparison. Curr Opin Cell Biol 11, 68–80.

Fire, A., Xu, S., Montgomery, M. K., Kostas, S. A., Driver, S. E., and Mello, C. C. (1998). Potent and specific genetic interference by double-stranded RNA in *Caenorhabditis elegans*. Nature 391, 806–11.

Fire, A., (1999), Trends Genet, Sep; 15(9):358–63

Fontijn, R. D., Goud, B., Echard, A., Jollivet, F., van Marle, J., Pannekoek, H., and Horrevoets, A. J. (2001). The Human Kinesin-Like Protein RB6K Is under Tight Cell Cycle Control and Is Essential for Cytokinesis. Mol Cell Biol 21, 2944–55.

Fujiwara, T., Tanaka, K., Inoue, E., Kikyo, M., and Takai, Y. (1999). Bni1p Regulates Microtubule-Dependent Nuclear Migration through the Actin Cytoskeleton in Saccharomyces cerevisiae. Mol Cell Biol 19, 8016–8027.

Giansanti, M. G., Bonaccorsi, S., Williams, B., Williams, E. V., Santolamazza, C., Goldberg, M. L., and Gatti, M. (1998). Cooperative interactions between the central spindle and the contractile ring during *Drosophila* cytokinesis. Genes Dev 12, 396–410.

Glotzer, M. (1997). The mechanism and control of cytokinesis. Curr Opin Cell Biol 9, 815–23.

Glotzer, M. (1997). Cytokinesis. Curr Biol 7, R274–6.

Gönczy, P., Pichler, S., Kirkham, M., and Hyman, A. A. (1999a). Cytoplasmic dynein is required for distinct aspects of MTOC positioning, including centrosome separation, in the one cell stage *Caenorhabditis elegans* embryo. J Cell Biol 147, 135–50.

Gönczy, P., Schnabel, H., Kaletta, T., Amores, A. D., Hyman, T., and Schnabel, R. (1999b). Dissection of cell division processes in the one cell stage *Caenorhabditis elegans* embryo by mutational analysis. J Cell Biol 144, 927–46.

Hill, E., Clarke, M., and Barr, F. A. (2000). The Rab6-binding kinesin, Rab6-KIFL, is required for cytokinesis. Embo J 19, 5711–9.

Hirose, K., Kawashima, T., Iwamoto, I., Nosaka, T., and Kitamura, T. (2001). MgcRacGAP is involved in cytokinesis through associating with mitotic spindle and midbody. J Biol Chem 276, 5821–8.

Hurley, J. H., and Meyer, T. (2001). Subcellular targeting by membrane lipids. Curr Opin Cell Biol 13, 146–52.

Hyman, A. A., and White, J. G. (1987). Determination of cell division axes in the early embryogenesis of *Caenorhabditis elegans*. J Cell Biol 105, 2123–35.

Hyman, A. A. (1989). Centrosome movement in the early divisions of *Caenorhabditis elegans*: a cortical site determining centrosome position. J Cell Biol 109, 1185–93.

Imamura, H., Tanaka, K., Hihara, T., Umikawa, M., Kamei, T., Takahashi, K., Sasaki, T., and Takai, Y. (1997). Bni1p and Bnrlp: downstream targets of the Rho family small G-proteins which interact with profilin and regulate actin cytoskeleton in Saccharomyces cerevisiae. Embo J 16, 2745–55.

Jantsch-Plunger, V., and Glotzer, M. (1999). Depletion of syntaxins in the early Caenorhabditis elegans embryo reveals a role for membrane fusion events in cytokinesis. Curr Biol 9, 738–45.

Jantsch-Plunger, V., Gonczy, P., Romano, A., Schnabel, H., Hamill, D., Schnabel, R., Hyman, A. A., and Glotzer, M. (2000). CYK-4. A rho family gtpase activating protein (gap) required for central spindle formation and cytokinesis. J Cell Biol 149, 1391–404.

Kaitna, S., Mendoza, M., Jantsch-Plunger, V., and Glotzer, M. (2000). Incenp and an aurora-like kinase form a complex essential for chromosome segregation and efficient completion of cytokinesis [In Process Citation]. Curr Biol 10, 1172–81.

Kishi, K., Sasaki, T., Kuroda, S., Itoh, T., and Takai, Y. (1993). Regulation of cytoplasmic division of Xenopus embryo by rho p21 and its inhibitory GDP/GTP exchange protein (rho GDI). J Cell Biol 120, 1187–95.

Kosako, H., Goto, H., Yanagida, M., Matsuzawa, K., Fujita, M., Tomono, Y., Okigaki, T., Odai, H., Kaibuchi, K., and Inagaki, M. (1999). Specific accumulation of Rho-associated kinase at the cleavage furrow during cytokinesis: cleavage furrow-specific phosphorylation of intermediate filaments. Oncogene 18, 2783–8.

Kull, F. J., Sablin, E. P., Lau, R., Fletterick, R. J., and Vale, R. D. (1996). Crystal structure of the kinesin motor domain reveals a structural similarity to myosin. Nature 380, 550–5.

Kuriyama, R., Dragas-Granoic, S., Maekawa, T., Vassilev, A., Khodjakov, A., and Kobayashi, H. (1994). Heterogeneity and microtubule interaction of the CHO1 antigen, a mitosis-specific kinesin-like protein. Analysis of subdomains expressed in insect sf9 cells. J Cell Sci 107, 3485–99.

Lamarche, N., and Hall, A. (1994). GAPs for rho-related GTPases. Trends Genet 10, 436–40.

Larkin, K., and Danilchik, M.V. (1999), Dev Biol. 214: 215–226

Lee, K. S., Yuan, Y. L., Kuriyama, R., and Erikson, R. L. (1995). Plk is an M-phase-specific protein kinase and interacts with a kinesin-like protein, CHO1/MKLP-1. Mol Cell Biol 15, 7143–51.

Lewis, J. A., and Fleming, J. T. (1995). Basic culture methods. Methods Cell Biol 48, 3–29.

Mabuchi, I., Hamaguchi, Y., Fujimoto, H., Morii, N., Mishima, M., and Narumiya, S. (1993). A rho-like protein is involved in the organisation of the contractile ring in dividing sand dollar eggs. Zygote 1, 325–31.

Mackay, A. M., Ainsztein, A. M., Eckley, D. M., and Earnshaw, W. C. (1998). A dominant mutant of inner centromere protein (INCENP), a chromosomal protein, disrupts prometaphase congression and cytokinesis. J Cell Biol 140, 991–1002.

Martineau-Thuillier, S., Andreassen, P. R., and Margolis, R. L. (1998). Colocalization of TD-60 and INCENP throughout G2 and mitosis: evidence for their possible interaction in signalling cytokinesis. Chromosoma 107, 461–70.

Mastronarde, D. N., McDonald, K. L., Ding, R., and McIntosh, J. R. (1993). Interpolar spindle microtubules in PTK cells. J Cell Biol 123, 1475–89.

Mello, C. C., Kramer, J. M., Stinchcomb, D., and Ambros, V. (1991). Efficient gene transfer in C.elegans: extrachromosomal maintenance and integration of transforming sequences. Embo J 10, 3959–70.

Miller, R. K., Matheos, D., and Rose, M. D. (1999). The cortical localization of the microtubule orientation protein, Kar9p, is dependent upon actin and proteins required for polarization. J Cell Biol 144, 963–75.

Moorman, J. P., Bobak, D. A., and Hahn, C. S. (1996). Inactivation of the small GTP binding protein Rho induces multinucleate cell formation and apoptosis in murine T lymphoma EL4. J Immunol 156, 4146–53.

Nislow, C., Lombillo, V. A., Kuriyama, R., and McIntosh, J. R. (1992). A plus-end-directed motor enzyme that moves antiparallel microtubules in vitro localizes to the interzone of mitotic spindles. Nature 359, 543–7.

O'Connell, C. B., Wheatley, S. P., Ahmed, S., and Wang, Y. L. (1999). The small GTP-binding protein rho regulates cortical activities in cultured cells during division. J Cell Biol 144, 305–13.

O'Connell, K. F., Leys, C. M., and White, J. G. (1998). A genetic screen for temperature-sensitive cell-division mutants of Caenorhabditis elegans. Genetics 149, 1303–21.

Okada, Y., and Hirokawa, N. (2000). Mechanism of the single-headed processivity: diffusional anchoring between the K-loop of kinesin and the C terminus of tubulin. Proc Natl Acad Sci USA 97, 640–5.

Powers, J., Bossinger, O., Rose, D., Strome, S., and Saxton, W. (1998). A nematode kinesin required for cleavage furrow advancement. Curr Biol 8, 1133–6.

Prokopenko, S. N., Brumby, A., O'Keefe, L., Prior, L., He, Y., Saint, R., and Bellen, H. J. (1999). A putative exchange factor for Rho1 GTPase is required for initiation of cytokinesis in Drosophila. Genes Dev 13, 2301–14.

Raich, W. B., Moran, A. N., Rothman, J. H., and Hardin, J. (1998). Cytokinesis and midzone microtubule organization in Caenorhabditis elegans require the kinesin-like protein ZEN-4. Mol Biol Cell 9, 2037–49.

Rappaport, R. (1985). Repeated furrow formation from a single mitotic apparatus in cylindrical sand dollar eggs. J Exp Zool 234, 167–71.

Reddien, P., and Horvitz, H. (2000). CED-2/CrkII and CED-10/Rac control phagocytosis and cell migration in Caenorhabditis elegans. Nature Cell Biology 2, 131–136.

Remington's Pharmaceutical Sciences, 1980, Mack Publ. Co. Easton, Pa., Osol (ed.)

Remington: The Science and Practice of Pharmacy, 2000 (20$^{th}$ edition; Book News, Inc.)

Rice, S., Lin, A. W., Safer, D., Hart, C. L., Naber, N., Carragher, B. O., Cain, S. M., Pechatnikova, E., Wilson-Kubalek, E. M., Whittaker, M., Pate, E., Cooke, R., Taylor, E. W., Milligan, R. A., and Vale, R. D. (1999). A structural change in the kinesin motor protein that drives motility. Nature 402, 778–84.

Rieder, C. L., Khodjakov, A., Paliulis, L. V., Fortier, T. M., Cole, R. W., and Sluder, G. (1997). Mitosis in vertebrate somatic cells with two spindles: implications for the metaphase/anaphase transition checkpoint and cleavage. Proc Natl Acad Sci U S A 94, 5107–12.

Sablin, E. P., Kull, F. J., Cooke, R., Vale, R. D., and Fletterick, R. J. (1996). Crystal structure of the motor domain of the kinesin-related motor ncd. Nature 380, 555–9.

Sambrook et al., 2000, Molecular Cloning, Third Edition

Savoian, M. S., Earnshaw, W. C., Khodjakov, A., and Rieder, C. L. (1999). Cleavage furrows formed between centrosomes lacking an intervening spindle and chromosomes contain microtubule bundles, INCENP, and CHO1 but not CENP-E. Mol Biol Cell 10, 297–311.

Saxton, W. M., and McIntosh, J. R. (1987). Interzone microtubule behavior in late anaphase and telophase spindles. J Cell Biol 105, 875–86.

Schumacher, J. M., Golden, A., and Donovan, P. J. (1998). AIR-2: An Aurora/Ipl1-related protein kinase associated with chromosomes and midbody microtubules is required for polar body extrusion and cytokinesis in *Caenorhabditis elegans* embryos. J Cell Biol 143, 1635–46.

Settleman, J., and Foster, R., (1995), Methods Enzymol; 256:105–13

Severson, A. F., Schumacher, J., Hamill, D. R., Carter, J. C., and Bowerman, B. (2000). The Aurora/Ipl1p-Related Kinase AIR-2 Functions at Metaphase to Recruit theKinesin-like Protein ZEN-4 to the Mitotic Spindle Midzone and is Required forCytokinesis. Current Biology, October 5;10(19): 1162–71.

Sharp, D. J., Kuriyama, R., and Baas, P. W. (1996). Expression of a kinesin-related motor protein induces Sf9 cells to form dendrite-like processes with nonuniform microtubule polarity orientation. J Neurosci 16, 4370–5.

Sharp, P.A., (1999), Genes Dev, January 15; 13(2):139–41

Skop, A. R., and White, J. G. (1998). The dynactin complex is required for cleavage plane specification in early *Caenorhabditis elegans* embryos. Curr Biol 8, 1110–6.

Sugihara, K., Nakatsuji, N., Nakamura, K., Nakao, K., Hashimoto, R., Otani, H., Sakagami, H., Kondo, H., Nozawa, S., Aiba, A., and Katsuki, M. (1998). Rac1 is required for the formation of three germ layers during gastrulation. Oncogene 17, 3427–33.

Sulston, J. E., and Horvitz, H. R., (1977), Dev Biol. 56:110–156

Swan, K. A., Severson, A. F., Carter, J. C., Martin, P. R., Schnabel, H., Schnabel, R., and Bowerman, B. (1998). cyk-1: a *C. elegans* FH gene required for a late step in embryonic cytokinesis. J Cell Sci 111, 2017–27.

Tatsumoto, T., Xie, X., Blumenthal, R., Okamoto, I., and Miki, T. (1999). Human ECT2 is an exchange factor for rho GTPases, phosphorylated in G2/M phases, and involved in cytokinesis [In Process Citation]. J Cell Biol 147, 921–8.

Timmons, L., and Fire, A. (1998). Specific interference by ingested dsRNA. Nature 395, 854.

Toure, A., Dorseuil, O., Morin, L., Timmons, P., Jegou, B., Reibel, L., and Gacon, G. (1998). MgcRacGAP, a new human GTPase-activating protein for Rac and Cdc42 similar to *Drosophila* rotundRacGAP gene product, is expressed in male germ cells. J Biol Chem 273, 6019–23.

Vale, R. D., and Fletterick, R. J. (1997). The design plan of kinesin motors. Annu Rev Cell Dev Biol 13, 745–77.

Vale, R. D., and Milligan, R. A. (2000). The way things move: looking under the hood of molecular motor proteins. Science 288, 88–95.

Van Aelst, L., and D'Souza-Schorey, C. (1997). Rho GTPases and signaling networks. Genes Dev 11,2295–322.

Van de Putte T, Zwijsen A, Lonnoy O, Rybin V, Cozijnsen M, Francis A, Baekelandt V, Kozak C A, Zerial M, Huylebroeck D. Mice with a homozygous gene trap vector insertion in mgcRacGAP die during pre-implantation development.Mech Dev. 2001 April;102(1–2):33–44

Waddle, J. A., Cooper, J. A., and Waterston, R. H. (1994). Transient localized accumulation of actin in *Caenorhabditis elegans* blastomeres with oriented asymmetric divisions. Development 120, 2317–28.

Watanabe, N., Madaule, P., Reid, T., Ishizaki, T., Watanabe, G., Kakizuka, A., Saito, Y., Nakao, K., Jockusch, B. M., and Narumiya, S. (1997). p140mDia, a mammalian homolog of *Drosophila* diaphanous, is a target protein for Rho small GTPase and is a ligand for profilin. Embo J 16, 3044–56.

Wheatley, S. P., and Wang, Y. L. (1996). Midzone microtubules are continuously required for cytokinesis in cultured epithelial cells. J. Cell Biol. 135, 981–989.

Woollard, A., and Hodgkin, J. (1999). Stu-7/air-2 is a *C. elegans* aurora homologue essential for chromosome segregation during embryonic and post-embryonic development. Mech Dev 82, 95–108.

The invention claimed is:

1. A method for determining whether a compound has the potential to inhibit cytokinesis by determining the compound's ability to inhibit the function of a CYK-4 protein comprising amino acid residues 360–536 of SEQ ID NO:2 to promote GTP hydrolysis by a Rho family GTPase, the method comprising:
   (i) incubating the Rho family GTPase with GTP for a period of time sufficient to allow saturation of the Rho family GTPase's GTP binding sites;
   (ii) adding a CYK-4 protein comprising amino acid residues 360–536 of SEQ ID NO:2 to the Rho family GTPase and the GTP in the presence and absence of the compound, wherein the CYK-4 protein, in the absence of the compound, stimulates GTP hydrolysis by the Rho family GTPase; and
   (iii) determining an amount of GTP that is hydrolyzed in the presence and absence of the compound;
   wherein the compound is determined to have the potential to inhibit cytokinesis if the compound inhibits the CYK-4 stimulated GTP hydrolysis determined in (iii).

2. The method of claim 1, wherein the Rho family GTPase is a full-length Rho family GTPase protein or a fragment of the Rho family GTPase protein that retains GTPase activity.

3. The method of claim 2, wherein the CYK-4 protein is human CYK-4 (SEQ ID NO:2).

4. The method of claim 3, wherein the Rho family GTPase is selected from the group consisting of human RhoA, human RhoB, human RhoC, human RAC1, human RAC2, human RAC3, and human GB25.

5. The method of claim 4, wherein the Rho family GTPase is human RhoA.

6. The method of claim 2, wherein the Rho family GTPase is immobilized on a solid support.

7. The method of claim 2, wherein the GTP is labeled.

8. The method of claim 7, wherein the GTP is labeled with a radioisotope or a fluorescent label.

9. A method for determining whether a compound has the potential to inhibit cytokinesis by determining the compound's ability to inhibit the function of a CYK-4 protein comprising amino acid residues 1–120 of SEQ ID NO:2 to bind to a member of the MKLP1 subfamily of kinesin-like proteins, the method comprising:
   (i) incubating a CYK-4 protein comprising amino acid residues 1–120 of SEQ ID NO:2 for a period of time with the MKLP1 protein subfamily member in the presence and absence of the compound, wherein the CYK-4 protein, in the absence of the compound, binds the MKILP1 protein subfamily member; and
   (ii) determining an amount of the MKLP1 protein subfamily member bound to the CYK-4 protein in the presence and absence of the compound;
   wherein the compound is determined to have the potential to inhibit cytokinesis if the compound inhibits the binding of the CYK-4 protein to the MKLP1 protein subfamily member as determined in (ii).

10. The method of claim 9, wherein the MKLP1 protein subfamily member is a full-length MKLP1 protein or a fragment of the MKLP1 protein subfamily member that binds the CYK-4 protein.

11. The method of claim 10, wherein the MKLP 1 protein subfamily member is selected from the group consisting of CeM03D4.1b (SEQ ID NO:7) and HsMKLP1 (SEQ ID NO:8).

12. The method of claim 11, wherein the MKLP 1 protein subfamily member is HsMKLP1 (SEQ ID NO:8).

13. The method of claim 11, wherein the CYK-4 protein is human CYK-4 (SEQ ID NO:2).

14. The method of claim 10, wherein the CYK-4 protein is immobilized on a solid support, and wherein the MKLP1 protein subfamily member or the fragment of the MKLP1 protein subfamily member is labeled.

15. The method of claim 14, wherein the label is a radioisotope, a fluorescent label, or a hapten.

16. The method of claim 10, wherein step (i) is performed in solution.

17. A method for determining whether a compound has the potential to inhibit cytokinesis by determining the compound's ability to inhibit CYK-4 function by determining the compound's ability to inhibit self association of a CYK-4 protein comprising amino acid residues 1–120 of SEQ ID NO:2, the method comprising:
  (i) incubating in the presence and absence of the compound a first CYK-4 protein comprising amino acid residues 1–120 of SEQ ID NO:2 with a second CYK-4 protein comprising amino acid residues 1–120 of SEQ ID NO:2, wherein, in the absence of the compound, the first CYK-4 protein binds to the second CYK-4 protein, and wherein the second CYK-4 protein is labeled; and
  (ii) determining an amount of the second CYK-4 protein bound to the first CYK-4 protein;
  wherein the compound is determined to have the potential to inhibit cytokinesis if the compound inhibits the binding of the first CYK-4 protein to the second CYK-4 protein as determined in (ii).

18. The method of claim 17, wherein the first CYK-4 protein is human CYK-4 (SEQ ID NO:2).

19. The method of claim 17, wherein the first CYK-4 protein is immobilized on a solid support, and wherein the second CYK-4 protein is labeled.

20. The method of claim 19, wherein the second CYK-4 protein is labeled with a radioisotope label, a fluorescent label, a hapten label, a peptide label, or an enzyme label.

21. The method of claim 17, wherein the first CYK-4 protein is identical to the second CYK-4 protein.

22. The method of claim 17, wherein the first CYK-4 protein is different from the second CYK-4 protein.

* * * * *